(12) United States Patent
Bisacchi et al.

(10) Patent No.: US 6,344,450 B1
(45) Date of Patent: Feb. 5, 2002

(54) LACTAM COMPOUNDS AND THEIR USE AS INHIBITORS OF SERINE PROTEASES AND METHOD

(75) Inventors: Gregory S. Bisacchi, Ringoes; Steven M. Seiler, Pennington, both of NJ (US); R. Michael Lawrence, Yardley, PA (US); James C. Sutton, Jr., Princeton Junction, NJ (US); William A. Slusarchyk, Skillman, NJ (US); Guohua Zhao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/633,751

(22) Filed: Aug. 7, 2000

Related U.S. Application Data

(63) Continuation-in-part of application No. 09/478,632, filed on Jan. 6, 2000.
(60) Provisional application No. 60/119,374, filed on Feb. 9, 1999.

(51) Int. Cl.[7] ..................... A61K 31/55; C07D 223/10; C07D 403/12
(52) U.S. Cl. ..................... 514/212.03; 514/212.08; 540/524; 540/525; 540/527
(58) Field of Search ................. 540/524, 525, 540/527; 514/212.03, 212.08

(56) References Cited

U.S. PATENT DOCUMENTS

| | | | |
|---|---|---|---|
| 5,155,102 A | 10/1992 | Giannessi et al. | 514/212 |
| 5,484,917 A | 1/1996 | Lowe | 540/523 |
| 5,618,811 A | 4/1997 | Lowe | 514/212 |
| 5,672,598 A | 9/1997 | De et al. | 514/212 |
| 5,703,208 A | 12/1997 | Semple et al. | 530/331 |
| 5,932,733 A | 8/1999 | Semple et al. | 546/188 |

FOREIGN PATENT DOCUMENTS

| | | |
|---|---|---|
| EP | 761680 | 3/1997 |
| WO | 93/14113 | 7/1993 |
| WO | 95/35311 | 12/1995 |
| WO | 95/35313 | 12/1995 |
| WO | 96/11940 | 4/1996 |
| WO | 96/29313 | 9/1996 |
| WO | 97/14417 | 4/1997 |
| WO | 97/16425 | 5/1997 |
| WO | WO 97/17363 | * 5/1997 |
| WO | 97/30073 | 8/1997 |
| WO | WO 97/31939 | * 9/1997 |
| WO | 98/12211 | 3/1998 |
| WO | 98/16523 | 4/1998 |
| WO | WO 98/56365 | 12/1998 |
| WO | 00/05208 | 2/2000 |
| WO | WO 00/53264 | 9/2000 |

OTHER PUBLICATIONS

Lowe et al., Bioorg. & Med. Chem. Letters, vol. 4, p. 2877–2882 (1994).

Semple et al., J. Med. Chem., vol. 39, p 4531–4536 (1996).

Freidinger et al., J. Org. Chem., vol. 47, p. 104–109 (1992).

Sreenivasan et al., J. Med. Chem., vol. 36, p. 256–263 (1993).

Skiles et al., Bioorg. & Med. Chem. Letters, vol. 3, p. 773–778 (1993).

Adang et al., Bioorg. & Med. Chem. Letters, vol. 8, p. 3603–3608 (1998).

Angelucci et al., J. Med. Chem., vol. 36, p. 1511–1519 (1993).

\* cited by examiner

*Primary Examiner*—Bruck Kifle
(74) *Attorney, Agent, or Firm*—Burton Rodney

(57) ABSTRACT

Lactam inhibitors are provided which have the structure

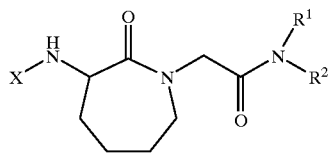

X is

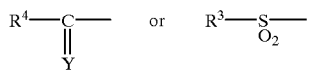

wherein

Y is O or S and $R^4$ is

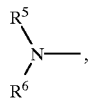

$R^7O-$ or $R^8$ and $R^1$, $R^2$, $R^3$, $R^5$, $R^6$, $R^7$, and $R^8$, are as defined herein. These compounds are inhibitors of Factor Xa and thus are useful as anticoagulants, and are inhibitors of tryptase and thus are useful in treating asthma. Methods for treating cardiovascular diseases associated with thromboses and for treating asthma and related diseases are also provided.

29 Claims, No Drawings

LACTAM COMPOUNDS AND THEIR USE AS INHIBITORS OF SERINE PROTEASES AND METHOD

This application is a continuation-in-part of U.S. application Ser. No. 09/478,632 filed Jan. 6, 2000, which claims priority from provisional application No. 60/119,374 filed Feb. 9, 1999.

FIELD OF THE INVENTION

The present invention relates to lactam inhibitors of serine proteases such as Factor Xa and tryptase, which are useful as anticoagulants in the treatment of cardiovascular diseases associated with thromboses, and as anti-inflammatory agents particularly in the treatment of chronic asthma and related diseases.

BRIEF DESCRIPTION OF THE INVENTION

In accordance with the present invention, novel substituted lactam derivatives are provided which are inhibitors of serine proteases and have the structure I

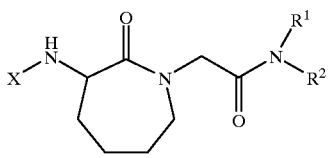

including pharmaceutically acceptable salts thereof and all stereoisomers thereof, and prodrug esters thereof, wherein $R^1$ and $R^2$ are the same or different and are independently selected from hydrogen, alkyl, alkenyl, alkynyl, aryl, aminoalkylaryl, aminocycloalkylalkyl, aminoalkyl, aminoalkylcycloalkyl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, polycycloalkenylalkyl, or $R^1$ and $R^2$ can be taken with the nitrogen to which they are attached to form a cycloheteroalkyl ring; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, aminoalkyl, alkyloxycarbonylaminoalkyl, arylalkyloxycarbonylamino-alkyl, alkylcarbonyl, arylcarbonyl, arylaminocarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

X is

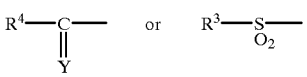

Y is O or S and $R^4$ is

$R^7O$— or $R^8$ $R^3$ is selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, or polycycloalkenylalkyl; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

$R^5$ and $R^6$ are the same or different and are independently selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, polycycloalkenylalkyl, arylcarbonyl, alkylcarbonyl, alkoxycarbonyl, aryloxycarbonyl, arylsulfonyl, or alkylsulfonyl, or $R^5$ and $R^6$ can be taken with the nitrogen to which they are attached to form a cycloheteroalkyl ring; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

R$^7$ and R$^8$ can be the same or different and are independently selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, polycycloalkenyl-alkyl, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl; with the proviso that where in the formula I compounds

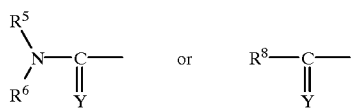

and (1) R$^1$ and R$^2$ are independently alkyl, cycloalkyl, alkenyl, phenyl, benzyl, cyanoalkyl, alkoxycarbonylalkyl, or phenyl mono- or disubstituted with lower alkyl, cyano, hydroxy, dialkylamino, alkoxy, benzyloxy, alkylamino, alkoxycarbonyl, pyrrolidino, morpholino, halogen, alkyl substituted with one or more fluorines, then Y is S;

(2) where R$^1$ and R$^2$ are alkyl, then Y is S; and (3) where one of R$^1$ and R$^2$ is alkyl and Y is O, then the other is alkynyl, heteroaryl, heteroarylalkyl, cycloalkenyl, cycloheteroalkyl, heteroaryloxy, cycloalkenylalkyl, polycycloalkenyl, polycycloalkenylalkyl or R$^1$ and R$^2$ can be taken with the nitrogen to which they are attached to form a cycloheteroalkyl ring, all optionally substituted through available carbon atoms with 1, 2, 3 or 4 substituents as defined for R$^1$ and R$^2$.

Thus, the compounds of formula I of the invention can have the following structural formulae:

IA

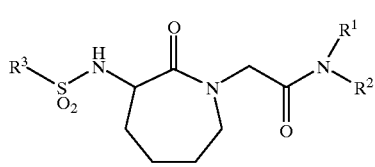

IB

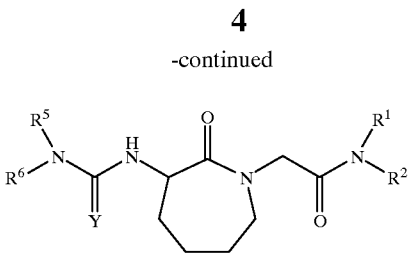

IC

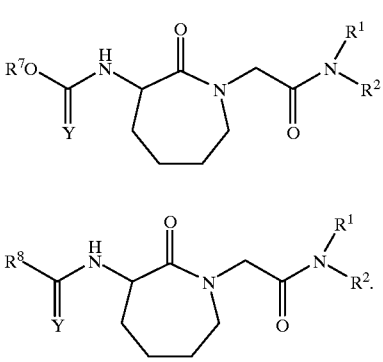

ID

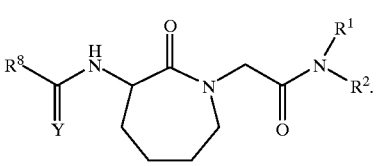

Preferred compounds are compounds of formula IB wherein R$^1$ and R$^2$ together with the nitrogen to which they are attached form a cycloheteroalkyl ring, preferably a pyrrolidinyl ring, Y is S, one of R$^5$ and R$^6$ is hydrogen and the other of R$^5$ and R$^6$ is aryl, alkylaryl or alkoxyaryl such as phenyl, 3-methylphenyl or 3-methoxyphenyl, 4-cyanophenyl, 3-fluorophenyl, 3-chlorophenyl, 4-chlorophenyl, 4-methoxyphenyl, 3-chloro-4-methylphenyl, 3,5-dichlorophenyl, 3-iodophenyl, 3,5-dimethylphenyl or naphthyl.

Also preferred are compounds of formula ID wherein one of R$^1$ and R$^2$ is hydrogen and Y is O.

In addition, preferred are compounds of formula ID wherein one of R$^1$ and R$^2$ is aminoalkylaryl such as

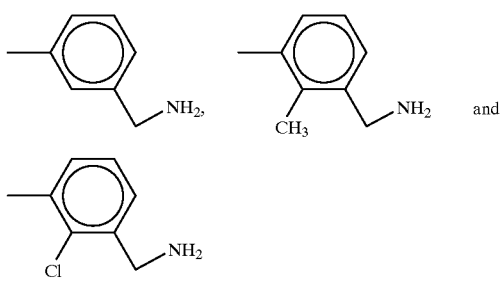

and aminocycloalkylalkyl, such as

and y is O.

Preferred compounds of the invention have the structures
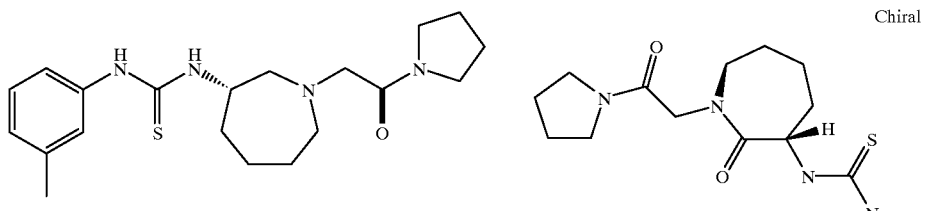
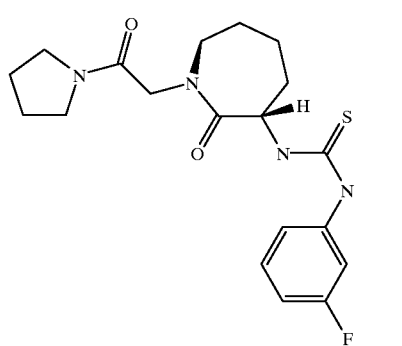
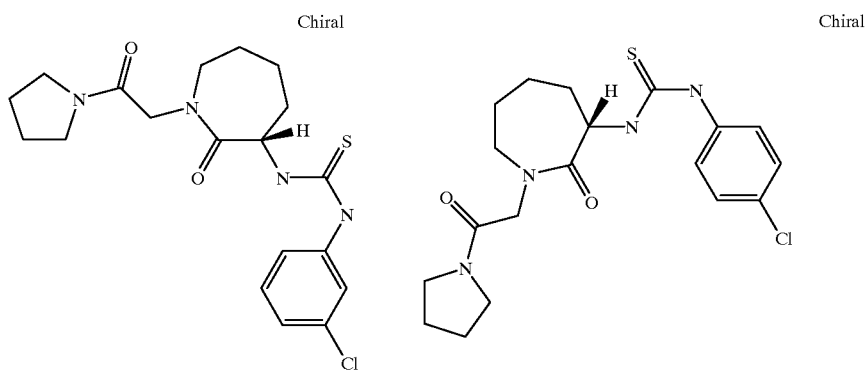
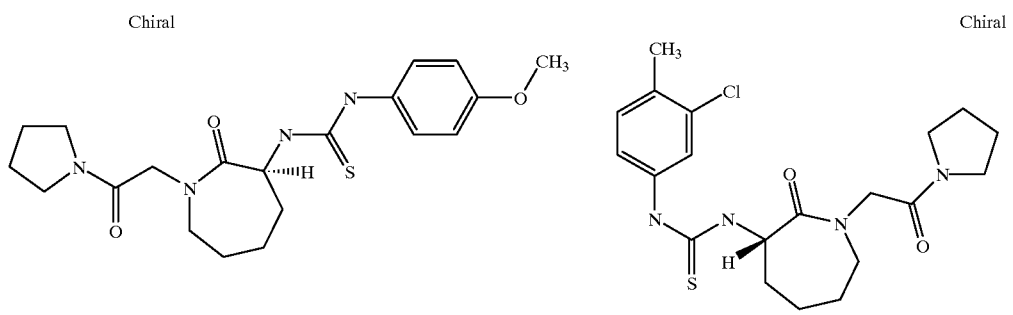
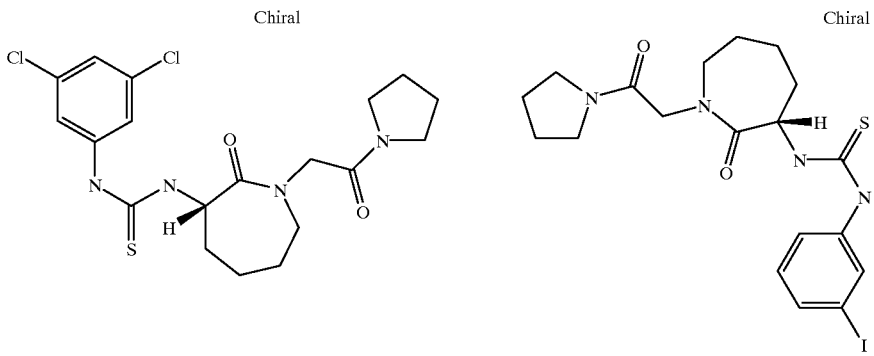

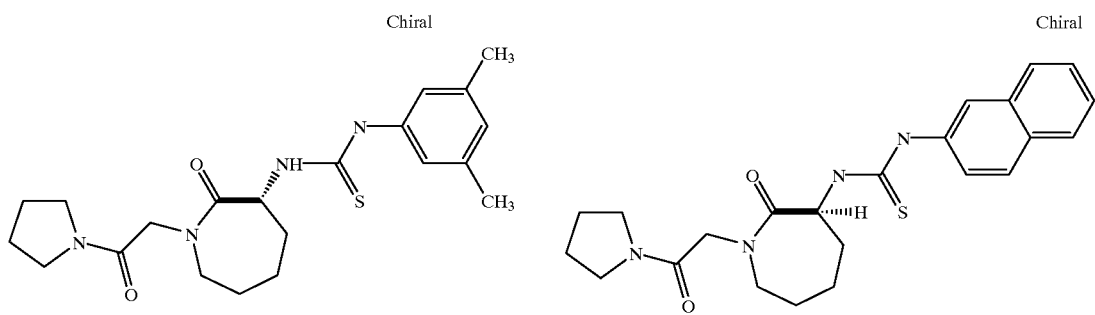
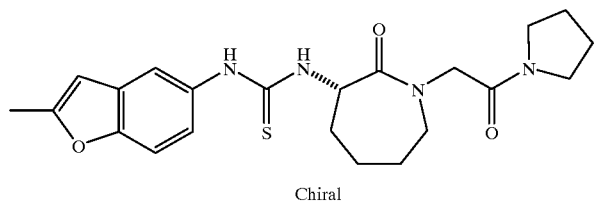
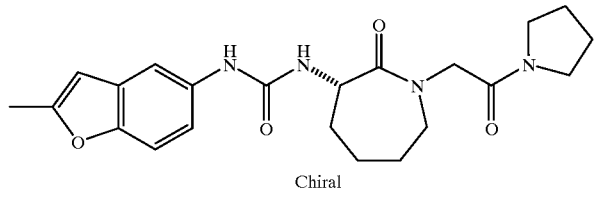
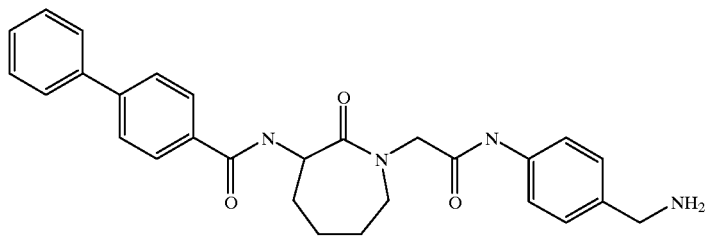
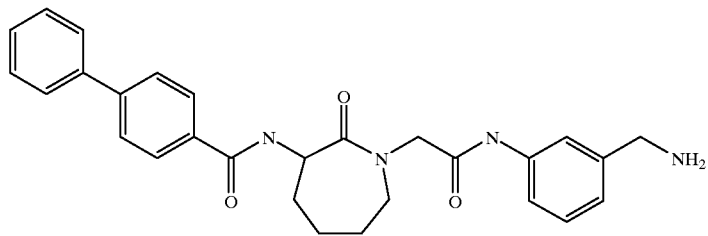

-continued
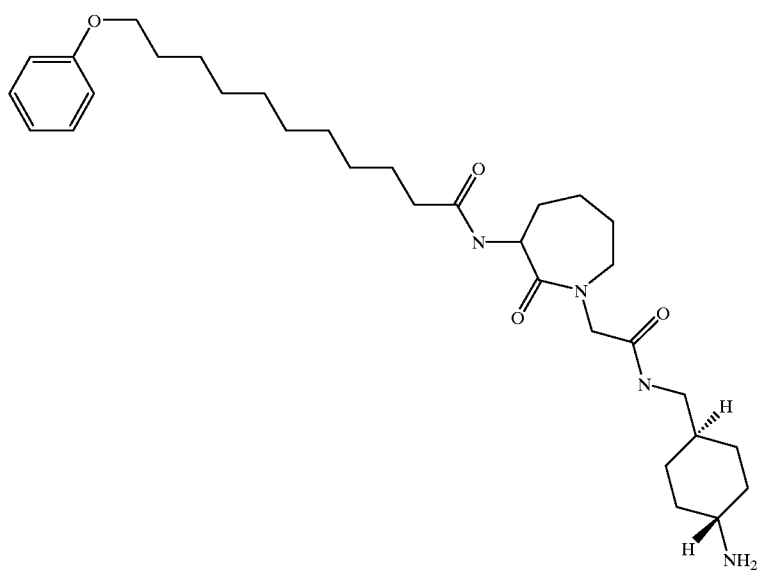
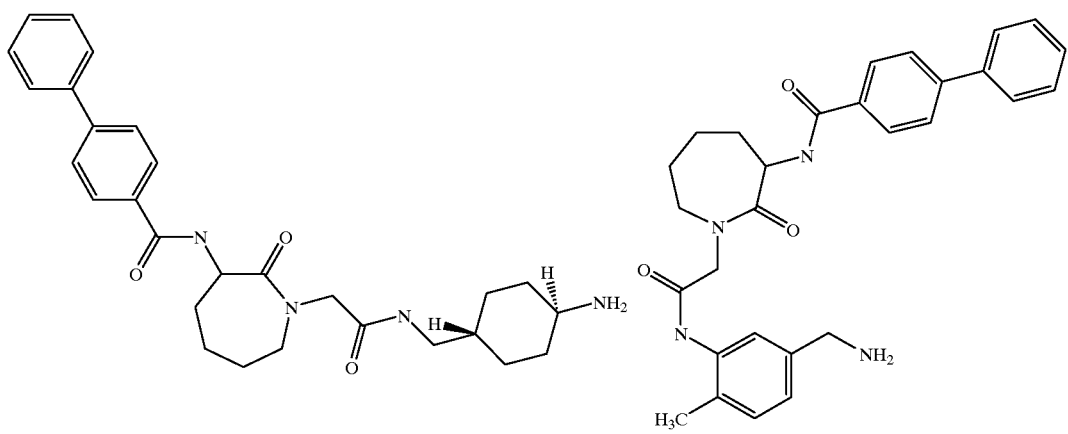
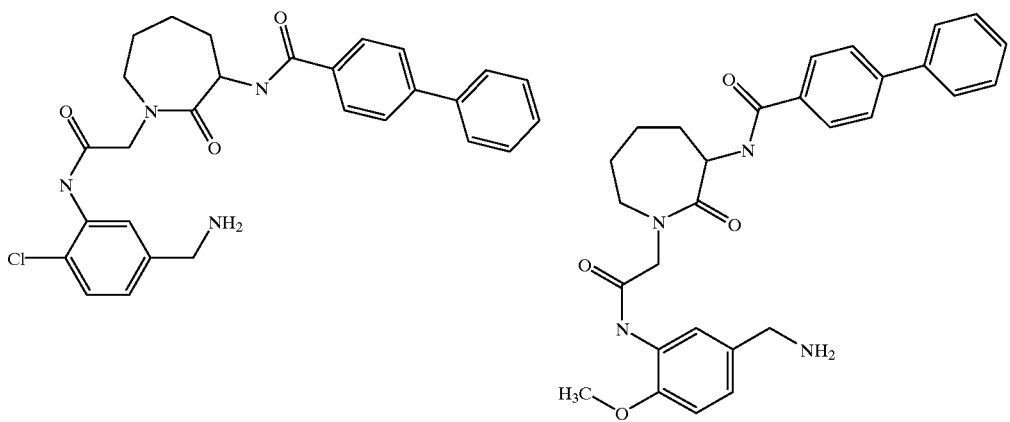
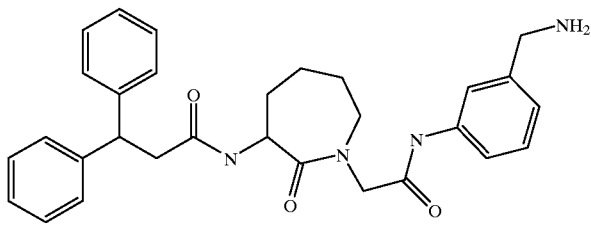

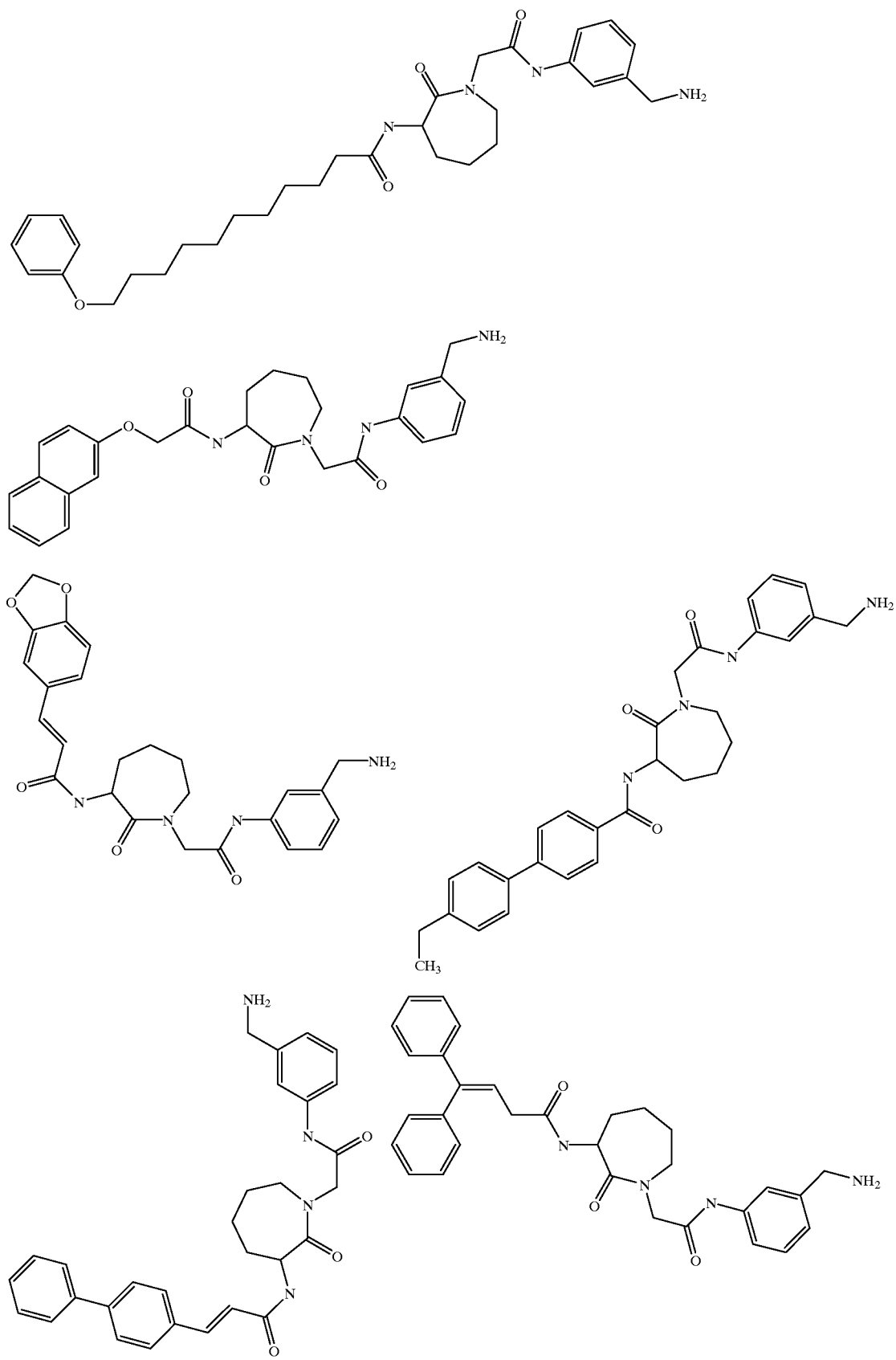

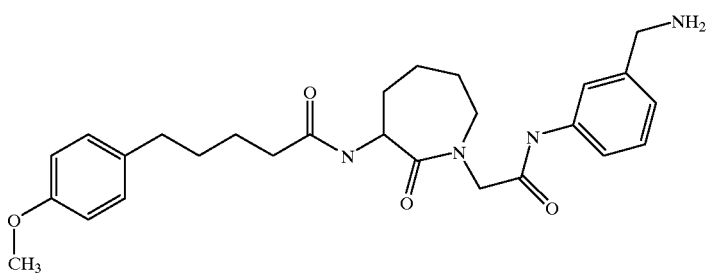
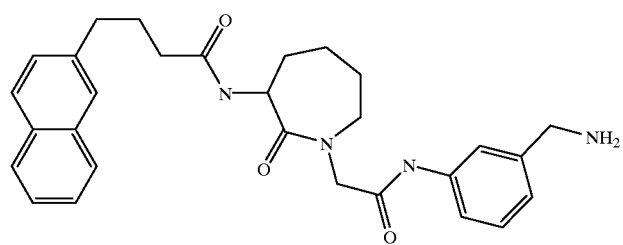
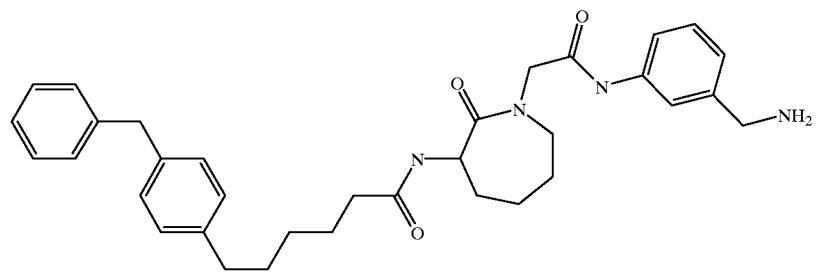
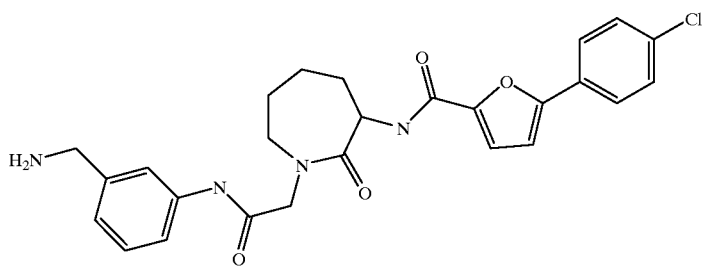
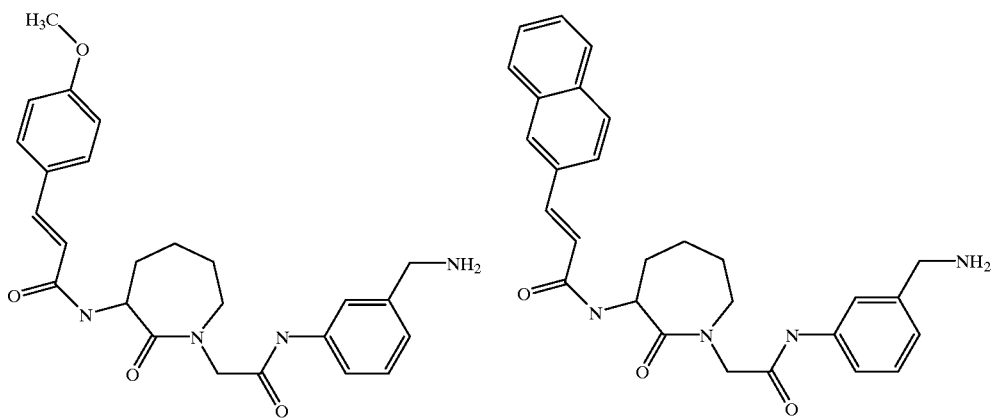

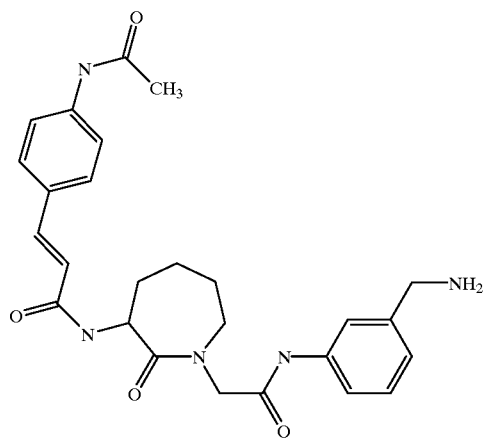
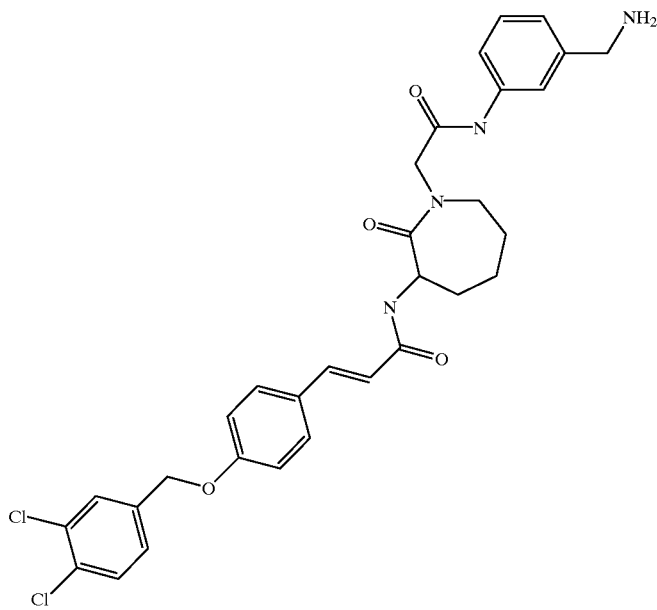
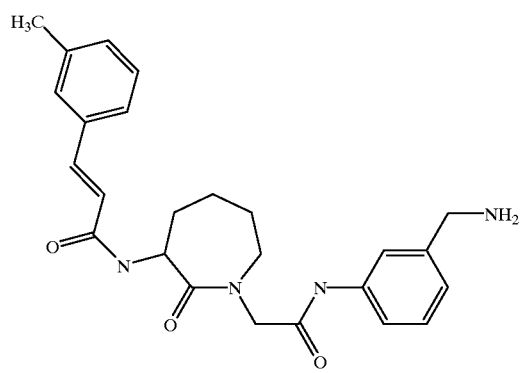
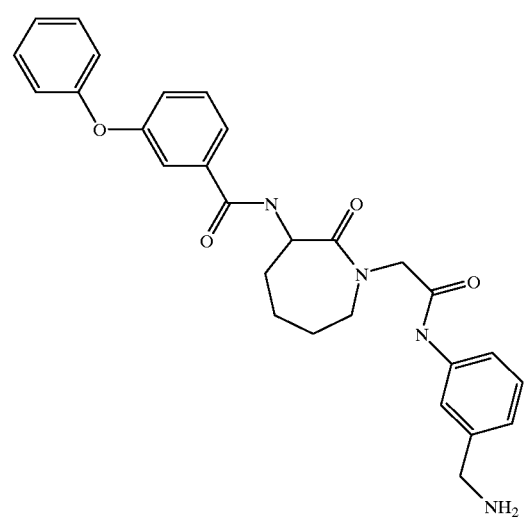
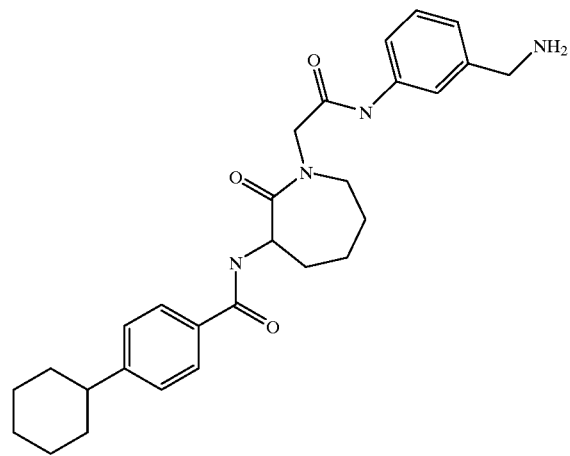
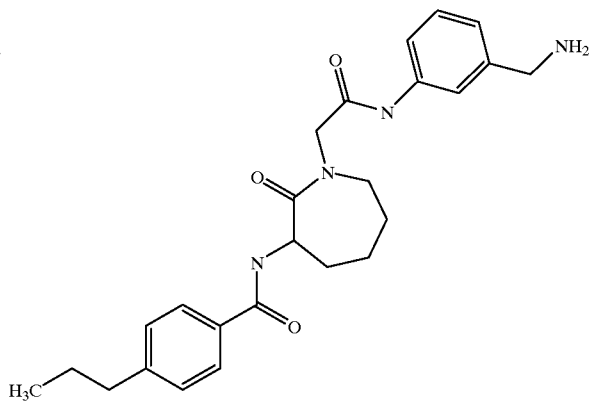

-continued
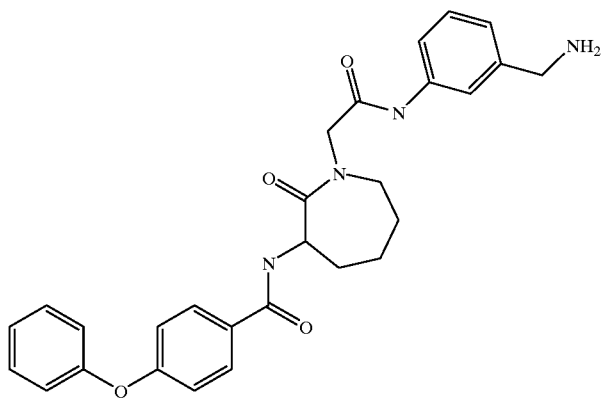
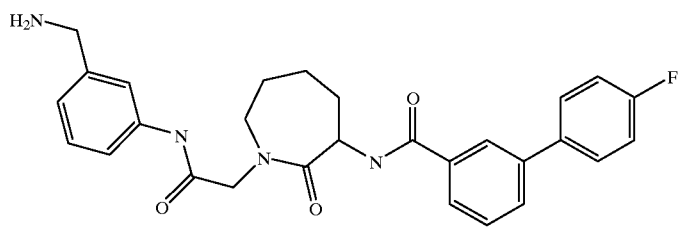
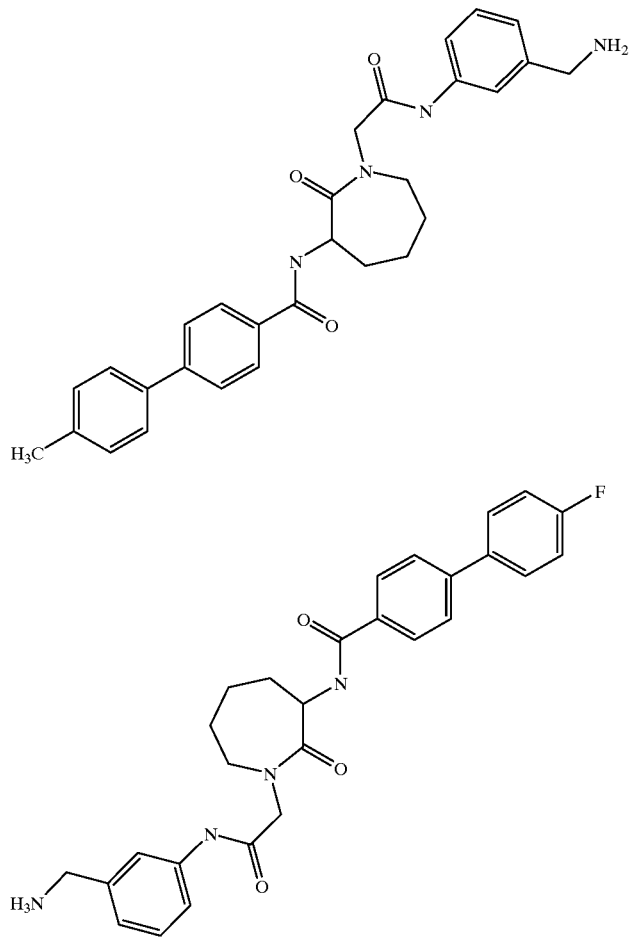

-continued

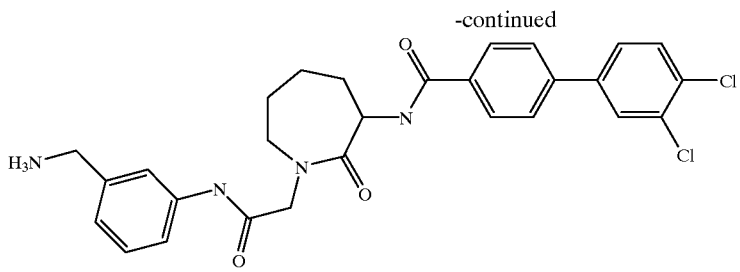

It will be appreciated that in compounds illustrated above and throughout, where a nitrogen is included with an apparent open valence, the nitrogen includes a hydrogen atom.

In addition, in accordance with the present invention, a method for treating and/or preventing medical conditions related to tryptase (such as asthma, chronic asthma or allergic rhinitis) or Factor Xa (such as thromboses, coronary artery disease or cerebrovascular disease) is provided, wherein a compound of formula I is administered in a therapeutically effective amount which inhibits Factor Xa or tryptase.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons (in the case of alkyl or alk), preferably 1 to 20 carbons, more preferably 1 to 12 carbons (in the case of lower alkyl), in the normal chain,such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be any of the $R^1$ or the $R^1$ substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl, cyclooctyl, cyclodecyl and cyclododecyl, cyclohexenyl,

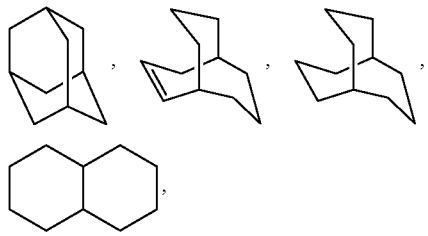

any of which groups may be optionally substituted with 1 to 4 substituents which may be any of the $R^1$ groups, or the $R^1$ substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloalkyl, cycloheteroalkyl, cycloheteroalkylalkyl, aryl, aminoalkyl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl or any of the $R^1$ groups or the $R^1$ substituents set out herein.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be independently substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the $R^1$ groups or $R^1$ substituents thereof as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio or any of the $R^1$ groups, or the $R^1$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^1$ groups, or the $R^1$ substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_p$ (where, p is 1 to 8, preferably 1 to 5) (which may include alkylene, alkenylene or alkynylene groups) as defined herein, may optionally include 1, 2, or 3 substituents which include any of the $R^1$ groups, or the $R^1$ substituents set out herein.

Examples of alkylene, alkenylene and alkynylene include

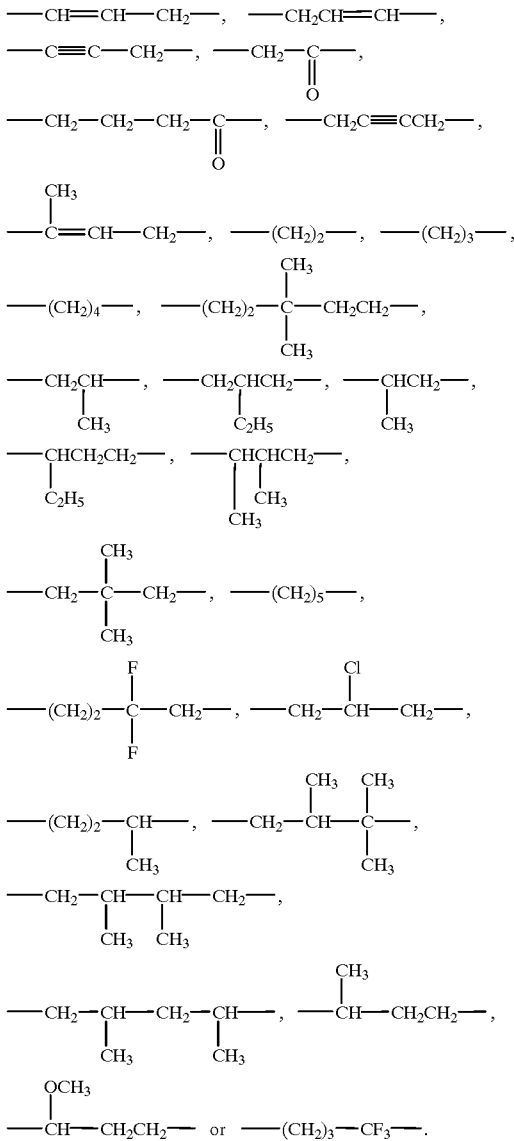

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl", as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

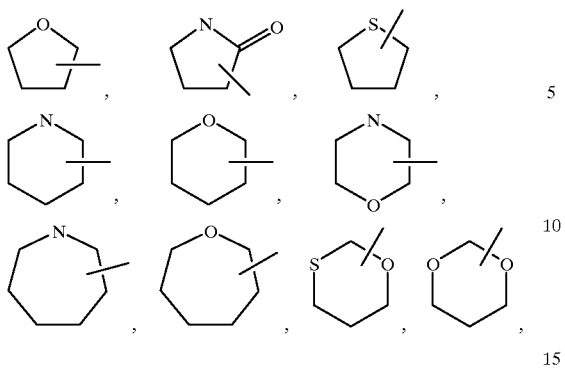

and the like. The above groups may include 1 to 4 substituents such as alkyl, halo, oxo and/or any of of the $R^1$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the $R^1$ groups or the $R^1$ substituents set out above. Examples of heteroaryl groups include the following:

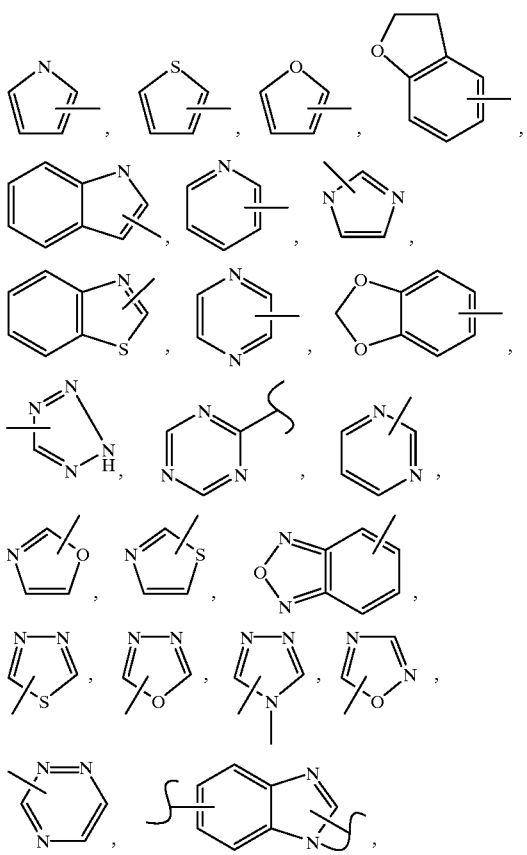

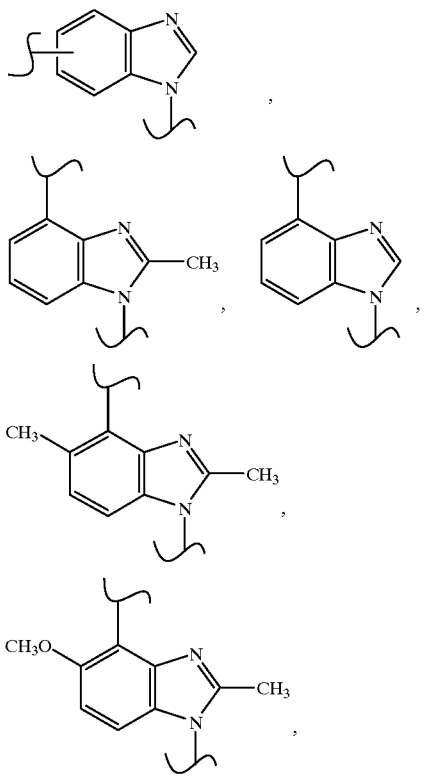

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $-(CH_2)_p-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $(C_1-C_4)$-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

It should be understood that the present invention includes prodrug forms of the compounds of formula I such as alkylesters of acids or any known prodrugs for lactam derivatives.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

Compounds of formula I of the invention can be prepared from the corresponding amine 1 by using the sequence of steps outlined in Scheme I set out below.

Reaction Scheme I

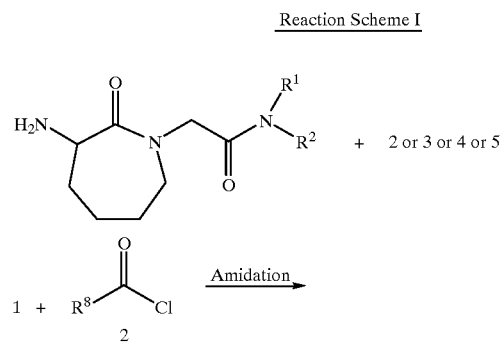

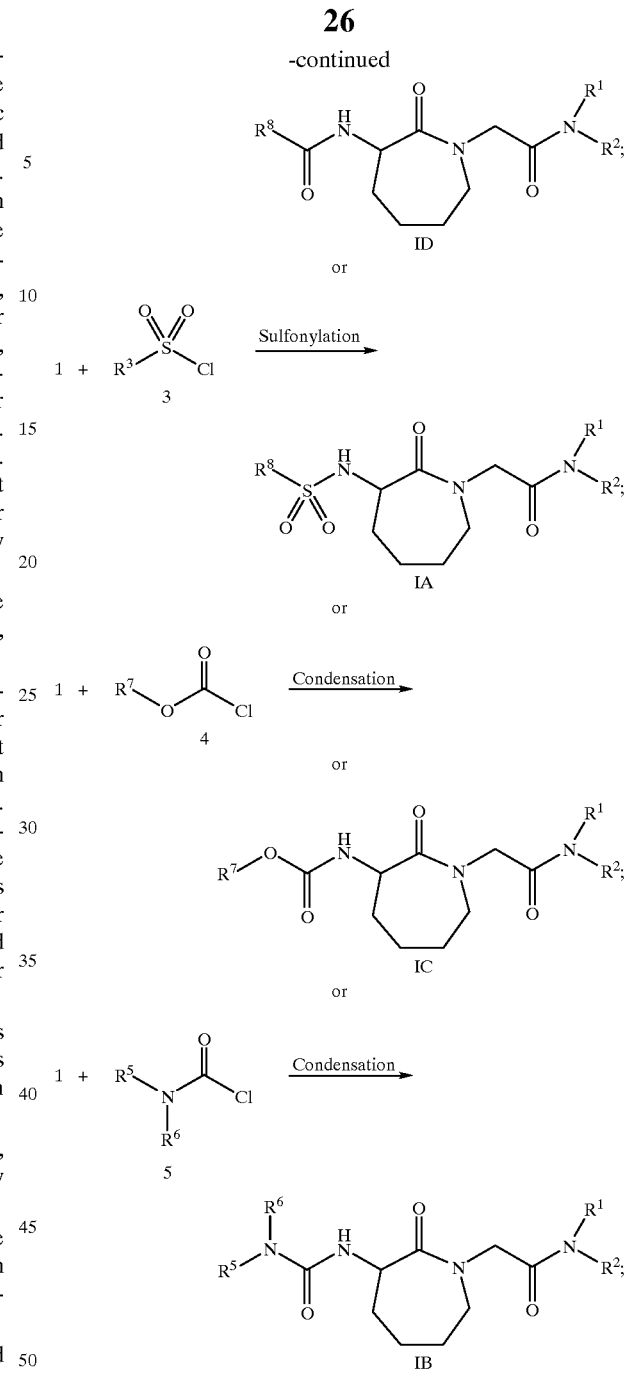

Reaction of amine 1 in an inert organic solvent such as dichloromethane, chloroform or tetrahydrofuran with reactant acid chloride 2, sulfonyl chloride 3, chloroformate 4 or carbamoylchloride 5, employing a molar ratio of reactant:amine 1 within the range from about 5:1 to about 1:5, optionally in the presence of an acid scavenger such as triethylamine, diisopropylethylamine, pyridine, or polyvinylpyridine, forms compounds ID, IA, IC or IB of the invention.

Starting compound 1 can be prepared by methods known in the art as outlined in Reaction Scheme IA below.

Reaction Scheme IA

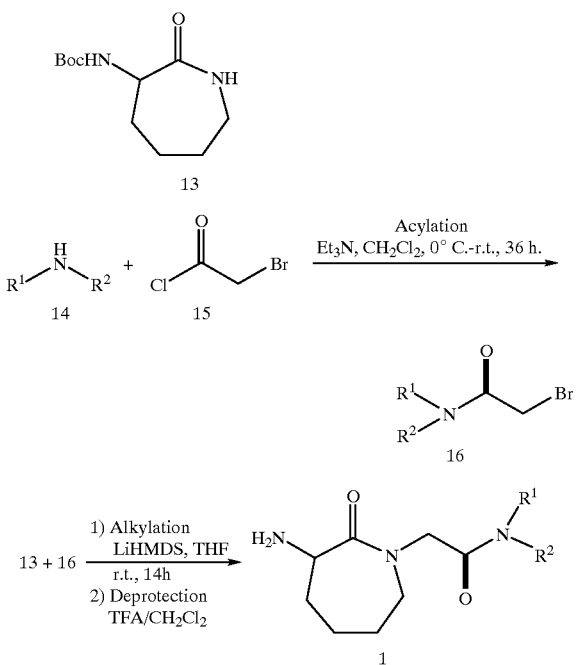

Compound 1 is a novel compound provided that $R^1$ and $R^2$ are as defined herein, but excludes alkyl, alkenyl, aryl, arylalkyl, cycloalkyl or polycycloalkyl.

Compounds of formula I of the invention wherein

X is

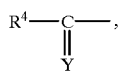

Y is O and $R^4$ is

that is

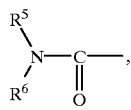

can be prepared from the corresponding acid 6 by using the sequence of steps outlined in Scheme II (Procedures A and B) set out below.

Reaction Scheme II

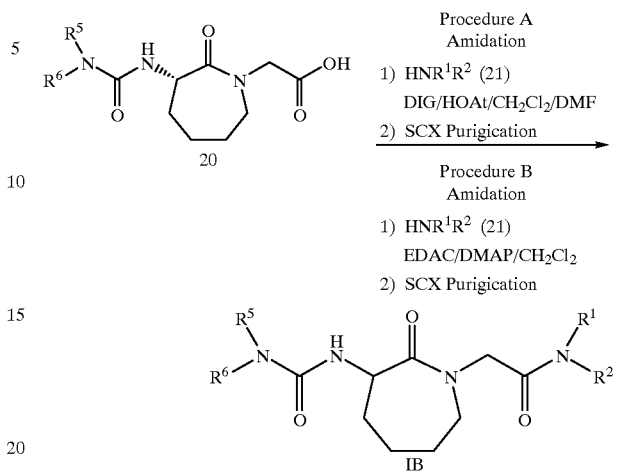

Procedure A

For amines where $R^1$ and/or $R^2$ contain additional basic nitrogens.

Procedure B

For amines where $R^1$ and/or $R^2$ contain no additional basic nitrogens.

In Procedure A (for amines where $R^1$ and/or $R^2$ contain additional basic nitrogens), a mixture of a solution of amine 21 in an inert organic solvent such as THF, methylenechloride or chloroform, a carbodiimide such as diisopropylcarbodiimide (DIC) and 7-aza-1-hydroxy-benzotriazole (HOAt) is reacted with acid 20, employing a molar ratio of amine 21:acid 20 within the range from about 5:1 to about 1:5, preferably at about 1:1.1, to form a reaction mixture which is purified via an SCX column to separate out compound IB of the invention.

The DIC will be employed in a molar ratio to acid 20 within the range from about 5:1 to about 1:5, preferably at about 1.6:1, and the HOAt will be employed in a molar ratio acid 20 within the range from about 5:1 to about 1:5, preferably at about 1.6:1.

In Procedure B (for amines where $R^1$ and/or $R^2$ contain no additional basic nitrogens) a mixture of a solution of amine 21 in an inert organic solvent such as THF, methylenechloride or chloroform, ethyldimethylaminopropylcarbodiimide (EDAC) and dimethylaminopyridine (DMAP) with acid 20, employing a molar ratio of amine 21:acid 20 within the range from about 5:1 to about 1:5, preferably at about 1.5:1, to form a reaction mixture which is purified via a SCX column to separate out compound IB of the invention.

The EDAC will be employed in a molar ratio to acid 20 within the range from about 5:1 to about 1.5, preferably at about 1.5:1, and the DMAP will be employed in a molar ratio to acid 20 within the range from about 5:1 to about 1:5, preferably at about 1.5:1.

Starting compound 20 can be prepared by methods known in the art as outlined in Reaction Scheme IIA.

Reaction Scheme IIA

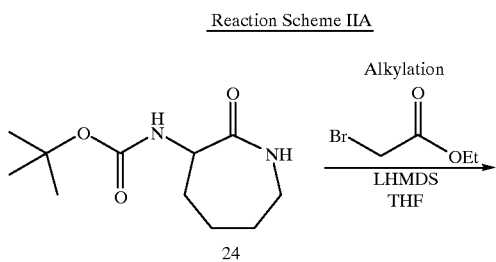

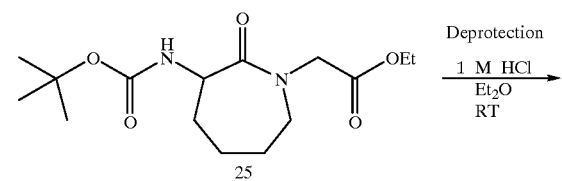

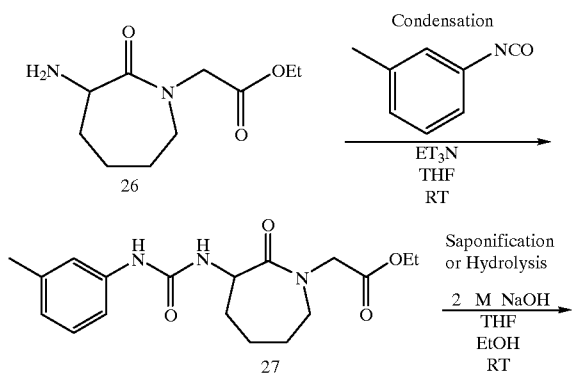

Compounds of formula I of the invention wherein

X is

R⁴—C—,
  ‖
  Y

Y is O or S, and R⁴ is

R⁵
 \
  N—,
 /
R⁶ that is

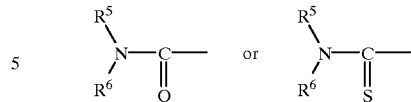

can be prepared from the corresponding amine 1 by using the sequence of steps outlined in Scheme III set out below.

Reaction Scheme III

1. R⁵NCO or R⁵NCS
   (31)      (30)
   CH₂Cl₂, RT, 6h.
2. aminomethyl-polystyrene (32) resin, 16h., RT

IB' or

IB"

Reaction of amine 1 (in an inert organic solvent such as dichloromethane, chloroform or tetrahydrofuran) with reactant 30 or 31 employing a molar ratio of 30 or 31:amine 1 within the range of from about 5:1 to about 1:5, followed by treatment with aminomethylpolystyrene (32), affords the compound of the invention IB' or IB".

Compounds of formula I of the invention wherein

O
           ‖
X=    R₈—C— can be prepared from the corresponding acid 29

29 using the sequence of steps outlined in Scheme IV set out below:

Reaction Scheme IV

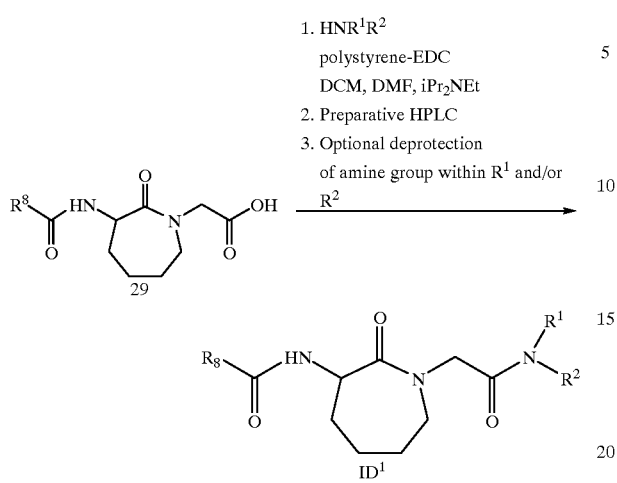

$R^1$ and/or $R^2$ can be neutral or may contain a basic nitrogen. When $R^1$ and/or $R^2$ contains a basic nitrogen, the nitrogen may optionally be protected, for example with a BOC group or Cbz group. The protecting group can then be removed, for example, by treating with TFA in methylene chloride for removal of a BOC or Cbz protecting group.

Starting compound 29 can be prepared by methods as outlined in Reaction Scheme IVa

Reaction Scheme IVa

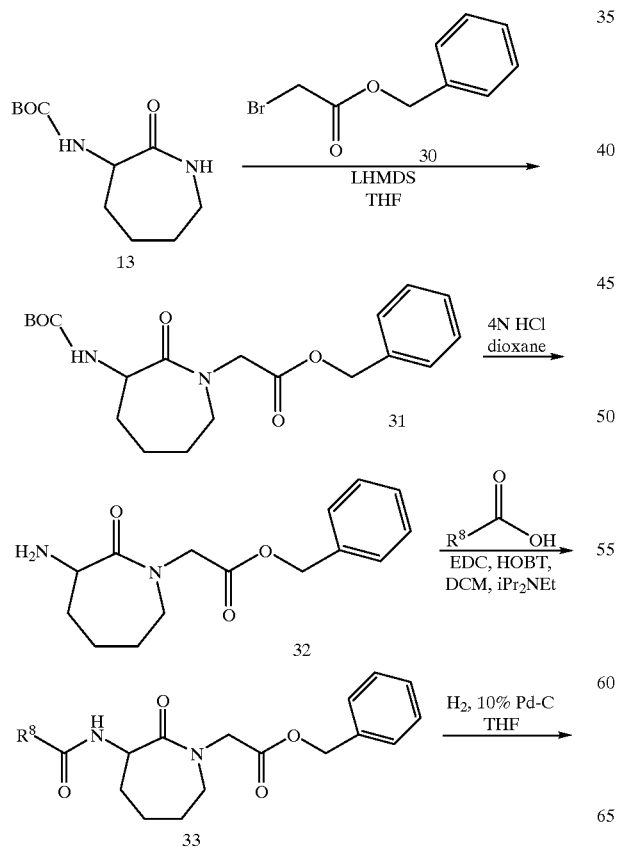

Alternatively, compounds of formula I of the invention wherein

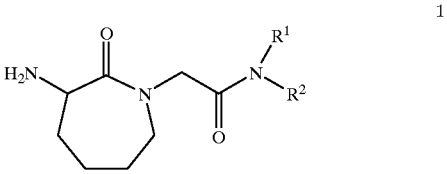

can be prepared from the corresponding amine 1

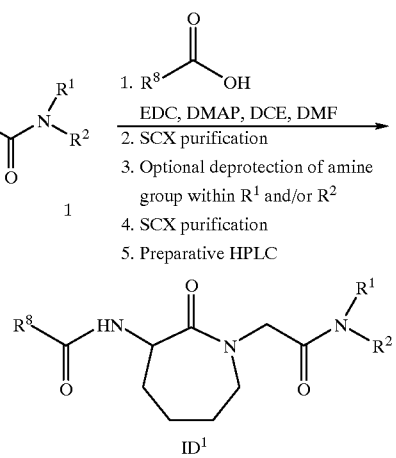

using the sequence of steps outline in Scheme V set out below.

Reaction Scheme V $R^1$ and/or $R^2$ can be neutral or may contain a basic nitrogen. When $R^1$ and/or $R^2$ in starting amine 1 contains a basic nitrogen, the nitrogen may optionally be protected, for example, with a BOC group. The protecting group can then be removed, for example, by treating with TFA in methylene chloride for removal of a BOC protecting group, as outlined below in Reaction Scheme VA.

Reaction Scheme VA

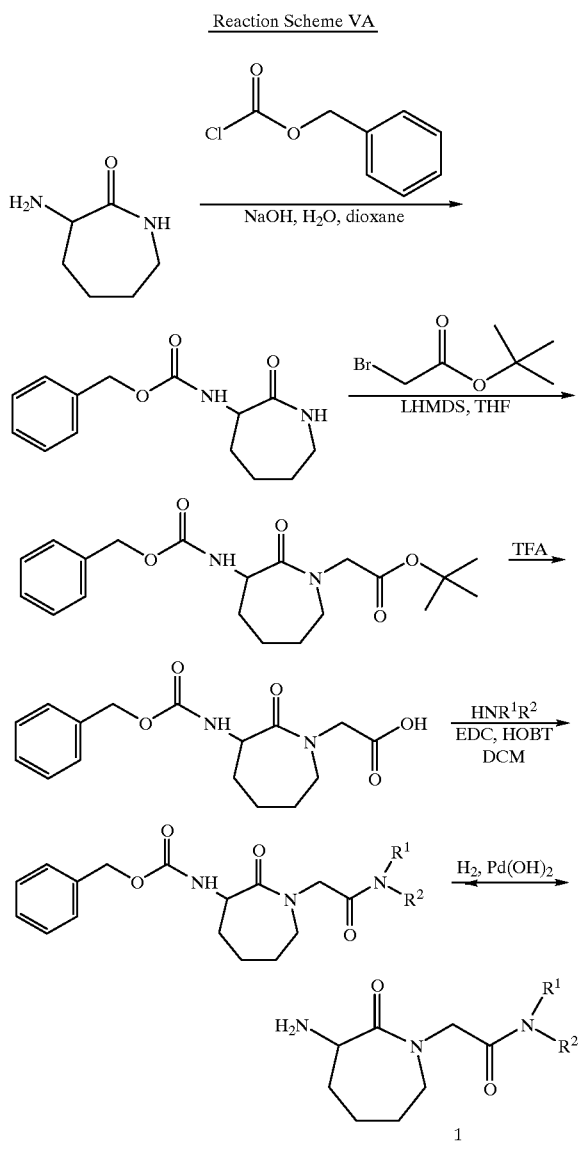

The compounds of the present invention, preferably where $R^1$ and $R^2$ are other than hydrogen, are inhibitors of the activated coagulation serine protease known as Factor Xa and thus are useful for the treatment or prophylaxis of those processes which involve the production and/or action of Factor Xa.

The Factor Xa activity was confirmed using the following assay.

Assay for FXa Inhibitory Activity

Human FXa or bovine FXa enzymatic activity was measured in a buffer containing 0.145 M NaCl, 0.005 M KCl, 1 mg/ml Polyethylene Glycol (PEG-8000), 0.030 M HEPES (pH 7.4) using 96-well microtiter plates. The enzyme was incubated with the inhibitor at room temperature for three minutes prior to starting the reaction with 100 μM S-2222 (phenyl-Ile-Glu-Gly-Arg-pNA, $K_m$=137 μM). Time-dependent optical density change was followed at 405 nm using a kinetic microplate reader (Molecular Devices UVmax) at room temperature. Enzyme activity in the presence of inhibitor was expressed as fraction of a DMSO control and curve fit to the equation: activity=control activity/(1+[I]/$IC_{50}$) using Excel Fit. The $IC_{50}$ value is that concentration causing half-maximal inhibition.

The Factor Xa inhibiting compounds of the invention are useful in the treatment and/or prevention of thrombotic events associated with cardiovascular disease including, but not limited to, coronary artery and cerebrovascular disease. This includes a number of thrombotic and prothrombotic states in which the coagulation cascade is activated which include, but are not limited to, formation of atherosclerotic plaques, venous or arterial thrombosis, coagulation syndromes, ischemia and angina (stable and unstable), deep vein thrombosis (DVT), disseminated intravascular coagulopathy, Kasabach-Merritt syndrome, pulmonary embolism, myocardial infarction, cerebral infarction, cerebral thrombosis, atrial fibrillation, cerebral embolism, thromboembolic complications of surgery (such as hip replacement, introduction of artificial heart valves and endarterectomy) and peripheral arterial occlusion. The compounds of the invention are also useful as inhibitors of blood coagulation such as during the preparation, storage and fractionation of whole blood.

The present compounds may also be useful in maintaining whole and fractionated blood in the fluid phase such as required for analytical and biological testing. Examples include, but are not limited to, ex vivo platelet and other cell function studies, bioanalytical procedures and quantitation of blood-containing components.

In addition, the compounds of the present invention may be useful to prevent restenosis following arterial injury induced by endogenous (rupture of an atherosclerotic plaque) or exogenous (invasive cardiological procedure such as vessel wall injury resulting from angioplasty) events.

The compounds of the present invention may also be used as an anticoagulant in extracorpeal blood circuits, such as those necessary in dialysis and surgery (such as coronary artery bypass surgery).

In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation.

The compounds of the present invention may be useful for the treatment of heparin-intolerant patients, including those with congenital and acquired antithrombin III deficiencies, heparin-induced thrombocytopenia, and those with high levels of polymorphonuclear granulocyte elastase.

The compounds of the present invention may also be useful for the treatment and/or prevention of inflammatory diseases and the treatment and/or prevention of septic shock and vascular damage due to bacterial and/or viral infections.

The compounds of the present invention may also be useful in the treatment and/or prevention of malignancies, prevention of metastases, treatment and/or prevention of prothrombotic complications of cancer, and as an adjunct to chemotherapy.

Additionally the compounds of the invention may be useful for treating and/or preventing motor neuron diseases such as amyotrophic lateral sclerosis, progressive muscular atrophy and primary lateral sclerosis.

The novel compounds of formula I of the invention possess tryptase inhibition activity. This activity was confirmed using either isolated human skin tryptase or recombinant human tryptase prepared from the human recombinant beta-protryptase expressed by baculovirus in insect cells. The expressed beta-protryptase was purified using sequential immobilized heparin affinity resin followed by an immunoaffinity column using an anti-tryptase monoclonal antibody. The protryptase was activated by auto-catalytic removal of the N-terminal in the presence of dextran sulfate followed by dipeptidyl peptidase I (DPPI) removal of the two N-terminal amino acids to give the mature active enzyme (Sakai et al, J. Clin. Invest., 97, pages 988–995, 1996). Essentially equivalent results were obtained using isolated native enzyme or the activated expressed enzyme. The tryptase enzyme was maintained in 2M sodium chloride, 10 nM 4-morpholine-propanesulfonic acid, pH 6.8.

The assay procedure employed a 96 well microplate. To each well of the microplate (Nunc MaxiSorp), 250 µl of assay buffer [containing low molecular weight heparin and tris (hydroxymethyl)aminomethane] was added followed by 2.0 µl of the test compound in dimethylsulfoxide. The substrate (10 µl) was then added to each well to give a final concentration of either 370 µM benzoyl-arginine-p-nitroaniline (BAPNA) or 100 µM benzyloxycarbonyl-glycine-proline-arginine-p-nitroaniline (CBz-Gly-Pro-Arg-pNA). Similar data was obtained using either substrate. The microplate was then shaken on a platform vortex mixer at a settinag of 800 (Sarstedt TSP.-2). After a total of three minutes incubation, 10 µl of the working stock solution of tryptase (6.1 mM final tryptase concentration for use with BAPNA or 0.74 nM for use with CBz-Gly-Pro-Arg-pNA) was added to each well. The microplate was vortexed again for one minute and then incubated without shaking at room temperature for an additional 2 minutes. After this time the microplate was read on a microplate reader (Molecular Devices UV max) in the kinetic mode (405 nm wavelength) over twenty minutes at room temperature. To determine the compound concentration that inhibited half of the enzyme activity ($IC_{50}$), the fraction of control activity (FCA) was plotted as a function of the inhibitor concentration and curve to fit $FCA/(1[I]/IC_{50})$. The $IC_{50}$ for each compound was determined 2–4 times and the obtained values were averaged.

As a result of this tryptase activity, the compounds of formula I as well as a pharmaceutically acceptable salt thereof, are useful as anti-inflammatory agents particularly in the treatment and/or prevention of chronic asthma and may also be useful in treating and/or preventing allergic rhinitis, inflammatory bowel disease, psoriasis, conjunctivitis, atopic dermatitis, rheumatoid arthritis, osteoarthritis, and other chronic inflammatory joint diseases, or diseases of joint cartilage destruction. Additionally, these compounds may be useful in treating or preventing myocardial infarction, stroke, angina and other consequences of atherosclerotic plaque rupture. Additionally, these compounds may be useful for treating or preventing diabetic retinopathy, tumor growth and other consequences of angiogenosis. Additionally, these compounds may be useful for treating or preventing fibrotic conditions, for example, fibrosis, scleroderma, pulmonary fibrosis, liver cirrhosis, myocardial fibrosis, neurofibromas and hypertrophic scars. Additionally these compounds may be useful for treating and/or preventing diseases involving angiogenesis including, but not limited to, cancer.

The compounds of the present invention may also inhibit other serine proteases, for example, thrombin, Factor VIIa, Factor XIa, urokinase-type plasminogen activator (urokinase), and/or trypsin. As a result, these compounds are or may be useful as described above for inhibition of FXa. Also as a result, these compounds may additionally be useful as angiogenesis inhibitors in the treatment and/or prevention of cancer, and in the treatment and/or prevention of pancreatitis.

The compounds of the present invention may also be used in combination with other antithrombotic or anticoagulant drugs such as thrombin inhibitors, platelet aggregation inhibitors such as clopidogrel, ticlopidine or CS-747, warfarin, low molecular weight heparins, (such as Lovenox), GPIIb blockers/GPIIIa blockers, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, aspirin, hypolipidemic agents (such as HMG-CoA reductase inhibitors for example pravastatin, simvastatin, atorvastatin, fluvastatin, cerivastatin, AZ4522, itavastatin (Nissan/Kowa), compounds disclosed in U.S. provisional applications No. 60/211,594 filed Jun. 15, 2000, and No. 60/211,595 filed Jun. 15, 2000, microsomal triglyceride transport protein inhibitors such as disclosed in U.S. Pat. Nos. 5,739,135, 5,712,279 and 5,760,246), antihypertensive agents, (such as angiotensin converting enzyme inhibitors, for example, captopril, lisinopril or fosinopril, angiotensin II receptor antagonists, for example, irbesartan, losartan or valsartan, and ACE/NEP inhibitors, for example omapatrilat and gemopatrilat), β-blockers (such as propranolol, nadolol and carvedilol), PDE inhibitors in combination with aspirin, ifetroban, picotamide, ketanserin or clopidogrel and the like.

The compounds of the present invention may also be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like. The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

Compounds of the present invention are also useful in combination with anti-arrhythmic agents such as for atrial fibrillation, for example, amiodarone or dofetilide.

The compounds of the present invention may also be used in combination with β-adrenergic agonists such as albuterol, terbutaline, formoterol, salmeterol, bitolterol, pilbuterol, or fenoterol, as well as with anticholinergics such as ipratropium bromide, anti-inflammatory cortiocosteroids such as beclomethasone, triamcinolone, budesonide, fluticasone, flunisolide or dexamethasone, and anti-inflammatory agents such as cromolyn, nedocromil, theophylline, zileuton, zafirlukast, monteleukast and pranleukast.

The compounds of the invention can be administered orally or parenterally such as subcutaneously or intravenously, as well as by inhalation and nasal application, rectally, transdermally, or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds of formulas I, IA., IB, IC and ID. They may be compounded in conventional matter with a physiologically acceptable vehicle or carrier, excipient, binder, preservative, stabilizer, flavor, etc., as called for by accepted pharmaceutical practice.

The following abbreviations are employed hereinbefore and in the Examples:

Ph=phenyl

Bn=benzyl t-Bu=tertiary butyl

Me=methyl

Et=ethyl

TMS=trimethylsilyl $TMSN_3$=trimethylsilyl azide

TBS=tert-butyldimethylsilyl

FMOC=fluorenylmethoxycarbonyl

Boc=tert-butoxycarbonyl

Cbz=carbobenzyloxy or carbobenzoxy or benzyloxycarbonyl

THF=tetrahydrofuran $Et_2O$ diethyl ether hex=hexanes

EtOAc=ethyl acetate

DMF=dimethyl formamide

MeOH=methanol

EtOH=ethanol i-PrOH=isopropanol

DMSO=dimethyl sulfoxide

DME=1,2 dimethoxyethane

EDC or DCE=1,2 dichloroethane

HMPA=hexamethyl phosphoric triamide

HOAc or AcOH=acetic acid

TFA=trifluoroacetic acid i-$Pr_2$NEt=diisopropylethylamine $Et_3N$=triethylamine NMM=N-methyl morpholine DMAP=4-dimethylaminopyridine $NaBH_4$=sodium borohydride $NaBH(OAc)_3$=sodium triacetoxyborohydride DIBALH=diisobutyl aluminum hydride DCM=4-(dicyanomethylene)-2-methyl-6-(4-dimethylamino-styryl)-4H-pyran $LiAlH_4$=lithium aluminum hydride n-BuLi=n-butyllithium Pd/C=palladium on carbon $PtO_2$=platinum oxide KOH=potassium hydroxide NaOH=sodium hydroxide LiOH=lithium hydroxide $K_2CO_3$ =potassium carbonate $NaHCO_3$=sodium bicarbonate DBU=1,8-diazabicyclo [5.4.0] undec-7-ene EDC (or EDC.HCl) or EDCI (or EDCI.HCl) or EDAC= 3-ethyl-3'-(dimethylamino)propyl-carbodiimide hydrochloride (or 1-(3-dimethylaminopropyl)-3-ethylcarbodiimide hydrochloride)

HOBT or HOBT.$H_2O$=1-hydroxybenzotriazole hydrate

HOAT=1-Hydroxy-7-azabenzotriazole

BOP reagent=benzotriazol-1-yloxy-tris (dimethylamino) phosphonium hexafluorophosphate $NaN(TMS)_2$=sodium hexamethyldisilazide or sodium bis (trimethylsilyl)amide $Ph_3P$=triphenylphosphine $Pd(OAc)_2$=Palladium acetate $(Ph_3P)_4Pd°$=tetrakis triphenylphosphine palladium DEAD=diethyl azodicarboxylate DIAD=diisopropyl azodicarboxylate Cbz-Cl=benzyl chloroformate CAN=ceric ammonium nitrate SAX=Strong Anion Exchanger SCX=Strong Cation Exchanger Ar=argon $N_2$=nitrogen min=minute(s)

h or hr=hour(s)

L=liter mL=milliliter $\mu$L=microliter g=gram(s)

mg=milligram(s)

mol=moles mmol=millimole(s)

meq=milliequivalent

RT=room temperature sat or sat'd=saturated aq.=aqueous

TLC=thin layer chromatography

HPLC=high performance liquid chromatography

LC/MS=high performance liquid chromatography/mass spectrometry

MS or Mass Spec=mass spectrometry

NMR=nuclear magnetic resonance mp=melting point

The following working Examples represent preferred embodiments of the present invention.

EXAMPLE 1

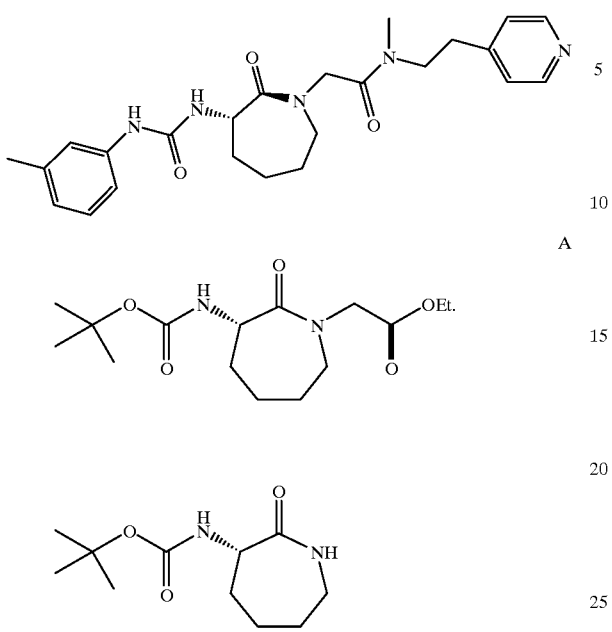

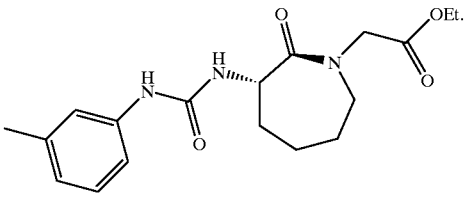

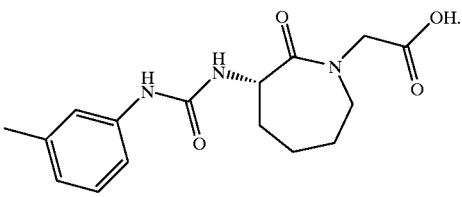

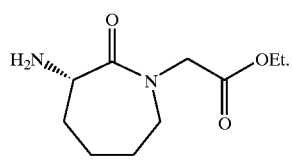

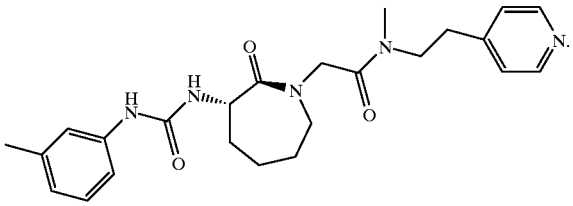

compound in 40 mL of dry THF was added dropwise 72 mL (72 mmol, 2 eq) of a 1 M solution of lithium hexamethyldisilazide (LHMDS) in THF over 1 h. After 10 min, a solution of 4.4 mL (40 mmol, 1.1 eq) of bromoethylacetate in 10 mL of dry THF was added dropwise over 10 min and the resulting reaction mixture was stirred at RT for 17 h. The reaction mixture was diluted with diethyl ether (100 mL) and washed twice with 5% $KHSO_4$ (aq.), followed by saturated $NaHCO_3$ and brine. The organic solution was dried ($MgSO_4$) and concentrated to afford 11.3 g (99%) of title compound as a viscous yellow brown oil. 1H and 13C NMR spectra were consistent with the desired product and indicated the material was pure except for a small amount of hexamethyldisilazane. The material was used without further purification.

To a solution of 7.8 g (25 mmol, 1 eq) of Part A compound in 10 mL of diethyl ether was added 50 mL (50 mmol, 2 eq) of a 1 M solution of hydrochloric acid in diethyl ether. The reaction mixture was stirred at RT for 18 h. The resulting heterogeneous reaction mixture was concentrated and the oily residue was triturated with ether, dissolved in methanol and concentrated to afford 5.1 g (81%) of title compound as a yellow solid. 1H and 13C NMR spectra were consistent with the desired product.

To a solution of 5.1 g (20 mmol, 1 eq) of Part B compound in 120 mL of dry THF was added 5.7 mL (41 mmol, 3 eq) of triethylamine and 3.9 mL (30 mmol, 1.5 eq) of m-tolylisocyanate. The reaction mixture was stirred at RT for 18 h. The reaction mixture was concentrated and the residue dissolved in methanol. An insoluble impurity was removed by filtration and the crude product was again concentrated. Flash chromatography ($SiO_2$) eluting with 9:1 $CH_2Cl_2$:ethyl acetate (EtOAc) afforded 3.3 g (48%) of title compound as a light brown solid. 1H and 13C NMR spectra were consistent with the desired product.

To a solution of 2.3 g (7 mmol, 1 eq) of Part C compound in 30 mL of THF and 30 mL of EtOH was added 8.3 mL (17 mmol, 2.5 eq) of 2 M sodium hydroxide in water. The reaction mixture was stirred at RT for 18 h. The reaction mixture was concentrated, the residue was dissolved in 20 mL of water and the pH was adjusted to 3 with 1 M HCl. The resulting precipitate was collected by filtration, washed with water (10 mL), washed with hexane (10 mL) and dried to afford 1.7 g (82%) of title compound as a light yellow solid. 1H and 13C NMR spectra were consistent with the desired product.

The title compound was prepared as part of an automated solution phase run using a liquid handler (Hamilton Microlab® 2200) for reagent and starting material addition using the following procedure.

To a 16 mm×100 mm reaction tube was added via the liquid handler 100 μL (3.9 mg, 0.036 mmol, 1 eq) of a stock solution of 4-[2-(methylamino)ethyl]pyridine in THF, 300 μL (7 mg, 0.057 mmol, 1.6 eq) of a stock solution of diisopropylcarbodiimide in $CH_2Cl_2$, 300 μL (8 mg, 0.057 mmol, 1.6 eq) of a stock solution of 7-aza-1-hydroxybenzotriazole in DMF and 300 μL (12 mg, 0.038 mmol, 1.05 eq) of a stock solution of Part D compound in CH₂C₂. The tube was removed and mixed on an orbital shaker for 72 h.

The product was purified via solid phase extraction using a Varian SCX cation exchange column (1 g of sorbent in 6 mL column, 0.3 meq/g) by the procedure outlined below:

1) Column conditioned with 2×7.5 mL of MeOH (10 mL/min).
2) Reaction mixture (1 mL) loaded onto SCX column (3 mL/min).
3) Column rinsed with 20 mL of MeOH (6 mL/min).
4) Column rinsed with 10 mL of 0.1 N ammonia in MeOH (6 mL/min).
5) Product eluted with 8 mL of 2 N ammonia in MeOH into a tared 16×100 tube (6 mL/min).

The product solution was concentrated using a speed vac for 14 h to afford 17 mg of title compound (109%) as an oil. Reverse phase analytical HPLC analysis indicated a purity of 96%.

MS (electrospray): m/z 438 (M+H).

EXAMPLES 2 TO 4

Following the procedure of Example 1, the following compounds of the invention were prepared.

EXAMPLE 5

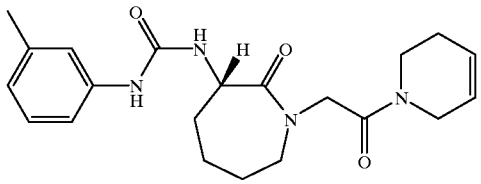

Chiral

Example 5 was prepared as part of an automated solution phase run using a liquid handler (Hamilton Microlab® 2200) for reagent and starting material addition using the following procedure.

To a 16 mm×100 mm reaction tube was added via the liquid handler 100 µL (0.057 mmol, 1.5 eq) of a stock solution of 1,2,3,6-tetrahydropyridine in THF, 300 µL of a stock solution containing both ethyldimethylaminopropyl-carbodiimide hydrochloride (0.057 mmol, 1.5 eq) and dimethylaminopyridine (0.057 mmol, 1.5 eq) in CH₂Cl₂ and 600 µL (0.038 mmol, 1.0 eq) of a stock solution of Example 1 Part D compound in CH₂Cl₂. The tube was removed and mixed on an orbital shaker for 72 h.

| Example No. | Structure | Mass Spec. m/z (M + H)⁺ |
|---|---|---|
| 2 | Chiral | 424 |
| 3 | Chiral | 438 |
| 4 | Chiral | 479 |

The product was purified via solid phase extraction using a Varian SCX cation exchange column (1 g of sorbent in 6 mL column, 0.3 meq/g) by the procedure outlined below.
1) Column conditioned with 15 of MeOH (10 mL/min).
2) Reaction mixture (1 mL) was loaded onto SCX column (3 mL/min) and effluent was collected into a tared 16 mm×100 mm tube.
3) Column rinsed with 6 mL of MeOH and collected into tared tube (6 mL/min).

The product solution was concentrated using a speed vac for 14 h to afford 14 mg of Example 5 compound (94%) as an oil. Reverse phase analytical HPLC analysis indicated a purity of 97%.

MS (electrospray): m/z 385 (M+H).

EXAMPLES 6 TO 10

Following the procedure of Example 5, the following compounds of the invention were prepared.

| Example No. | Structure | Mass Spec. m/z (M + H)+ |
|---|---|---|
| 6 | Chiral | 403 |
| 7 | Chiral | 389 |
| 8 | Chiral | 387 |
| 9 | Chiral | 427 |
| 10 | Chiral | 373 |

EXAMPLE 11

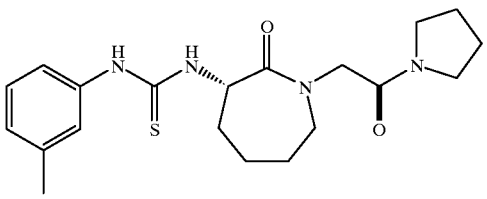

A

To a solution of (55 g, 0.35 mol) in 400 mL of $CH_2Cl_2$ was added dropwise a solution of pyrrolidine (25 g, 0.35 mol) and triethylamine (42.4 g, 0.42 mol) in 100 mL of $CH_2Cl_2$ at 0° C. under argon over 5h. The reaction mixture was allowed to slowly warm to room temperature with stirring for an additional 14 h. The reaction mixture was washed with $H_2O$ (250 mL×3), 0.5 N HCl (250 mL), saturated NaCl (300 mL×3), and dried ($Na_2SO_4$) and concentrated. The resulting residue was purified by flash column chromatography (elute with 1% MeOH in $CH_2Cl_2$) to yield title compound (46.1 g, 68.6%) as off-brown solid. Found: $MH^+$: 191.7.

B

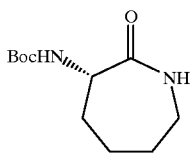

To a solution of (8.0 g, 35.1 mmol) in 600 mL of THF was added dropwise 70.2 mL of LHMDS (1.0 M in THF) at room temperature under argon over 3 h, followed by adding dropwise a solution of Part B compound (7.4 g, 38.6 mmol) in 100 mL of THF over 2 h. The reaction mixture was stirred for an additional 14 h at room temperature. The reaction mixture was poured into 5% $KHSO_4$ (300 mL), and added ethylacetate (AcOEt) (300 mL). The organic layer was washed with 5% $KHSO_4$ (300 mL), saturated $NaHCO_3$ (300 mL×2), $H_2O$ (300 mL×3), and dried ($Na_2SO_4$) and concentrated to yield title compound (11.1 g, 93.2%) as yellow oil. Found: $MH^+$: 340.1.

C

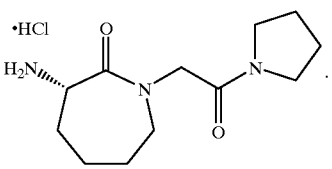

To a solution of Part B compound (4.1 g, 12.1 mmol) in 100 mL of $CH_2Cl_2$ was added 100 mL of HCl in $Et_2O$ (1.0 M) at room temperature. The mixture was stirred for 14 h. The solvent was removed in vacuum and the resulting residue was purified by ion-exchange resin column chromatography (elute with 2% ammonia in MeOH) to yield title compound (1.91 g, 66.0%) as yellow oil. Found: $MH^+$: 240.2.

D

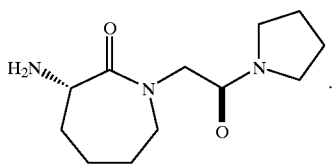

To a solution of Part C compound (90.8 mg, 0.38 mmol) in 3 mL of $CH_2Cl_2$ was added a solution of m-tolyl-isothiocyanate (51.5 mg, 0.345 mmol) in 2 mL of $CH_2Cl_2$ at room temperature. The reaction mixture was stirred for 0.5h and concentrated in vacuum. The resulting residue was purified by flash column chromatography (eluted with 1% MeOH in $CH_2Cl_2$) to yield title compound (130 mg, 97.0%) as white solid. Found: $MH^+$: 389.1.

EXAMPLES 12 TO 16

The following compounds of the invention were prepared employing procedures described in Example 11.

| Example No. | Structure | Mass Spec. m/z (M + H)+ |
|---|---|---|
| 12 | Chiral | 375 |
| 13 | Chiral | 403 |
| 14 | Chiral | 420 |
| 15 | Chiral | 405 |

-continued

| Example No. | Structure | Mass Spec. m/z (M + H)+ |
|---|---|---|
| 16 | 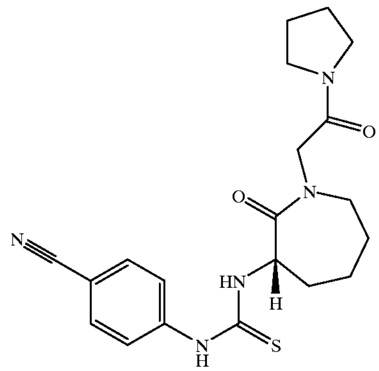 | 400 |

EXAMPLE 17

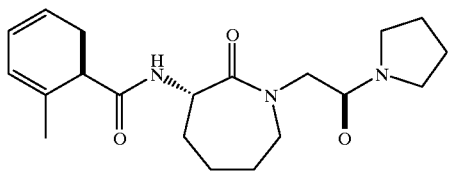

To 13.9 mg of polyvinylpyridine (9.0 mmol/g) was added 0.400 mL of solution of Example 13, Part C compound in dichloromethane (0.158 mmol/mL) and 0.400 mL of solution of o-toluoyl chloride in dichloromethane (0.173 mmol/mL). The mixture was shaken for 4 h. at room temperature. The reaction mixture was then added to 31.4 mg of aminomethylpolystyrene (1.0 mmol/g) and 0.200 mL of dichloromethane. The mixture was shaken for 14 h at room temperature. The reaction solution was collected and the residue resins were washed with dichloromethane (0.400 mL). The combined reaction solutions were dried by speed vacuum to yield title compound (17.1 mg, 69%). Found: MH+: 358.1.

EXAMPLES 18, 19

The following compounds were prepared employing the procedure as described in Example 17.

| Example No. | | Structure | Mass Spec. |
|---|---|---|---|
| 18 | Chiral | 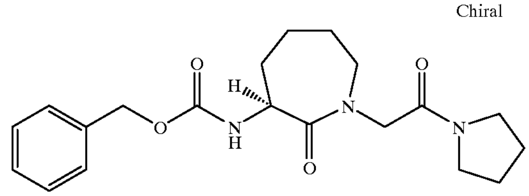 | 374 |
| 19 | Chiral | 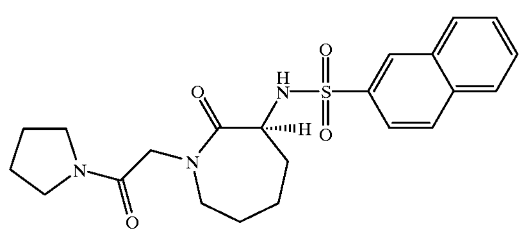 | 430 |

EXAMPLES 20 TO 57
The following compounds were prepared employing procedures as described in previous Examples.
| Example No. | Structure | Mass Spec. m/z (M + H)+ |
|---|---|---|
| 20 | 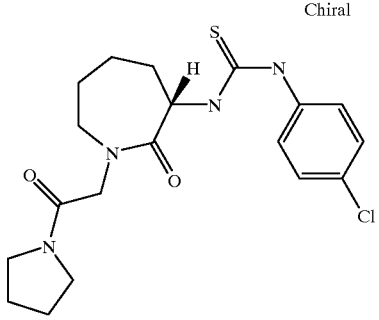 Chiral | 409 |
| 21 | 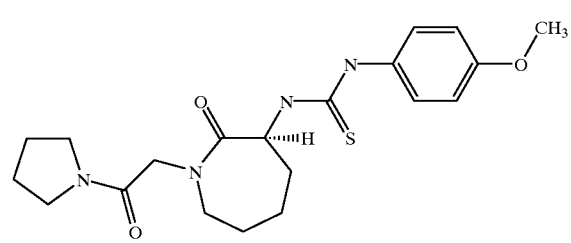 Chiral | 405 |
| 22 | 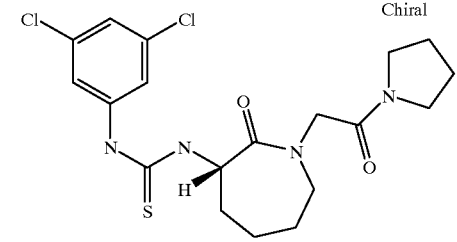 Chiral | 443 |
| 23 | 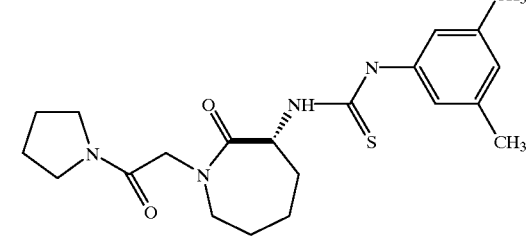 Chiral | 403 |

-continued

| Example No. | Structure | Mass Spec. m/z (M + H)+ |
|---|---|---|
| 24 | Chiral | 425 |
| 25 | 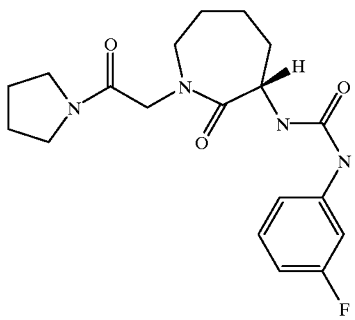 | 377 |
| 26 | Chiral | 437 |
| 27 | Chiral | 409 |

-continued

| Example No. | Structure | Mass Spec. m/z (M + H)+ |
|---|---|---|
| 28 | Chiral | 393 |
| 29 | Chiral | 409 |
| 30 | Chiral | 443 |
| 31 | Chiral | 393 |

-continued
| Example No. | Structure | Mass Spec. m/z (M + H)+ |
|---|---|---|
| 32 | 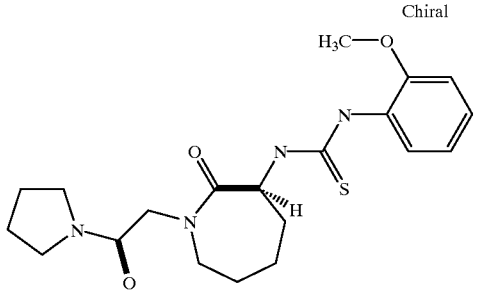 | 405 |
| 33 | 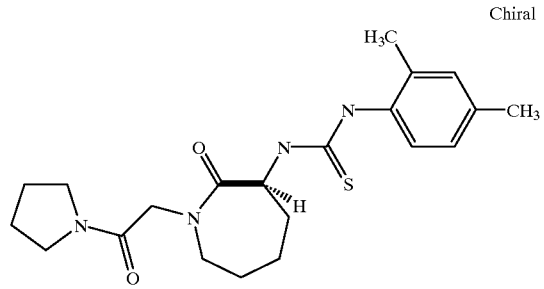 | 403 |
| 34 | 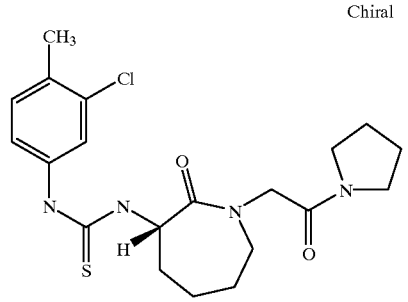 | 423 |
| 35 | 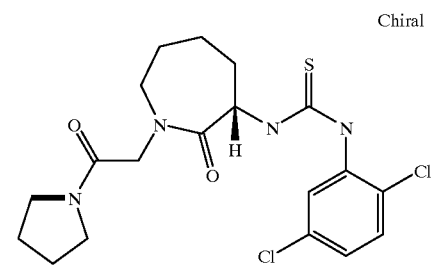 | 443 |

-continued

| Example No. | Structure | Mass Spec. m/z (M + H)+ |
|---|---|---|
| 36 | Chiral | 400 |
| 37 | Chiral | 439 |
| 38 | Chiral | 501 |
| 39 | Chiral | 481 |

-continued

| Example No. | Structure | Mass Spec. m/z (M + H)+ |
|---|---|---|
| 40 | Chiral | 433 |
| 41 | Chiral | 417 |
| 42 | Chiral | 419 |
| 43 | 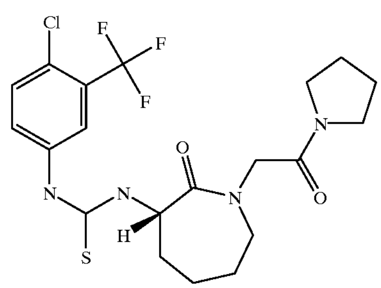 | 477 |
| 44 | Chiral | 403 |

-continued

| Example No. | Structure | Mass Spec. m/z (M + H)+ |
|---|---|---|
| 45 | Chiral | 454 |
| 46 | Chiral | 420 |
| 47 | Chiral | 434 |
| 48 | Chiral | 450 |

-continued

| Example No. | Structure | Mass Spec. m/z (M + H)+ |
|---|---|---|
| 49 | Chiral | 450 |
| 50 | Chiral | 376 |
| 51 | Chiral | 393 |
| 52 | 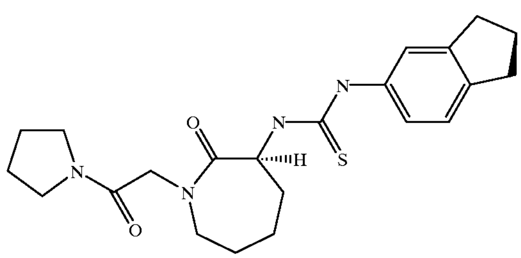 | 415 |
| 53 | 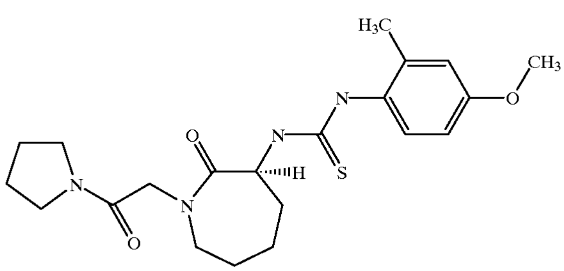 | 419 |

-continued

| Example No. | Structure | Mass Spec. m/z (M + H)+ |
|---|---|---|
| 54 | 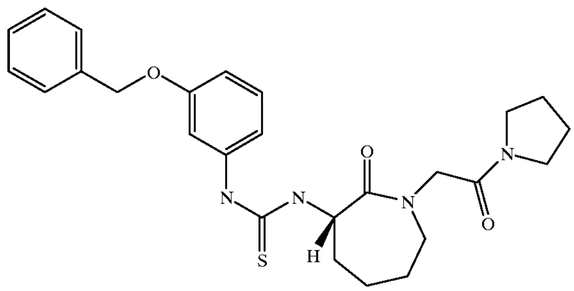 | 481 |
| 55 | 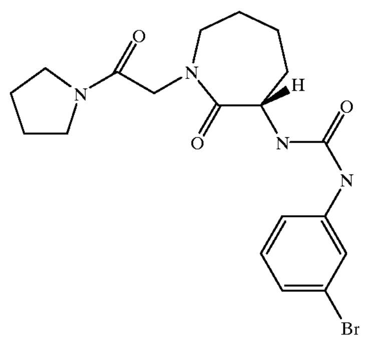 | 437 |
| 56 | 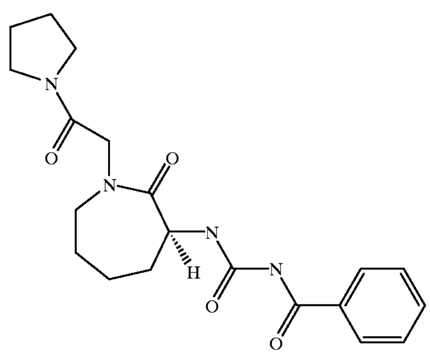 | 387 |
| 57 | 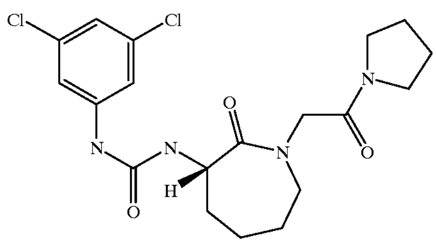 | 427 |
| 58 | 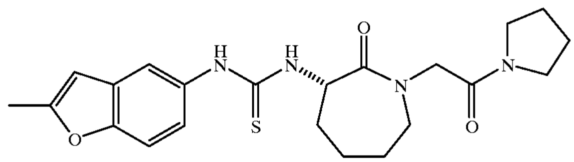 | 429 |

-continued

| Example No. | Structure | Mass Spec. m/z (M + H)+ |
|---|---|---|
| 59 | 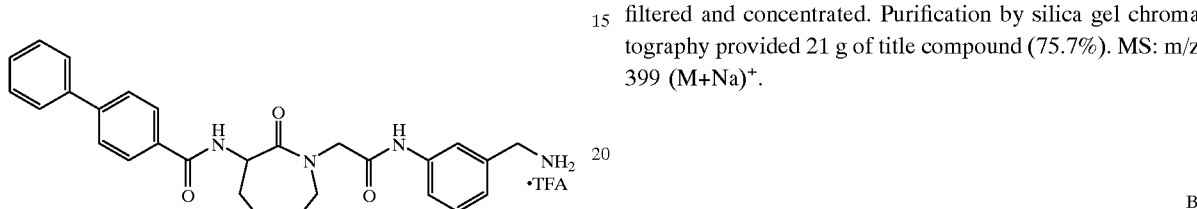 | 413 |

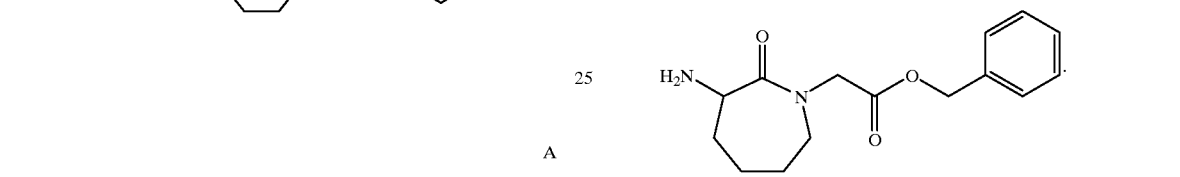

A

To a solution of

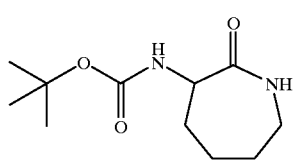

(16.77 g, 73.6 mmol, 1.0 eq) in THF (400 mL) under a nitrogen atmosphere at −78° C. was added LiHMDS (1.0 M in THF, 150 mL, 150 mmol, 2.04 eq) dropwise via an addition funnel over 10 minutes. The resulting mixture was stirred for an additional 10 minutes at −78° C., warmed to room temperature and stirred at room temperature for 1 hour. The reaction mixture was then cooled to −78° C. and phenyl 2-bromoacetate (14 mL, 88.3 mmol, 1.2 eq) was added. The reaction mixture was warmed to room temperature and stirred for 18 hours. 1N KHSO$_4$ was added until the pH remained neutral. NaCl (~5 g) was added to the resulting bi-phasic solution. After the layers were mixed and allowed to separate, the upper THF layer was removed and set aside and the aqueous layer was extracted once with EtOAc. The combined THF and EtOAc extracts were dried over MgSO$_4$, filtered and concentrated. Purification by silica gel chromatography provided 21 g of title compound (75.7%). MS: m/z 399 (M+Na)+.

B

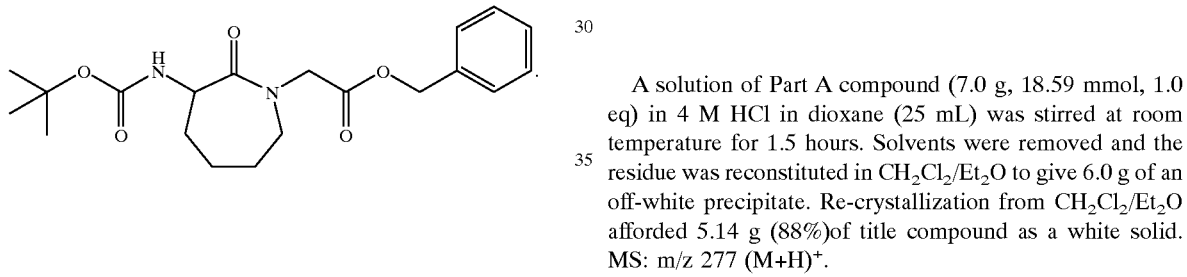

A solution of Part A compound (7.0 g, 18.59 mmol, 1.0 eq) in 4 M HCl in dioxane (25 mL) was stirred at room temperature for 1.5 hours. Solvents were removed and the residue was reconstituted in CH$_2$Cl$_2$/Et$_2$O to give 6.0 g of an off-white precipitate. Re-crystallization from CH$_2$Cl$_2$/Et$_2$O afforded 5.14 g (88%)of title compound as a white solid. MS: m/z 277 (M+H)+.

C

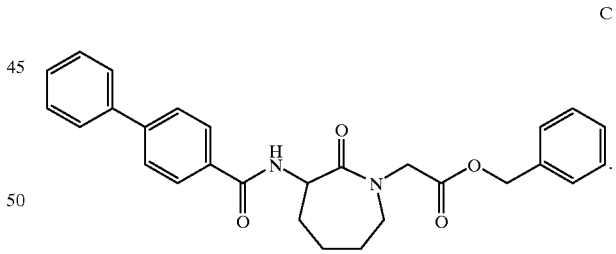

A solution of Part B compound (2.7 g, 8.63 mmol, 1 eq), EDC (1.98 g, 10.3 mmol, 1.2 eq), HOBT (1.40 g, 10.35 mmol, 1.2 eq) in CH$_2$Cl$_2$ (100 mL) at 0° C. was treated with Pr$_2$NEt (6.0 mL, 34.5 mmol, 4 eq). The reaction mixture was brought to room temperature and 4-biphenylcarboxylic acid (2.05 g, 10.35 mmol, 1.2 eq) was added. The reaction mixture was stirred at room temperature for 3 hours. The reaction mixture was then diluted with CH$_2$Cl$_2$, washed with 5% NaHCO$_3$, dried over MgSO$_4$, filtered and concentrated. Purification by silica gel chromatography gave 2.16 g (55%) of title compound as a white foam. MS: m/z 479 (M+Na)+.

D

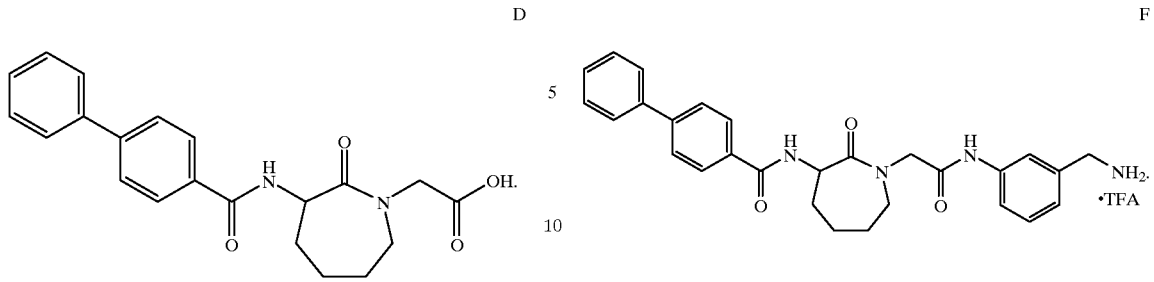

To a solution of Part C compound (4.5 g, 9.86 mmol, 1.0 eq) in THF (200 mL) at RT was added 10% Pd/C (3 g) followed by bubbling of $H_2$ through the solution for 1 hour. The reaction was then stirred under $H_2$ for 4 hours. The reaction mixture was filtered through a pad of celite and the pad was rinsed twice with THF (2×25 mL). Solvent was removed to provide 3.62 g (100%) of title compound as a white solid. MS: m/z 367 (M+H)$^+$.

E

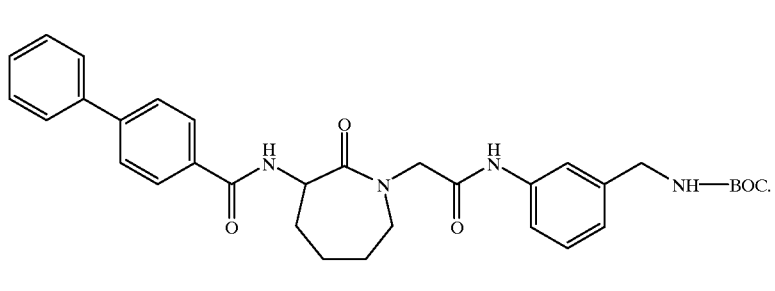

Part E compound was prepared as part of a semi-automated parallel library.

To a 16×100 mm reaction tube was added Part D compound (30 mg, 0.082 mmol, 1.0 eq), polystyrene-EDC (Advanced Chemtech catalog #SP5005, 100 mg, 0.8 mmol/g, 0.08 mmol, 0.98 eq), iPr$_2$NEt (0.05 mL, 0.29 mmol, 3.5 eq) and amine

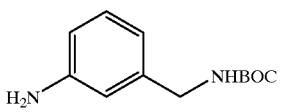

(14 mg, 0.063 mmol, 0.77 eq) in DMF (0.6 mL) and DCE (1.0 mL), and was shaken for 3 days. Additional polystyrene-EDC (50 mg, 0.8 mmol/g, 0.04 mmol, 0.49 eq) and DCE (0.5 mL) were added and the reaction mixture was shaken for an additional 24 hours. To the reaction mixture was added Polystyrene-Trisamine (Argounaut Tech, 50 mg, 6.8 mmol/g, 0.34 mmol, 4.15 eq) as a scavenger resin and the reaction mixture was shaken for 24 hours. The reaction mixture was filtered and the eluent was concentrated using a speed vac. Purification by reverse phase preparative HPLC (Shimadzu VP-ODS, flow rate 20 mL/min) followed by concentration using a speed vac gave analytically pure title compound. MS: m/z 593 (M+Na)$^+$.

F

For compounds from the above semi-automated parallel library having BOC protecting groups, deprotection was carried out using the following procedure.

Part E compound was taken up in 10% TFA in DCE (5 mL) and let set for 2 hours. Concentration using a speed vac then afforded 4.8 mg (10% from Part D compound) of title compound. MS: m/z 471 (M+H)$^+$.

EXAMPLE 61

A

The title compound is a known compound as disclosed in Skiles, J. W. et al, Bioorg. Med. Chem. Lett. 1993, 3, 773.

B

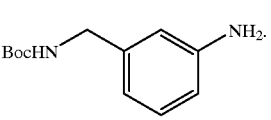

The title compound is a known compound as disclosed in Collins, J. L. et al, J. Med. Chem. 1998, 41, 2858.

C

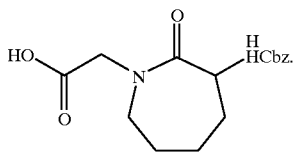

TFA (20 mL) was slowly added to a solution of Part A compound (8.64 g, 22.95 mmol) in CH$_2$Cl$_2$ (30 mL) at 0°C. The reaction mixture was then stirred at room temp. After 24 h the solution was concentrated. The residue was dissolved in CHCl$_3$ (50 mL) and the solution was concentrated. This was repeated 2 more times. A portion of the crude product was purified by silica gel chromatography giving 2.90 g of title compound.

D

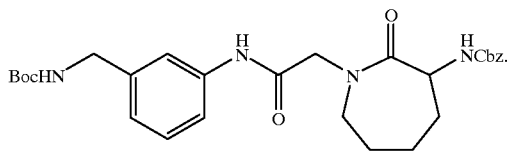

EDAC-HCl (1.74 g, 9.05 mmol) was added to a stirred solution of Part B compound (2.01 g, 9.05 mmol), Part C compound (2.90 g, 9.05 mmol) and HOBt (1.22 g, 9.05 mmol) in CH$_2$Cl$_2$ (35 mL) at 0° C. NMM (1.04 mL, 9.50 mmol) was added and the reaction mixture was stirred at room temp. After 24 h the solution was diluted with CH$_2$Cl$_2$ (100 mL) and washed with 5% KHSO$_4$ (50 mL), sat. NaHCO$_3$ (50 mL), and sat NaCl (50 mL). The solution was dried (MgSO$_4$) and concentrated. The crude product was purified by silica gel chromatography to afford 3.60 g (78%) of title compound.

E

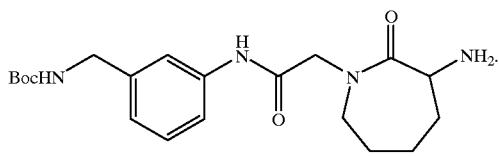

20% Pd(OH)$_2$ (0.34 g) was added to a stirred solution of Part D compound (3.39 g, 6.65 mmol) in MeOH (25 mL). A H$_2$ atmosphere was introduced via balloon. After 24 h the solution was filtered and the filtrate was concentrated to give 2.44 g (94%) of title compound.

F

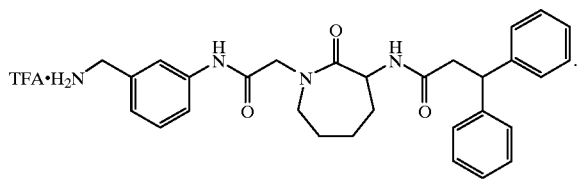

To a reaction tube was added via liquid handler 320 μL (10.8 mg, 0.048 mmol) of a 0.15 M stock solution of

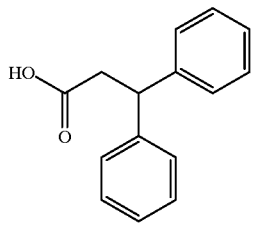

in DMF. 0.30 mL of a DCE solution containing EDC (10.5 mg, 0.055 mmol) and DMAP (6.7 mg, 0.055 mmol) was added manually via syringe. 0.30 mL of a DCE solution containing Part E compound (18.8 mg, 0.050 mmol) was added via the liquid handler. The reaction tube was mixed on an orbital shaker for 12 h. The reaction mixture was then drained through a SCX cation exchange column (0.30 g of absorbent) which was preconditioned with MeOH (0.30 mL) into a 2.5 mL microtube. The column was rinsed with CH$_2$Cl$_2$ (0.3 mL) and MeOH (0.40 mL). The organic solution containing intermediate F(1)

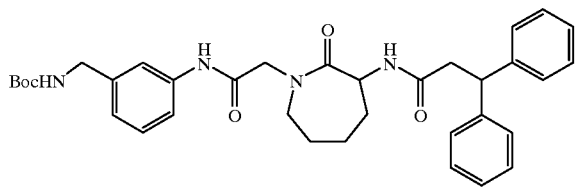

was concentrated by speed vac.

DCE (0.60 mL) was added to the 2.5 mL microtube containing the above intermediate F(1). Upon dissolution TFA (0.30 mL) was added via syringe. The microtube was sealed and shaken using a mini-vortexer. After 3 h the solution was concentrated by speed vac. The product was dissolved in MeOH (1.0 mL) and purified via solid phase extraction using a SCX cation exchange column (0.30 g of absorbent) which was preconditioned with MeOH (0.30 mL). The column was washed with MeOH (2×1.5 mL) to remove impurities. The product was then eluted off the column using 2.0 M NH$_3$ in MeOH (1.5 mL). The eluant was then concentrated by speed vac. The crude product was further purified by PREP HPLC (Shimadzu VP-ODS 20×50 mm column) using a gradient of 0 to 100% Solvent B over 5 min and a flow rate of 20 mL/min. 6.73 mg (23%) of title compound was obtained. Mass spec (M+H)$^+$=calc'd=499, found=499.

NOTE—20 of the 72 compounds were purified by PREP HPLC. The rest of the compounds were pure enough to be submitted directly as the free amines.

EXAMPLE 62

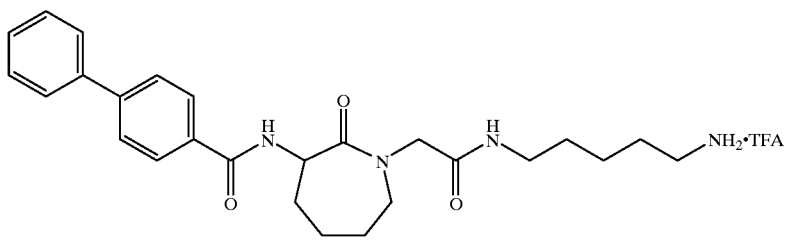

Solution A: To a solution of Example 60 Part D compound (240 mg, 0.655 mmol) in dichloroethane (15 ml) was added DMAP (199 mg, 1.63 mmol) followed by EDC (251 mg, 1.31 mmol). Dichloroethane was added to bring the total volume to 18 ml. This reaction mixture was stirred at room temperature for 2 hours.

To a 16×100 mm reaction tube containing N-BOC-1,5-diaminopentane (33 mg, 0.164 mmol) was added Solution A (2 ml, 0.073 mmol of Example 60 Part D compound). The reaction tube was capped and warmed to 40° C. for 20 hours. The reaction was cooled to room temperature and was then passed through an SCX cartridge (CUBCX12M6). The SCX cartridge was washed with methanol (8 ml) and the eluent was collected. Solvents were removed using a speed vac and the resulting residue was taken up in 30% TFA/dichloroethane (2 ml). After agitating the TFA/dichloroethane solution for 2 hours at room temperature, solvents were removed using a speed vac to afford 19 mg (46%) of title compound. MS: m/z 451.21 (M+H)$^+$.

EXAMPLES 63 TO 167

The following compounds were prepared employing procedures as described in previous Examples.

| Example No | Structure | Mass Spec. m/z (M + H)* |
|---|---|---|
| 63 | CNral | 428 |
| 64 | CNral | 428 |

-continued

| Example No | Structure | Mass Spec. m/z (M + H)* |
|---|---|---|
| 65 | 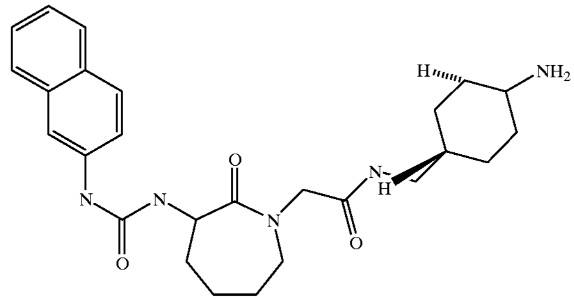 | 466 |
| 66 | 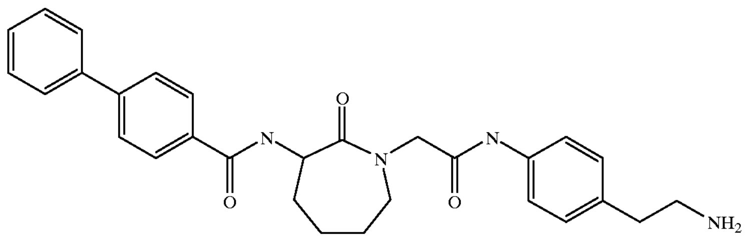 | 485 |
| 67 | 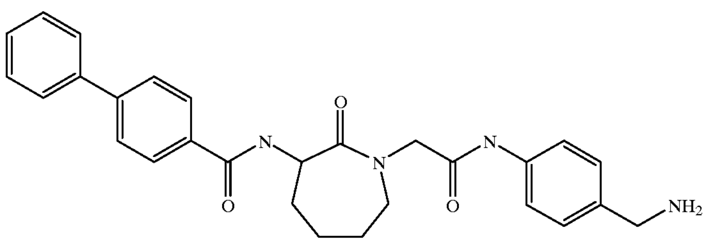 | 471 |
| 68 | 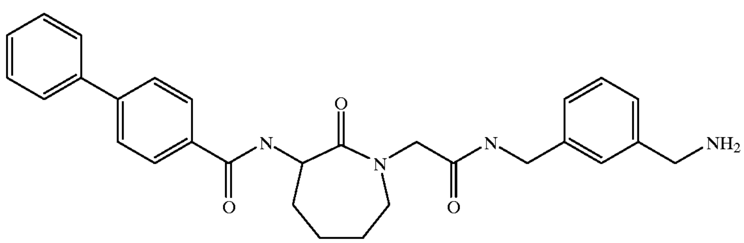 | 485 |
| 69 | 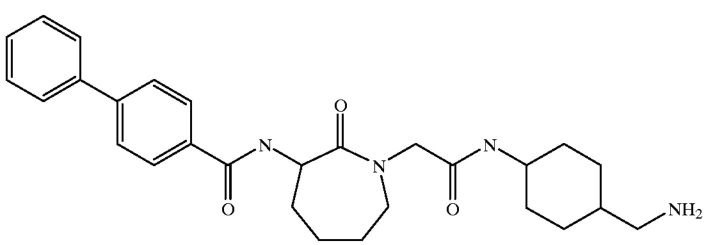 | 477 |

| Example No | Structure | Mass Spec. m/z (M + H)* |
|---|---|---|
| 70 | 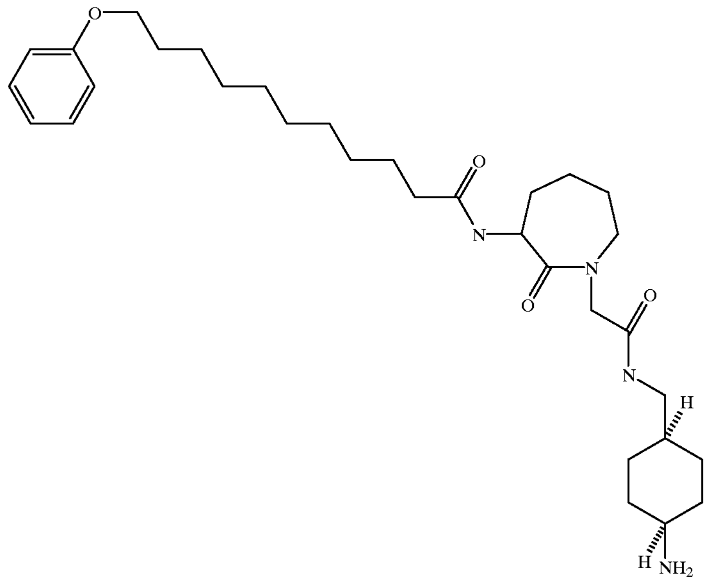 | 557 |
| 71 | 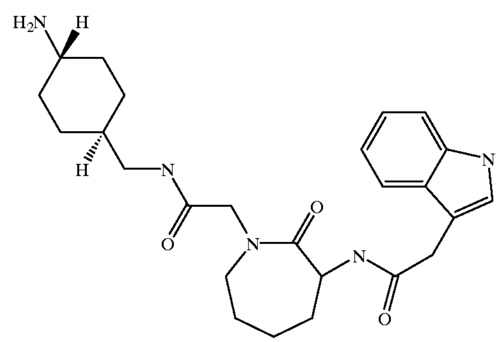 | 454 |
| 72 | 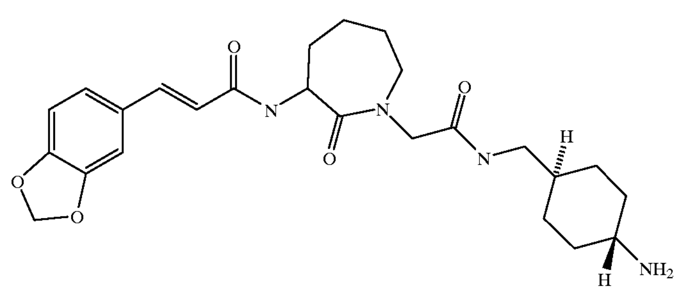 | 471 |
| 73 | 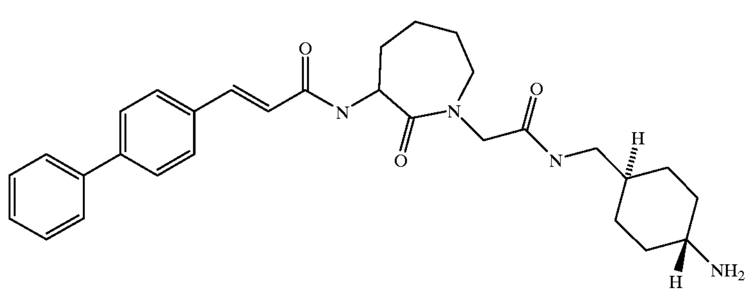 | 503 |

-continued

| Example No | Structure | Mass Spec. m/z (M + H)* |
|---|---|---|
| 74 | 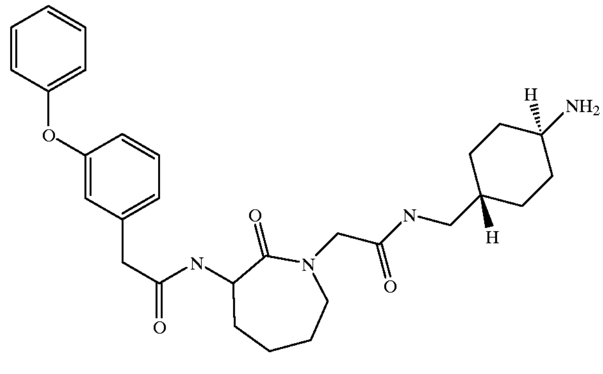 | 507 |
| 75 | 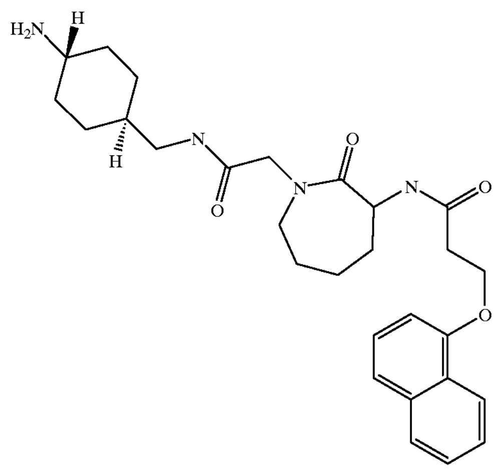 | 495 |
| 76 | 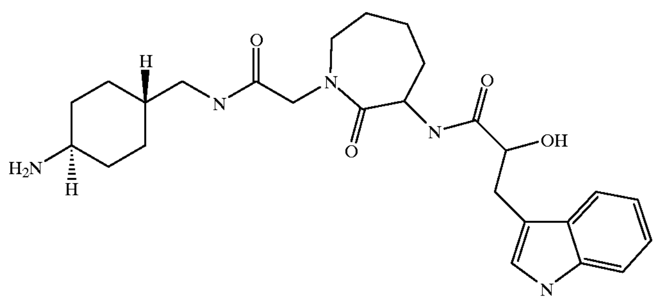 | 484 |
| 77 | 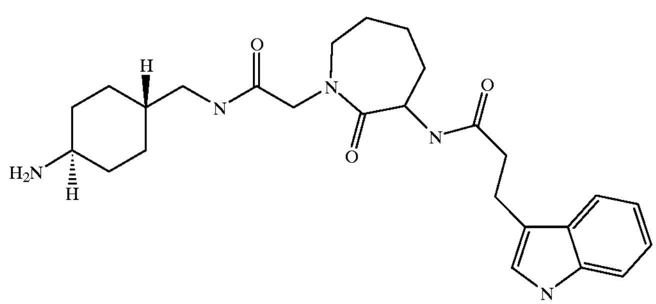 | 468 |

-continued

| Example No | Structure | Mass Spec. m/z (M + H)* |
|---|---|---|
| 78 | 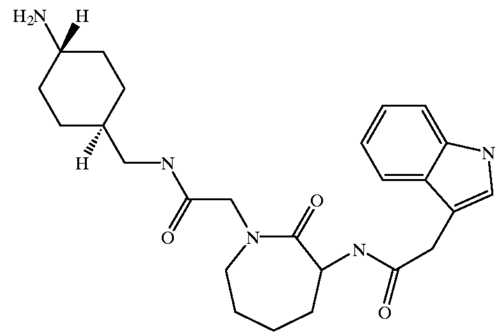 | 482 |
| 79 | 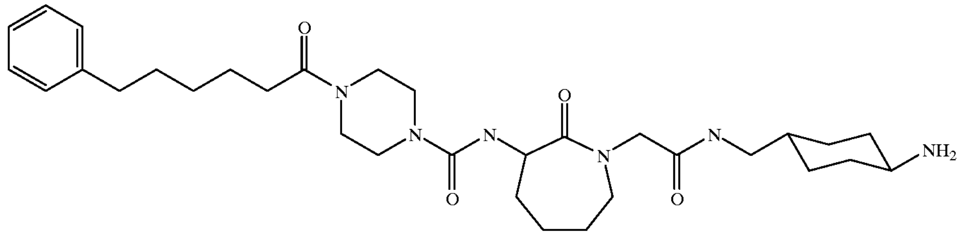 | 583 |
| 80 | 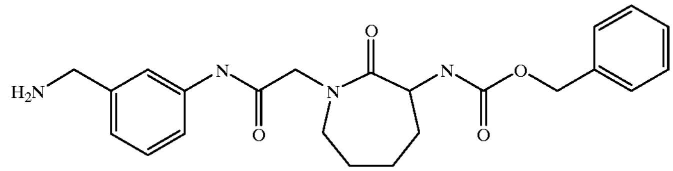 | 425 |
| 81 | 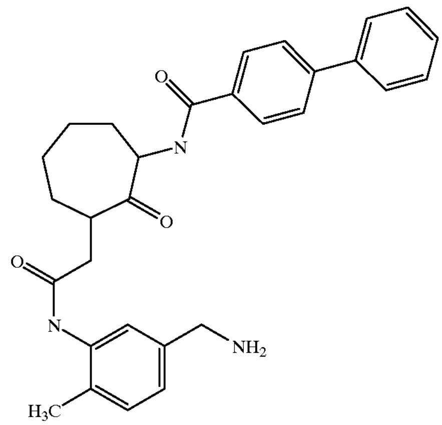 | 485 |
| 82 | 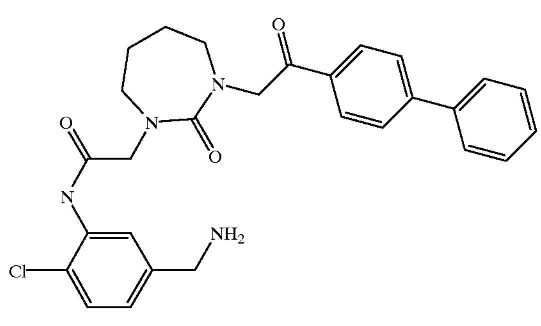 | 506 |

-continued

| Example No | Structure | Mass Spec. m/z (M + H)* |
|---|---|---|
| 83 | 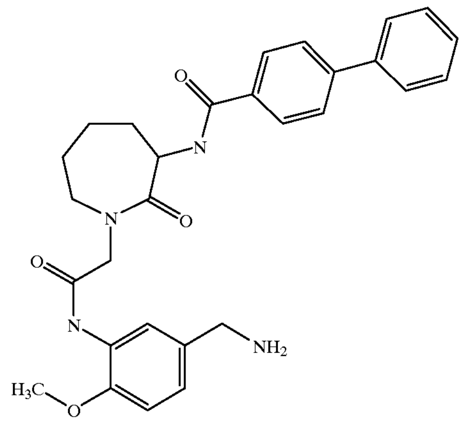 | 501 |
| 84 | 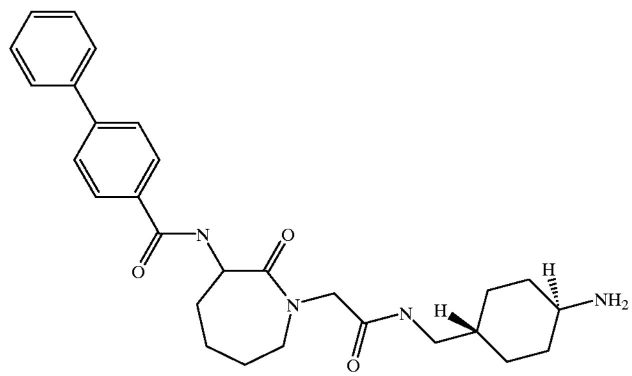 | 477 |
| 85 | 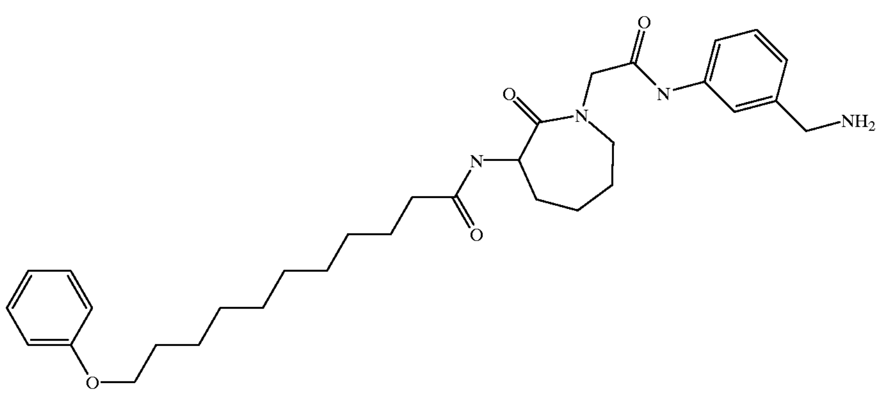 | 551 |
| 86 | 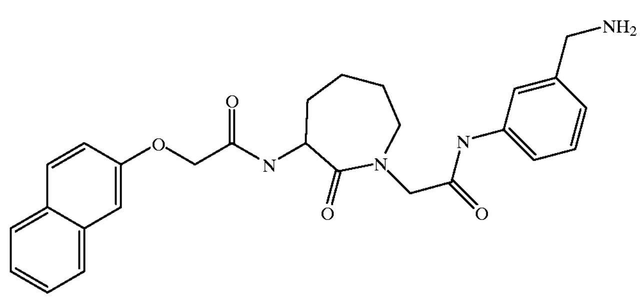 | 475 |

| Example No | Structure | Mass Spec. m/z (M + H)* |
|---|---|---|
| 87 | 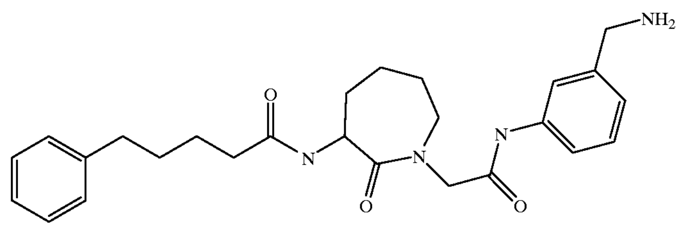 | 451 |
| 88 | 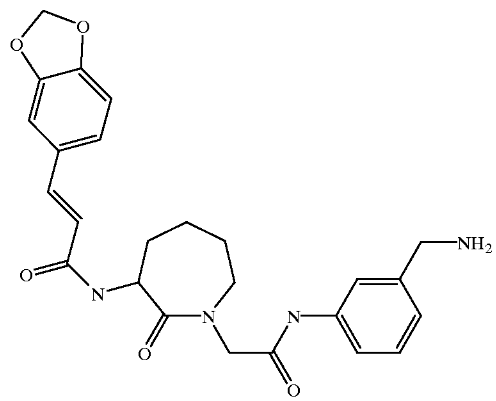 | 465 |
| 89 | 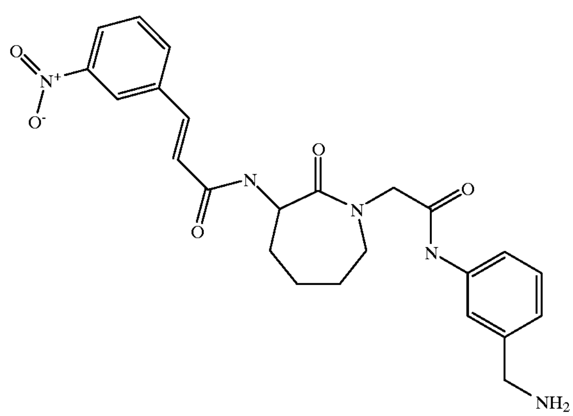 | 466 |

-continued

| Example No | Structure | Mass Spec. m/z (M + H)* |
|---|---|---|
| 90 | 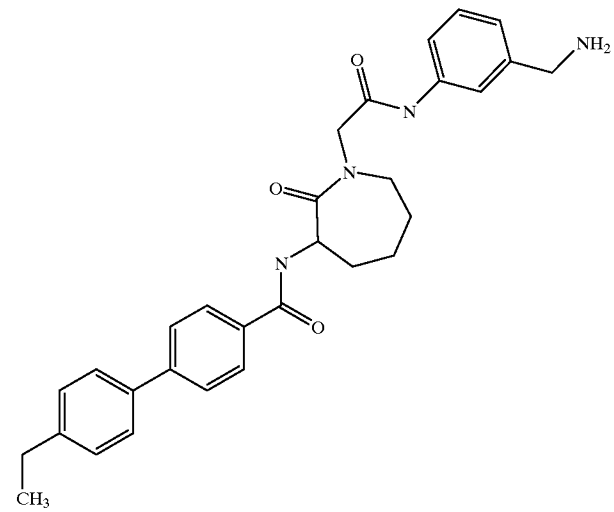 | 499 |
| 91 | 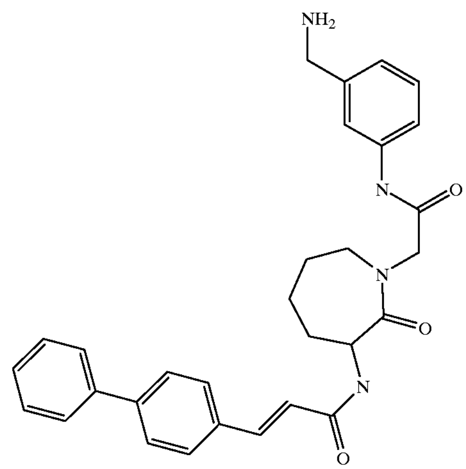 | 497 |
| 92 | 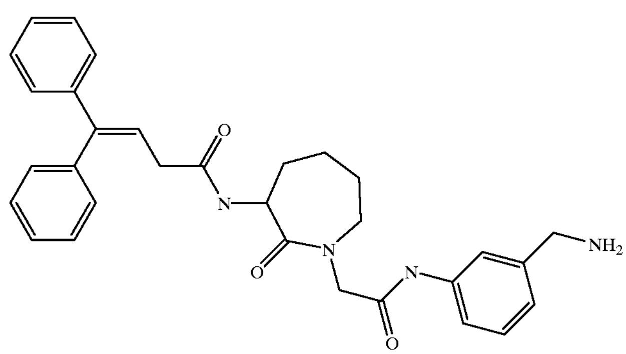 | 511 |

-continued

| Example No | Structure | Mass Spec. m/z (M + H)* |
|---|---|---|
| 93 | 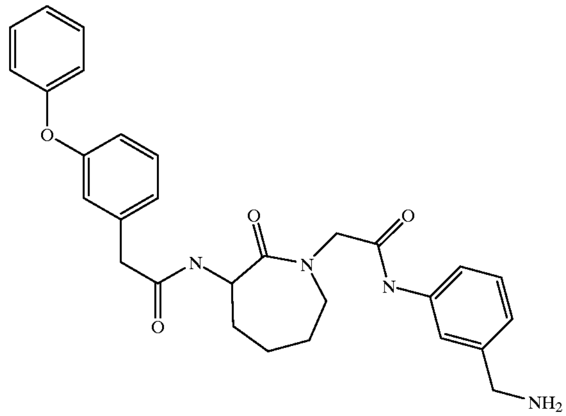 | 501 |
| 94 | 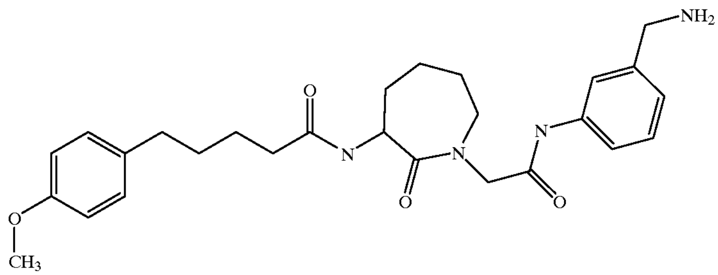 | 481 |
| 95 | 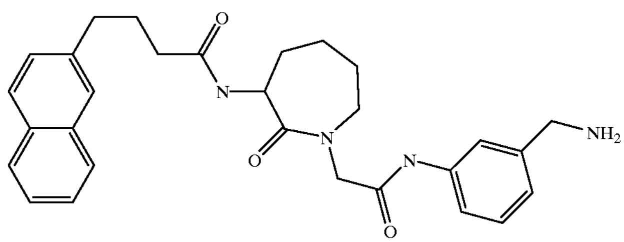 | 487 |
| 96 | 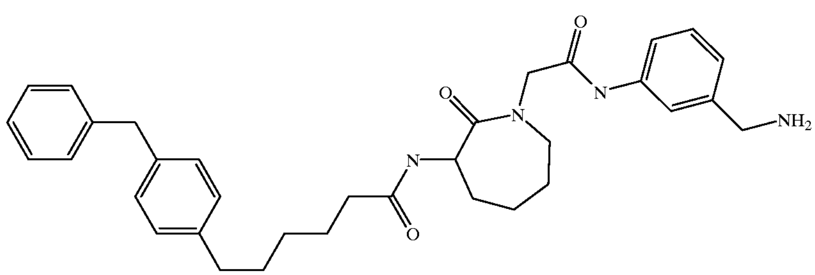 | 555 |
| 97 | 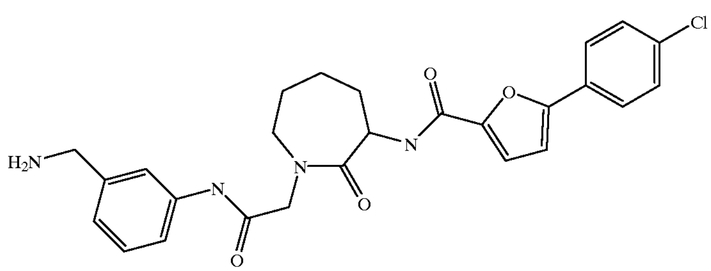 | 495 |

| Example No | Structure | Mass Spec. m/z (M + H)* |
|---|---|---|
| 98 | 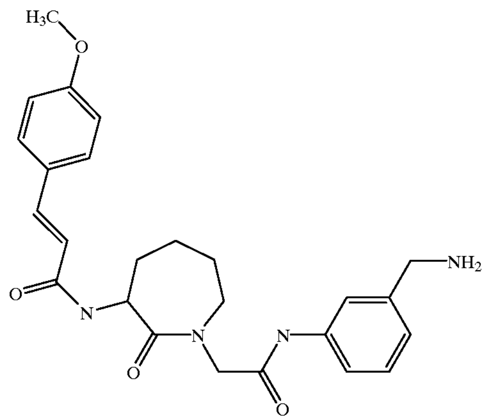 | 451 |
| 99 | 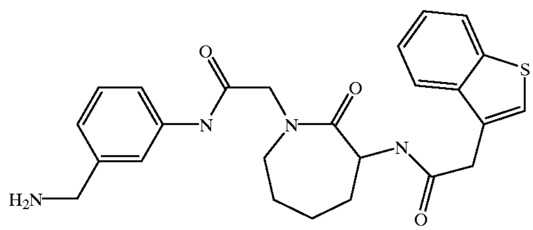 | 465 |
| 100 | 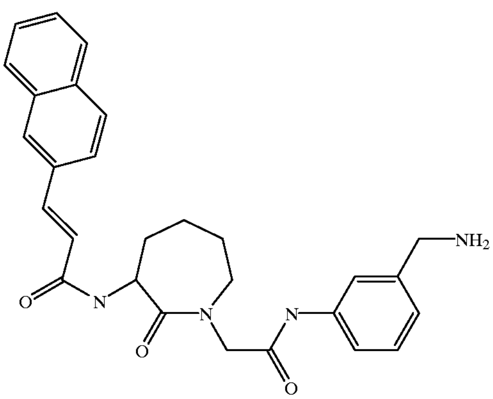 | 471 |
| 101 | 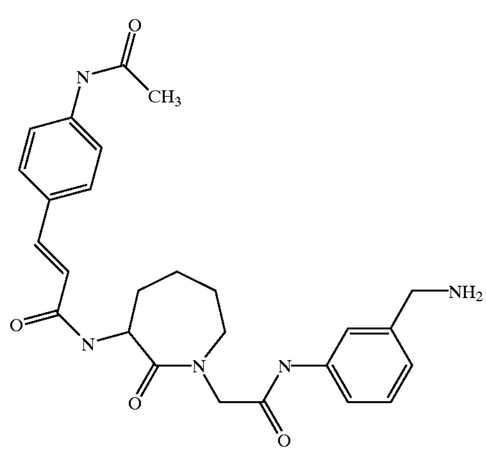 | 478 |

-continued

| Example No | Structure | Mass Spec. m/z (M + H)* |
|---|---|---|
| 102 | 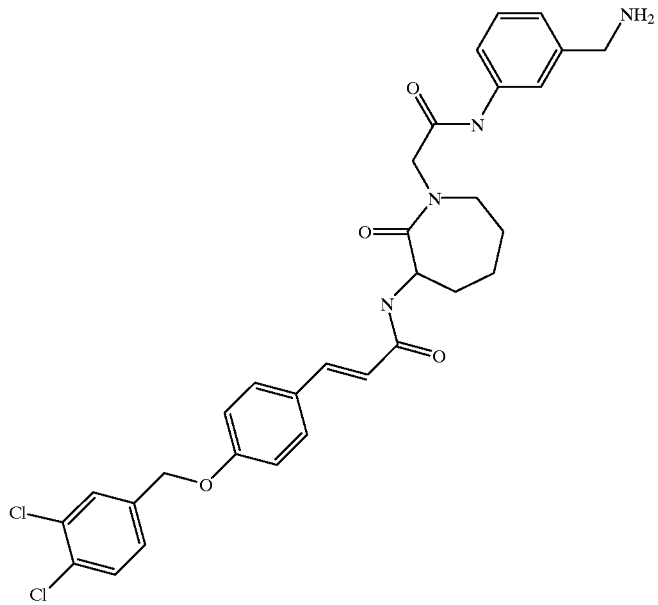 | 596 |
| 103 | 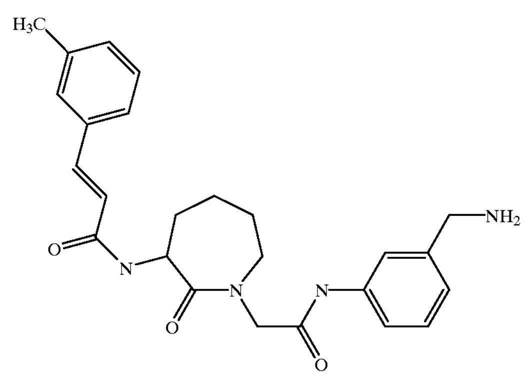 | 435 |
| 104 | 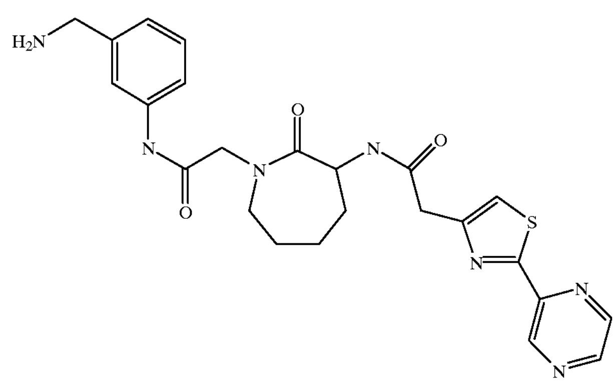 | 494 |

-continued

| Example No | Structure | Mass Spec. m/z (M + H)* |
|---|---|---|
| 105 | 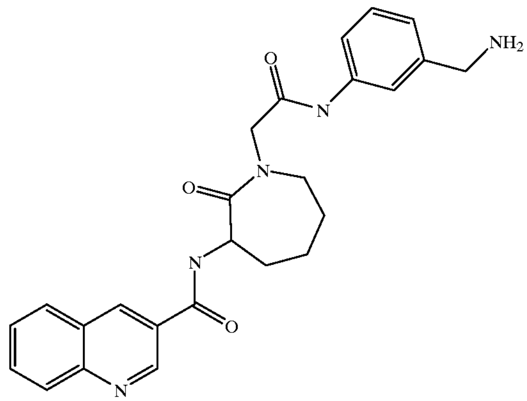 | 446 |
| 106 | 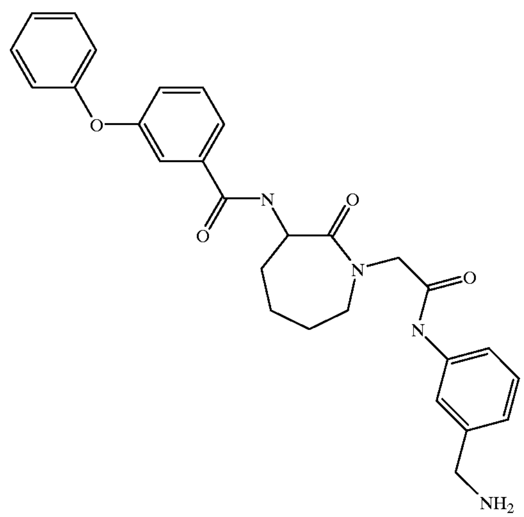 | 487 |
| 107 | 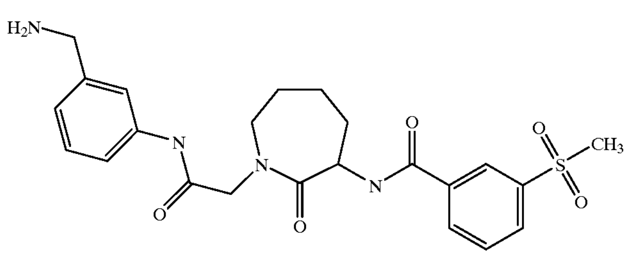 | 473 |

-continued

| Example No | Structure | Mass Spec. m/z (M + H)* |
|---|---|---|
| 108 | 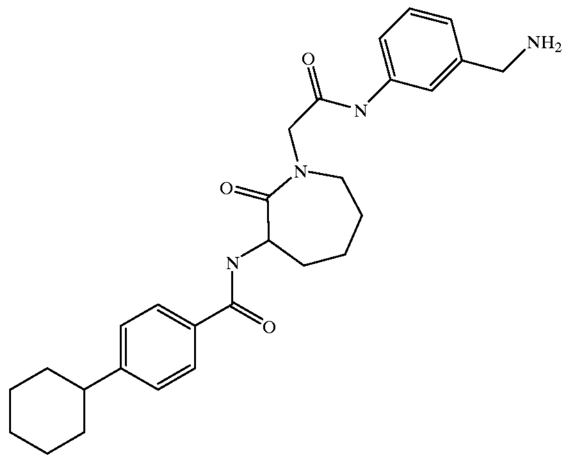 | 477 |
| 109 | 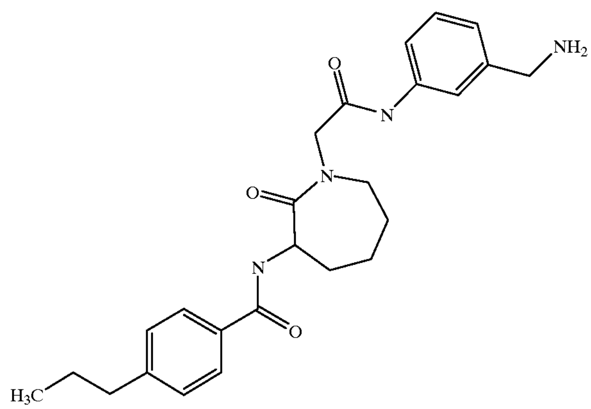 | 437 |
| 110 | 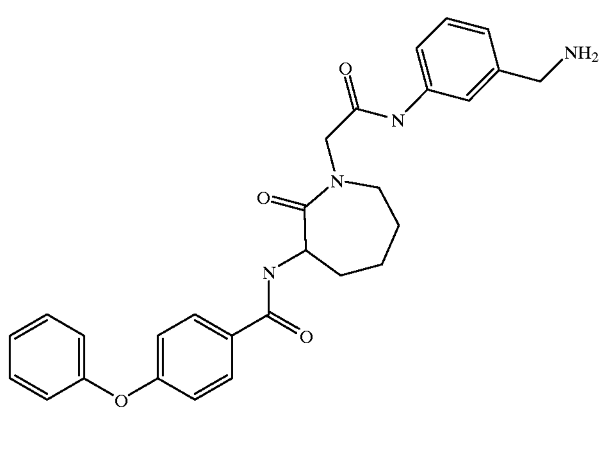 | 487 |

-continued

| Example No | Structure | Mass Spec. m/z (M + H)* |
|---|---|---|
| 111 | 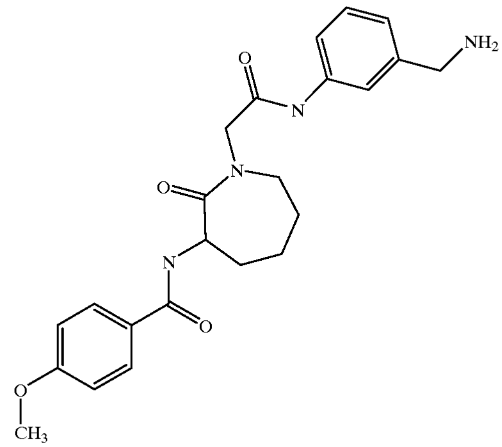 | 425 |
| 112 | 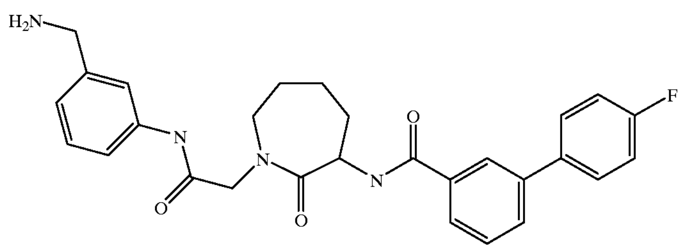 | 489 |
| 113 | 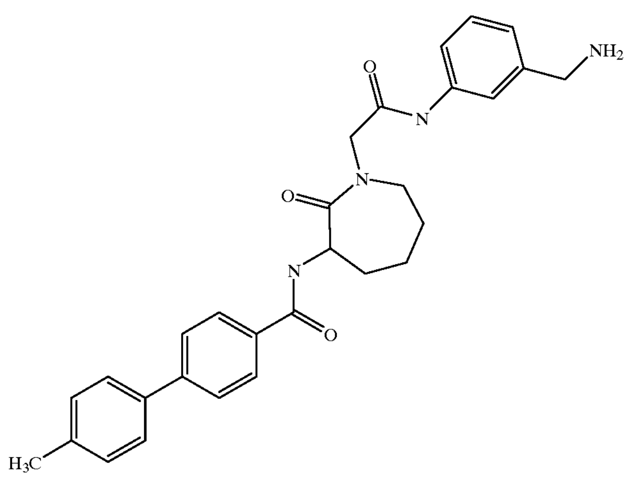 | 485 |

-continued

| Example No | Structure | Mass Spec. m/z (M + H)* |
|---|---|---|
| 114 | 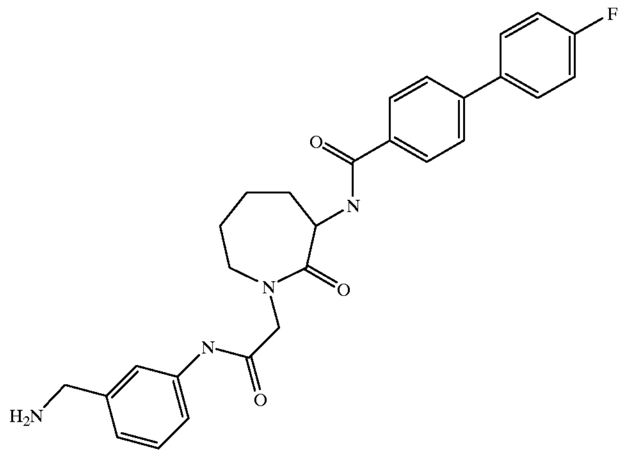 | 489 |
| 115 | 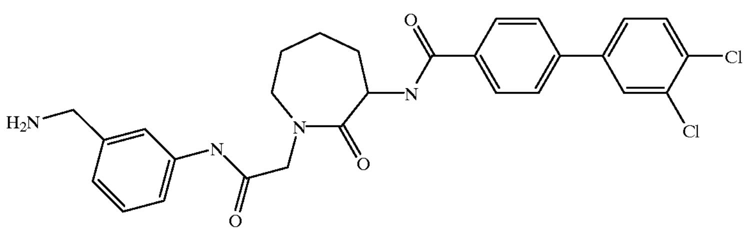 | 540 |
| 116 | 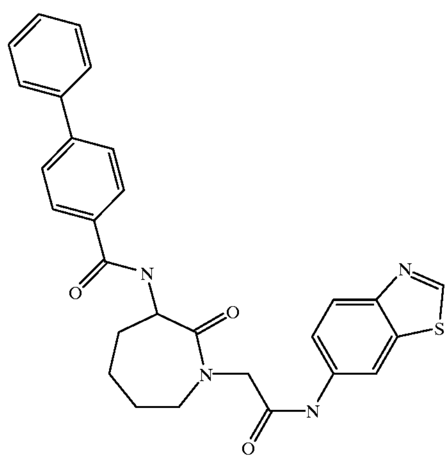 | 499 |
| 117 | 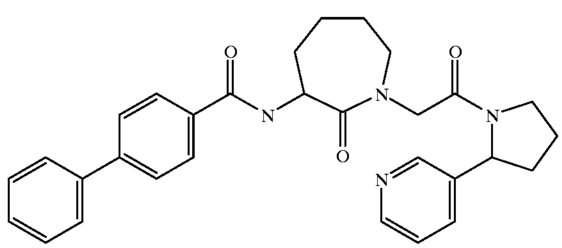 | 497 |

-continued
| Example No | Structure | Mass Spec. m/z (M + H)* |
|---|---|---|
| 118 | 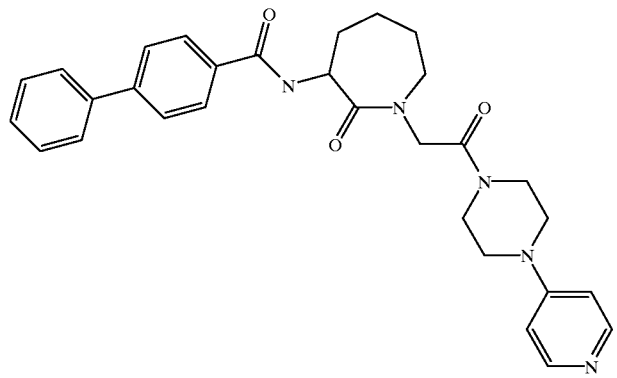 | 511 |
| 119 | 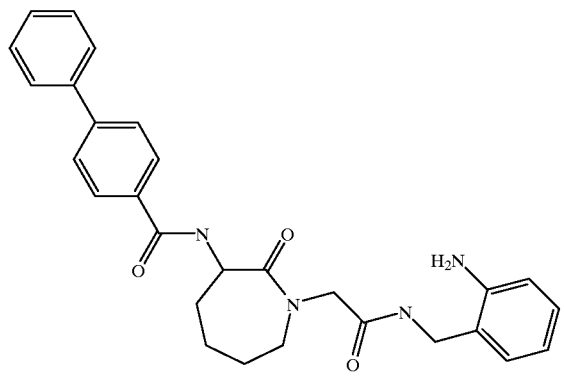 | 471 |
| 120 | 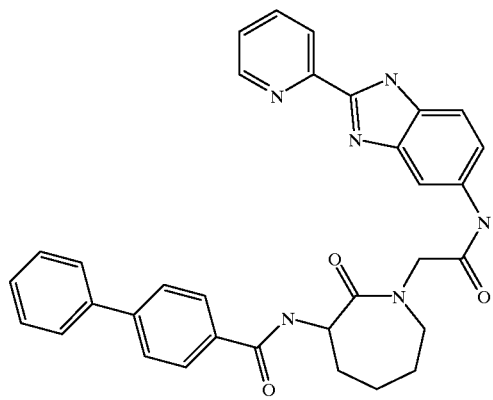 | 559 |

-continued
| Example No | Structure | Mass Spec. m/z (M + H)* |
|---|---|---|
| 121 | 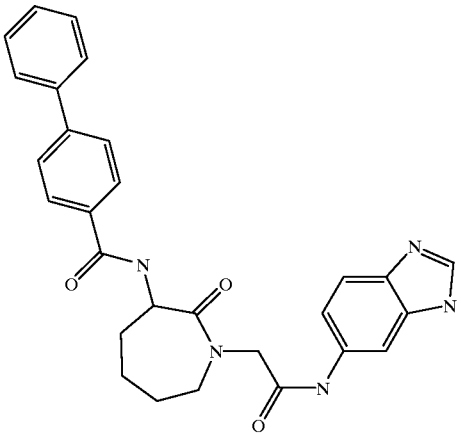 | 482 |
| 122 | 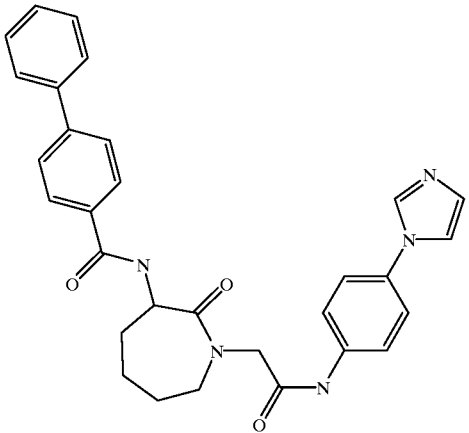 | 508 |
| 123 | 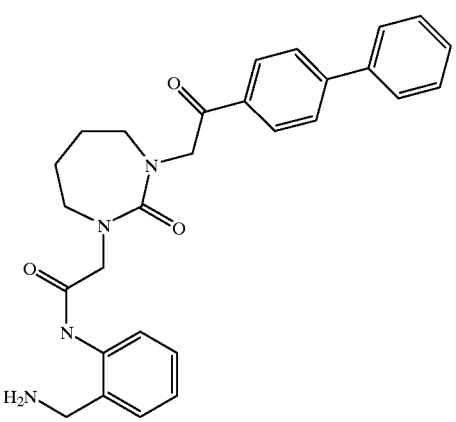 | 471 |

-continued

| Example No | Structure | Mass Spec. m/z (M + H)* |
|---|---|---|
| 124 | 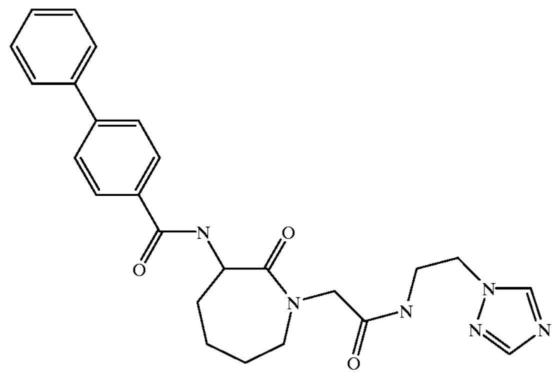 | 461 |
| 125 | 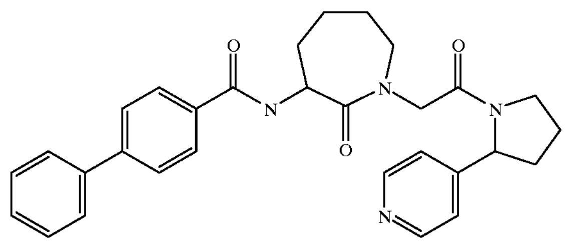 | 496 |
| 126 | 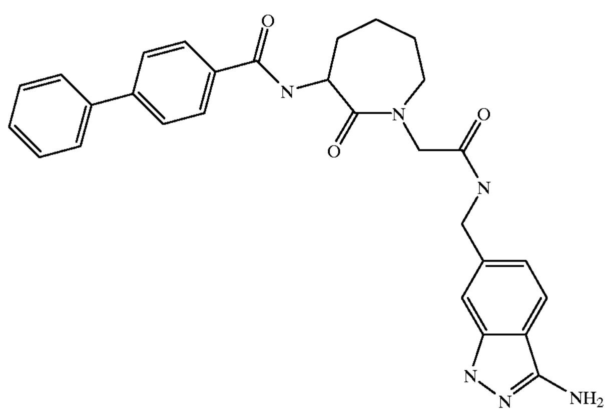 | 511 |
| 127 | 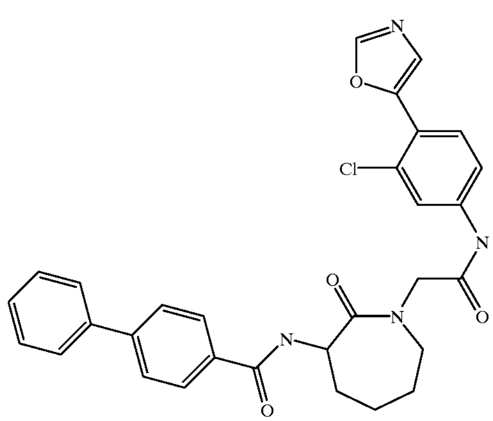 | 544 |

-continued

| Example No | Structure | Mass Spec. m/z (M + H)* |
|---|---|---|
| 128 | 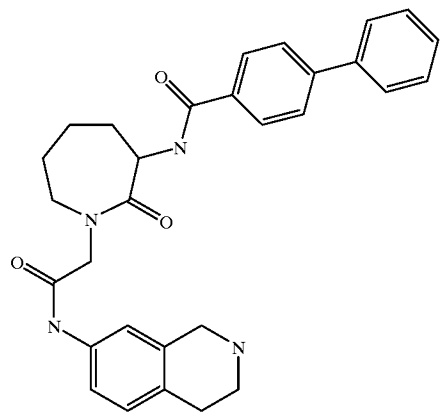 | 497 |
| 129 | 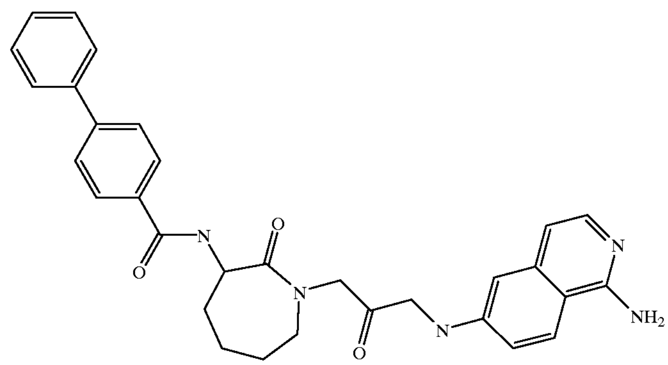 | 522 |
| 130 | 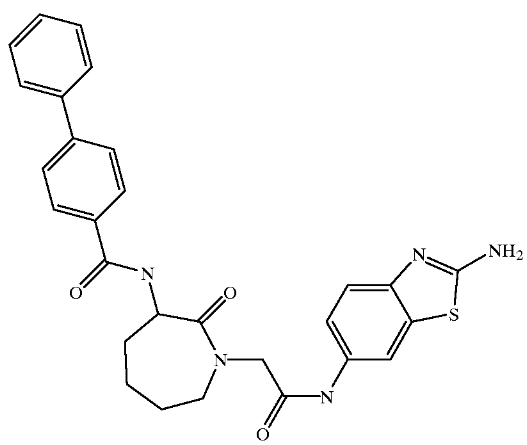 | 514 |
| 131 | 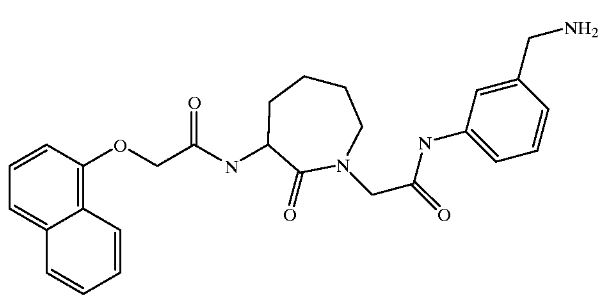 | 475 |

-continued

| Example No | Structure | Mass Spec. m/z (M + H)* |
|---|---|---|
| 132 | 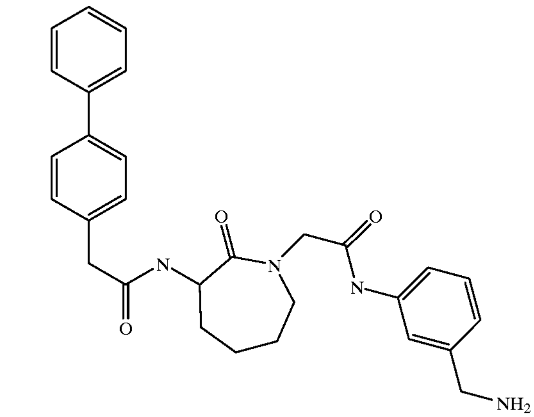 | 485 |
| 133 | 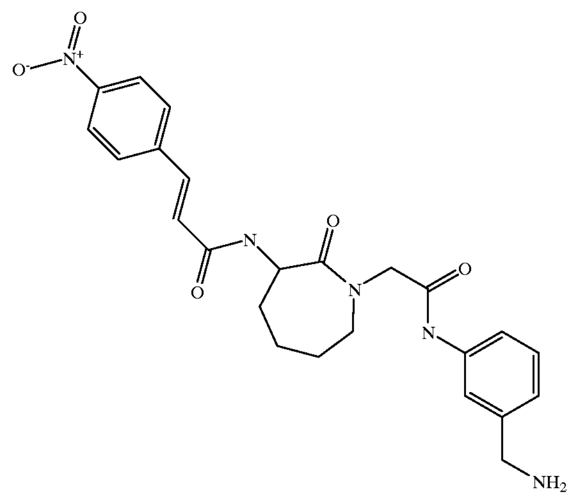 | 466 |
| 134 | 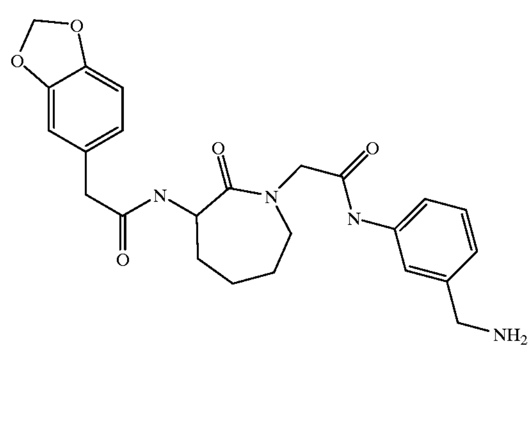 | 453 |

-continued

| Example No | Structure | Mass Spec. m/z (M + H)* |
|---|---|---|
| 135 | 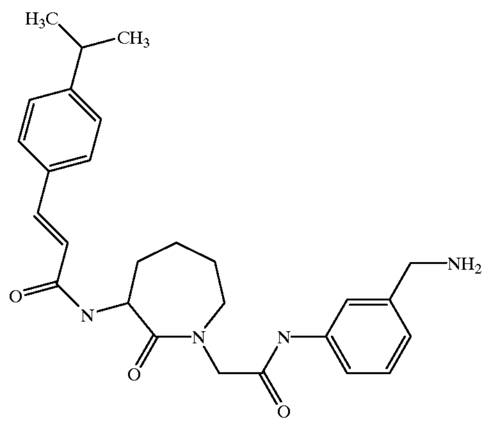 | 463 |
| 136 | 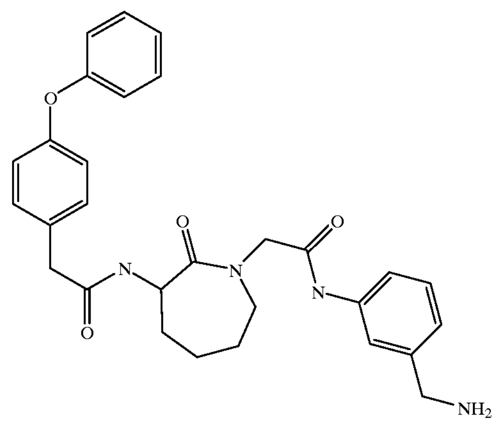 | 501 |
| 137 | 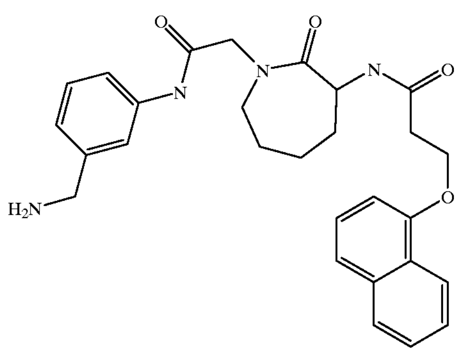 | 489 |
| 138 | 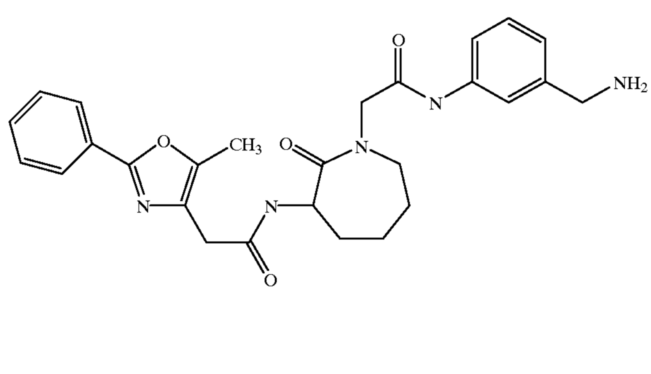 | 490 |

-continued
| Example No | Structure | Mass Spec. m/z (M + H)* |
|---|---|---|
| 139 | 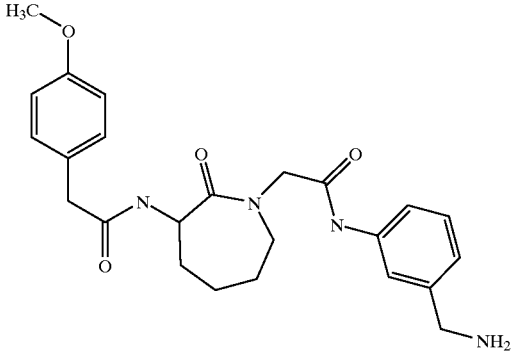 | 439 |
| 140 | 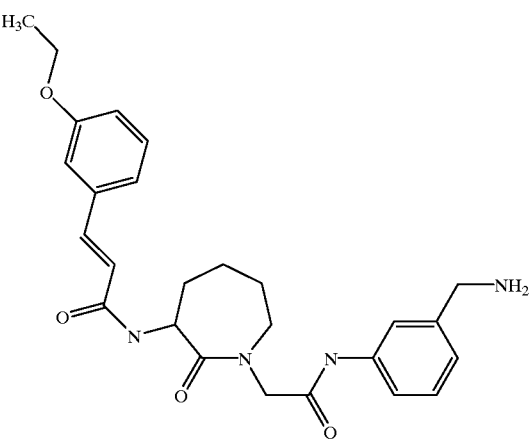 | 465 |
| 141 | 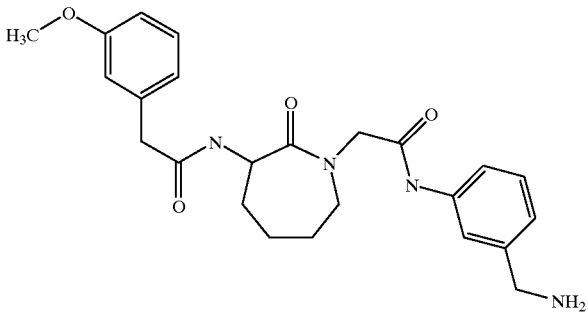 | 439 |
| 142 | 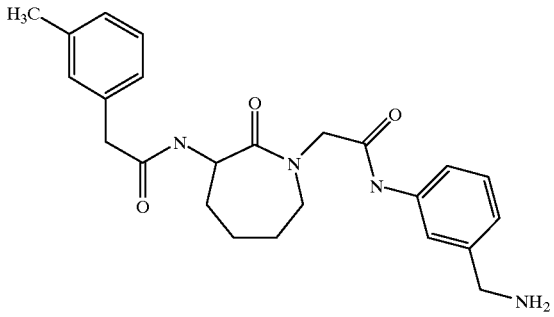 | 423 |

-continued

| Example No | Structure | Mass Spec. m/z (M + H)* |
|---|---|---|
| 143 | 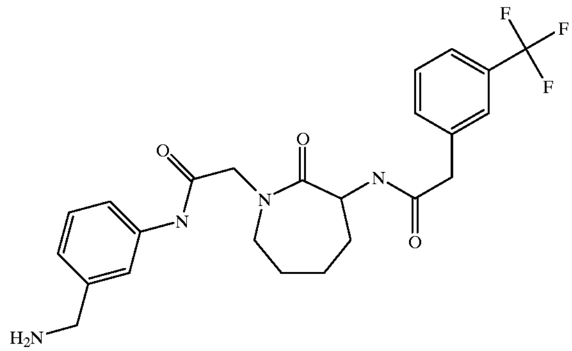 | 477 |
| 144 | 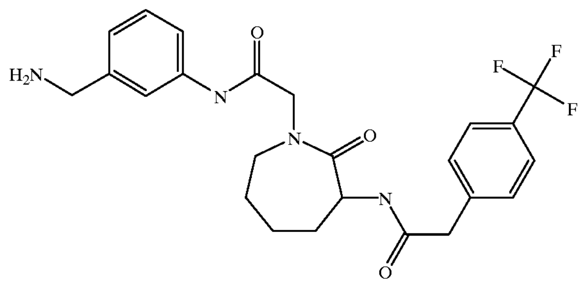 | 477 |
| 145 | 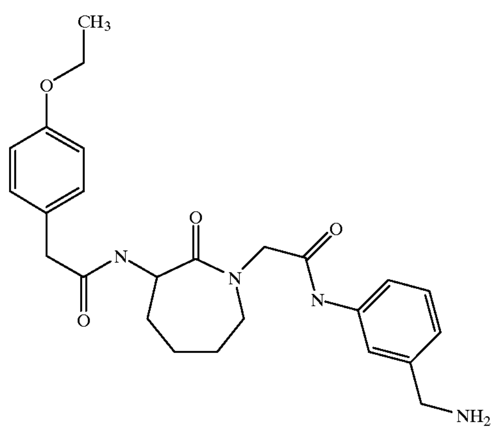 | 453 |
| 146 | 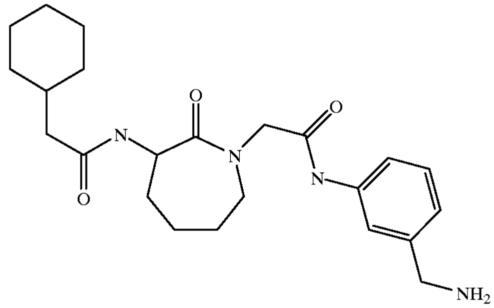 | 415 |

-continued

| Example No | Structure | Mass Spec. m/z (M + H)* |
|---|---|---|
| 147 | 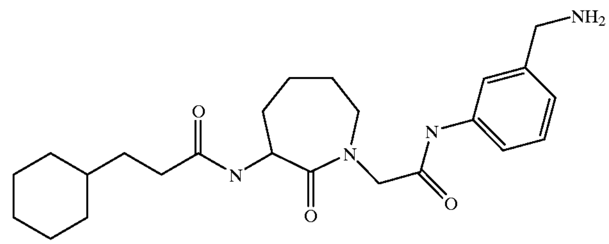 | 429 |
| 148 | 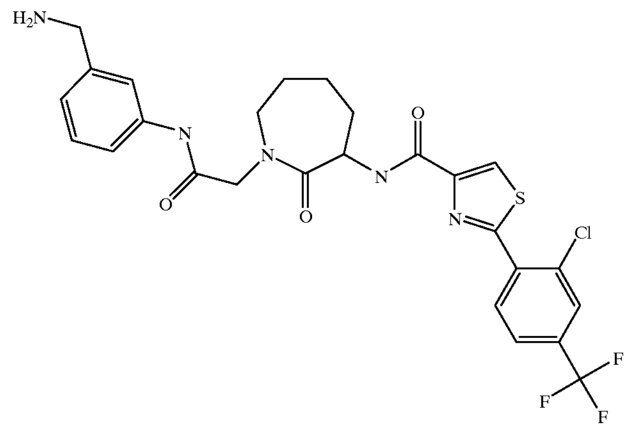 | 581 |
| 149 | 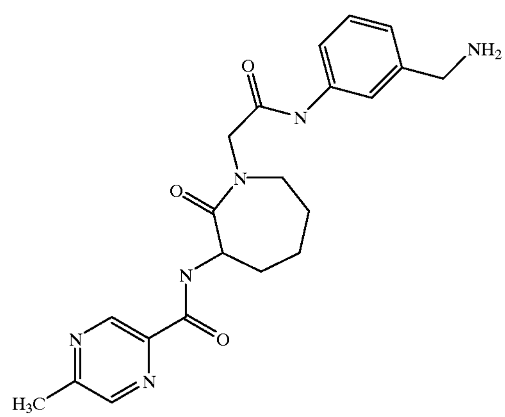 | 411 |
| 150 | 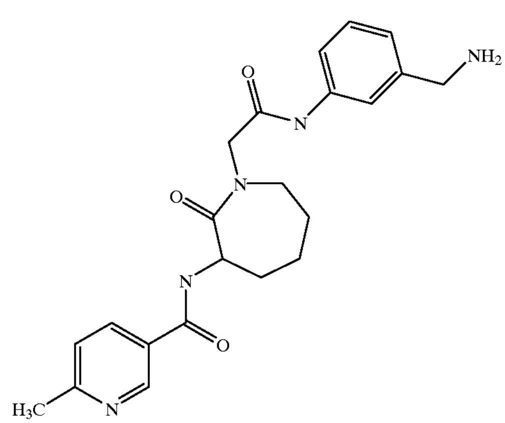 | 410 |

-continued

| Example No | Structure | Mass Spec. m/z (M + H)* |
|---|---|---|
| 151 | 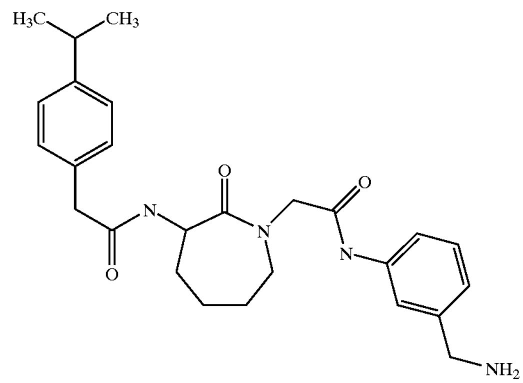 | 451 |
| 152 | 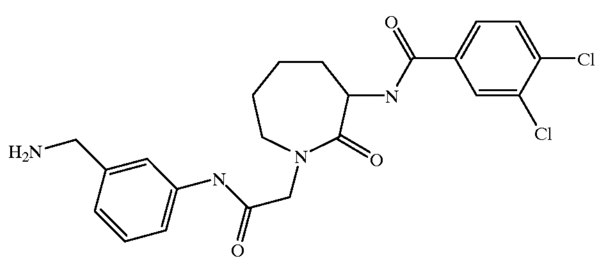 | 464 |
| 153 | 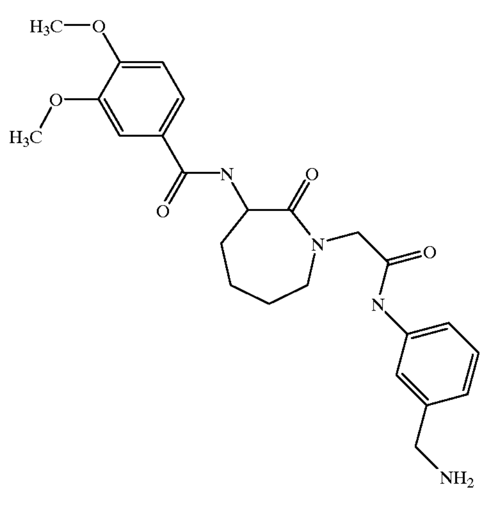 | 455 |

-continued

| Example No | Structure | Mass Spec. m/z (M + H)* |
|---|---|---|
| 154 | 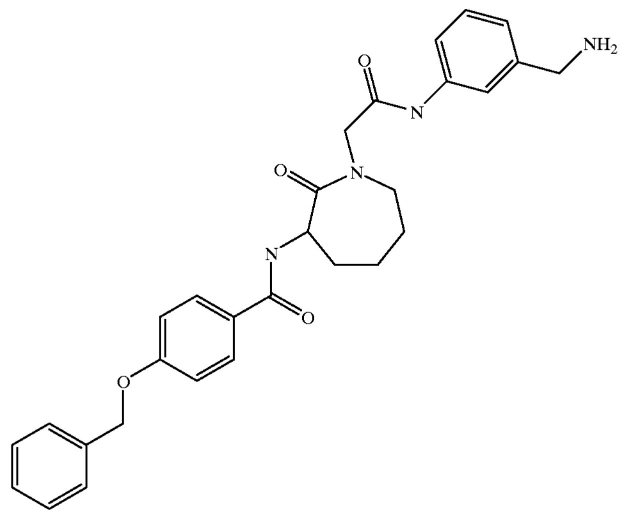 | 501 |
| 155 | 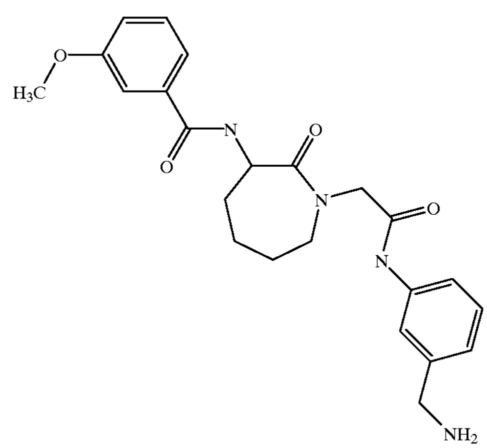 | 425 |
| 156 | 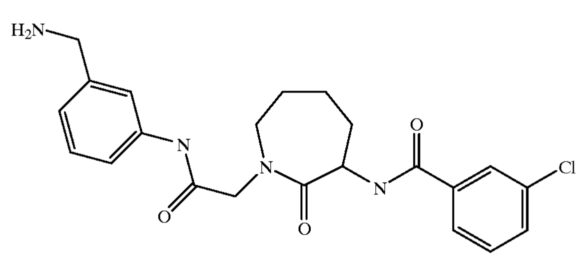 | 429 |

-continued

| Example No | Structure | Mass Spec. m/z (M + H)* |
|---|---|---|
| 157 | 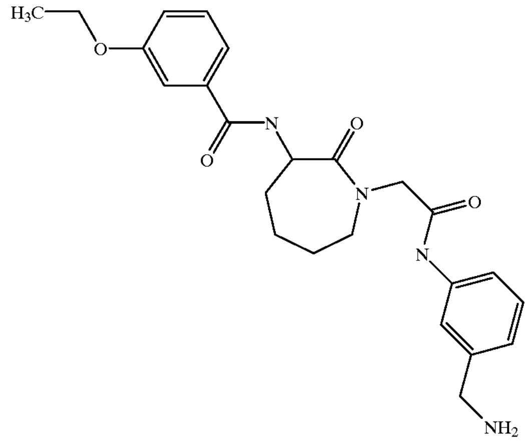 | 439 |
| 158 | 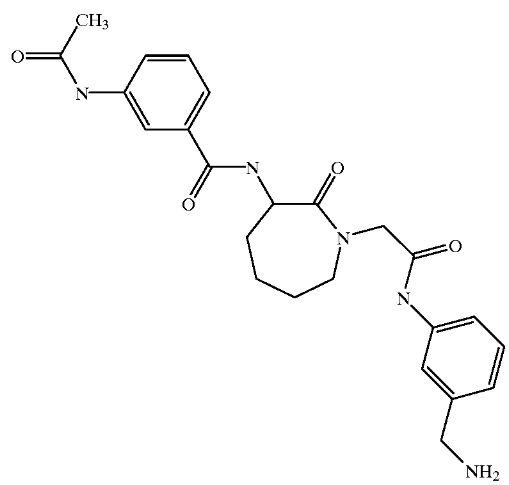 | 452 |
| 159 | 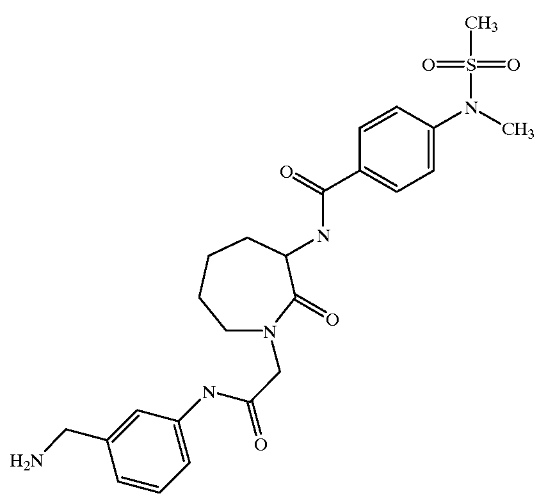 | 502 |

-continued
| Example No | Structure | Mass Spec. m/z (M + H)* |
|---|---|---|
| 160 | 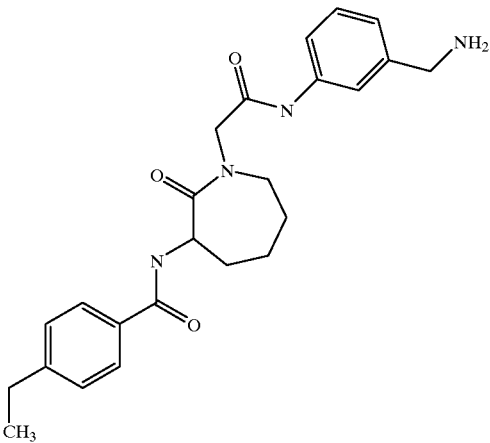 | 423 |
| 161 | 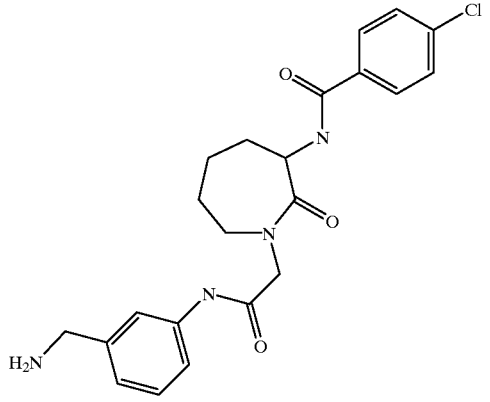 | 429 |
| 162 | 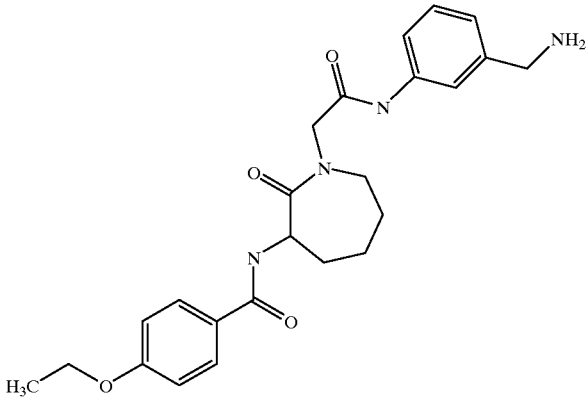 | 439 |

| Example No | Structure | Mass Spec. m/z (M + H)* |
|---|---|---|
| 163 | 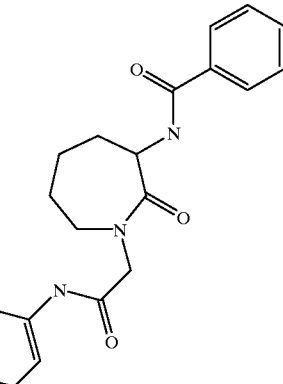 | 473 |
| 164 | 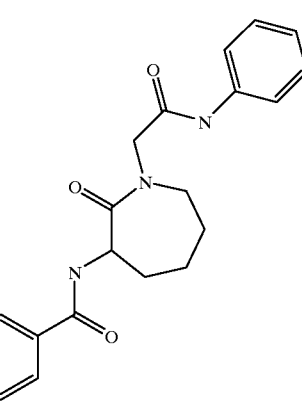 | 452 |
| 165 | 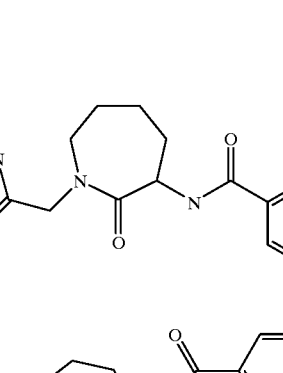 | 463 |
| 166 | 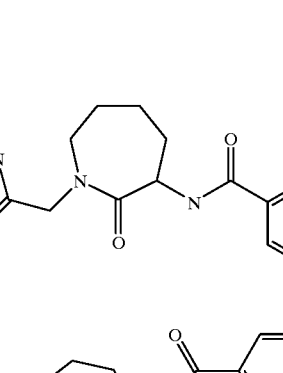 | 522 |

| Example No | Structure | Mass Spec. m/z (M + H)* |
|---|---|---|
| 167 | 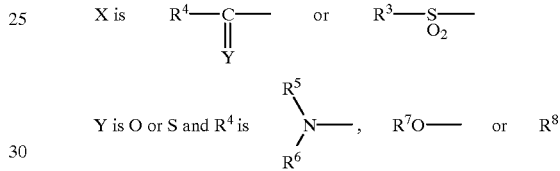 | 501 |

What is claimed is:
1. A compound having the formula

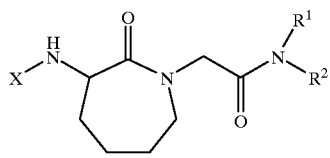

or pharmaceutically acceptable salts thereof or all stereoisomers thereof, wherein $R^1$ and $R^2$ are the same or different and are independently selected from hydrogen, alkyl, alkenyl, alkynyl, aryl, aminoalkylaryl, aminocycloalkylalkyl, aminoalkyl, aminoalkylcycloalkyl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, or polycycloalkenylalkyl, or $R^1$ and $R^2$ can be taken with the nitrogen to which they are attached to form a cycloheteroalkyl ring; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, aminoalkyl, alkyloxycarbonylaminoalkyl, arylalkyloxycarbonylaminoalkyl, alkylcarbonyl, arylcarbonyl, arylaminocarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

X is $R^4-\underset{Y}{\overset{\|}{C}}-$ or $R^3-\underset{O_2}{\overset{\|}{S}}-$ Y is O or S and $R^4$ is $\underset{R^6}{\overset{R^5}{N}}-$, $R^7O-$ or $R^8$ $R^3$ is selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, or polycycloalkenylalkyl; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

$R^5$ and $R^6$ are the same or different and are independently selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, polycycloalkenylalkyl, arylcarbonyl, alkylcarbonyl, alkoxycarbonyl, aryloxycarbonyl, arylsulfonyl, or alkylsulfonyl, or $R^5$ and $R^6$ can be taken with the nitrogen to which they are attached to form a cycloheteroalkyl ring; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

$R^7$ and $R^8$ are the same or different and are independently selected from alkyl, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloheteroalkyl, cycloalkenylalkyl, polycycloalkenyl, polycycloalkenylalkyl, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl;

with the proviso that where

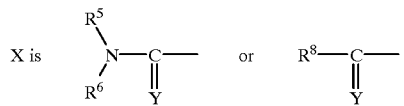

and (I) $R^1$ and $R^2$ are independently cycloalkyl, alkenyl, phenyl, benzyl, cyanoalkyl, alkoxycarbonylalkyl, or phenyl mono- or disubstituted with lower alkyl, cyano, hydroxy, dialkylamino, alkoxy, benzyloxy, alkylamino, alkoxycarbonyl, pyrrolidino, morpholino, halogen, alkyl substituted with one or more fluorines, then Y is S;

(2) where $R^1$ and $R^2$ are alkyl, then Y is S; and (3) where one of $R^1$ and $R^2$ is alkyl and Y is O, then the other is alkynyl, heteroaryl, heteroarylalkyl, cycloalkenyl, cycloheteroalkyl, heteroaryloxy, cycloalkenylalkyl, polycycloalkenyl, polycycloalkenylalkyl or $R^1$ and $R^2$ can be taken with the nitrogen to which they are attached to form a cycloheteroalkyl ring, all optionally substituted through available carbon atoms with 1, 2, 3 or 4 substituents as defined for $R^1$ and $R^2$.

2. The compound as defined in claim 1 having the formula

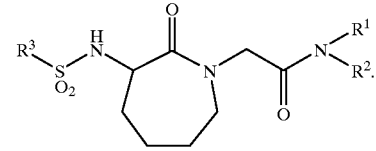

3. The compound as defined in claim 1 having the formula

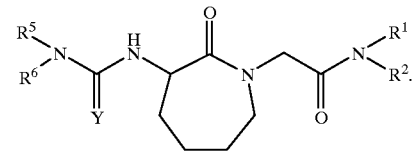

4. The compound as defined in claim 1 having the formula

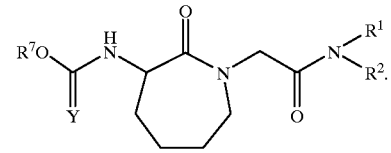

5. The compound as defined in claim 1 having the formula

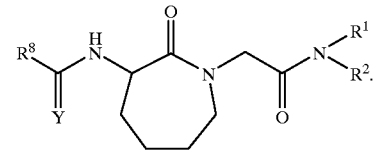

6. The compound as defined in claim 1 wherein

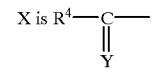

and Y is S.

7. The compound as defined in claim 3 wherein Y is S.

8. The compound as defined in claim 3 wherein $R^1$ and $R^2$ together with the nitrogen to which they are attached form a cycloheteroalkyl ring, Y is S, one of $R^5$ and $R^6$ is hydrogen and the other of $R^5$ and $R^6$ is aryl, alkylaryl or alkoxyaryl.

9. The compound as defined in claim 8 wherein $R^1$ and $R^2$ together with the nitrogen to which they are attached form a pyrrolidinyl ring, Y is S, one of $R^5$ and $R^6$ is hydrogen and the other of $R^5$ and $R^6$ is phenyl, 3-methylphenyl, 3-methoxyphenyl, 4-cyanophenyl, 3-fluorophenyl, 3-chlorophenyl, 4-chlorophenyl, 4-methoxyphenyl, 3-chloro-4-methylphenyl, 3,5-dichlorophenyl, 3-iodophenyl, 3,5-dimethylphenyl or naphthyl.

10. The compound as defined in claim 1 having the structure

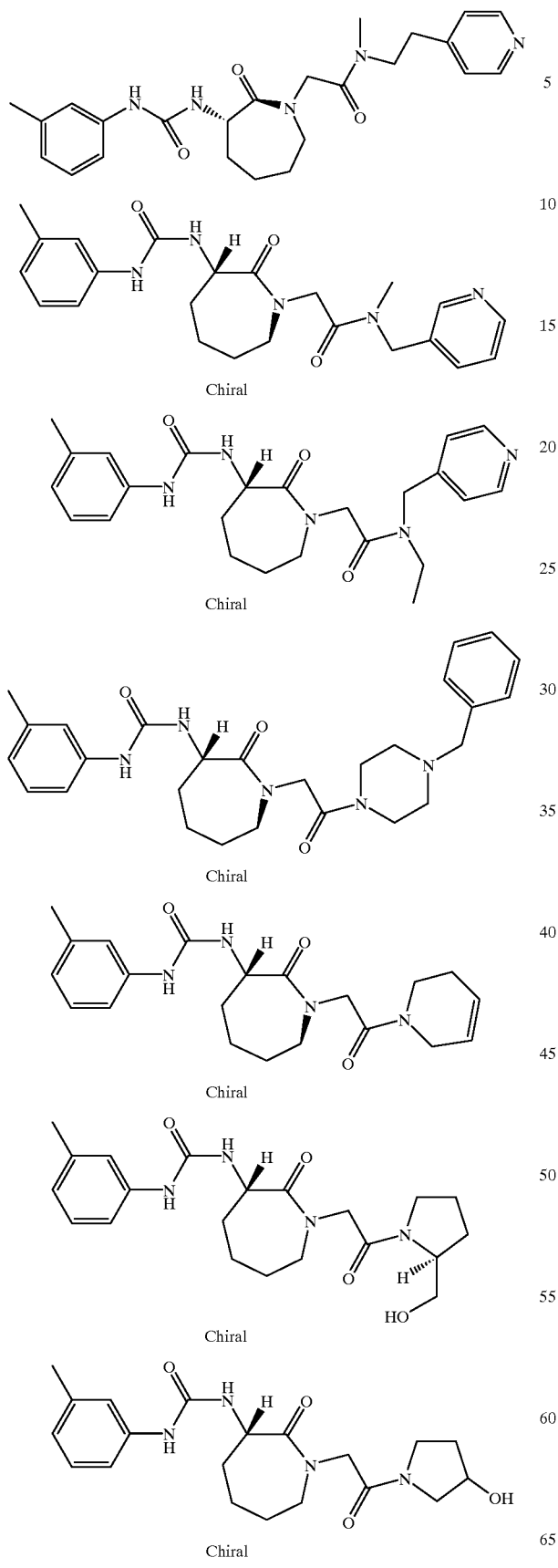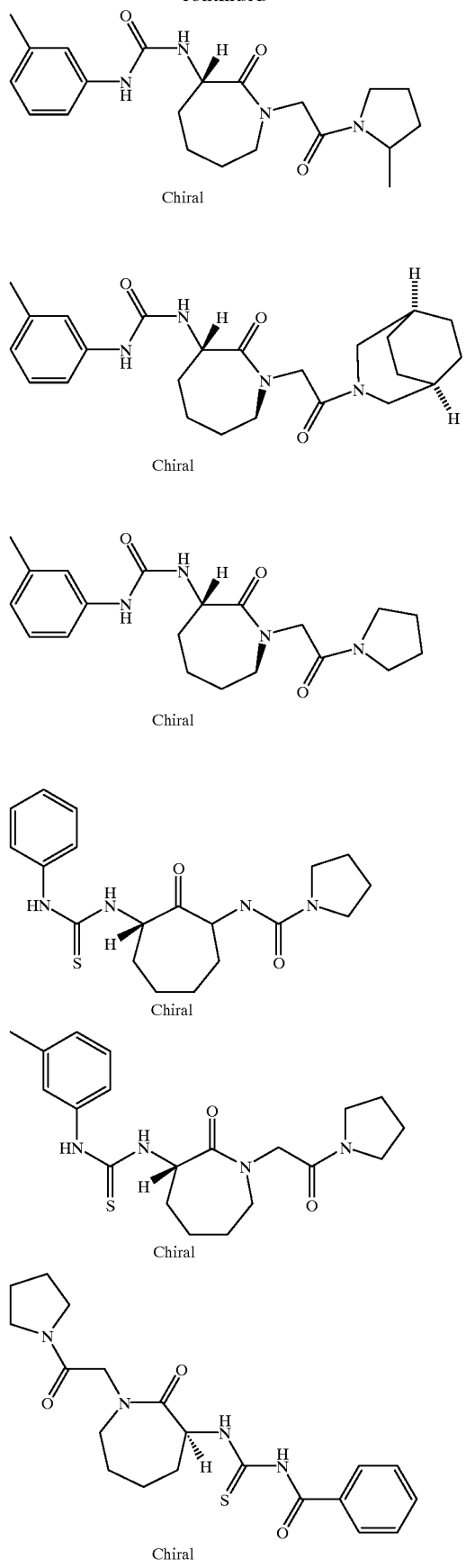

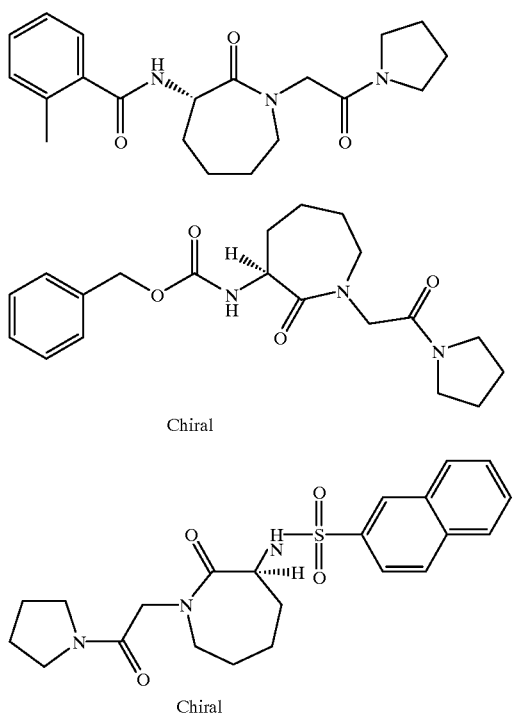
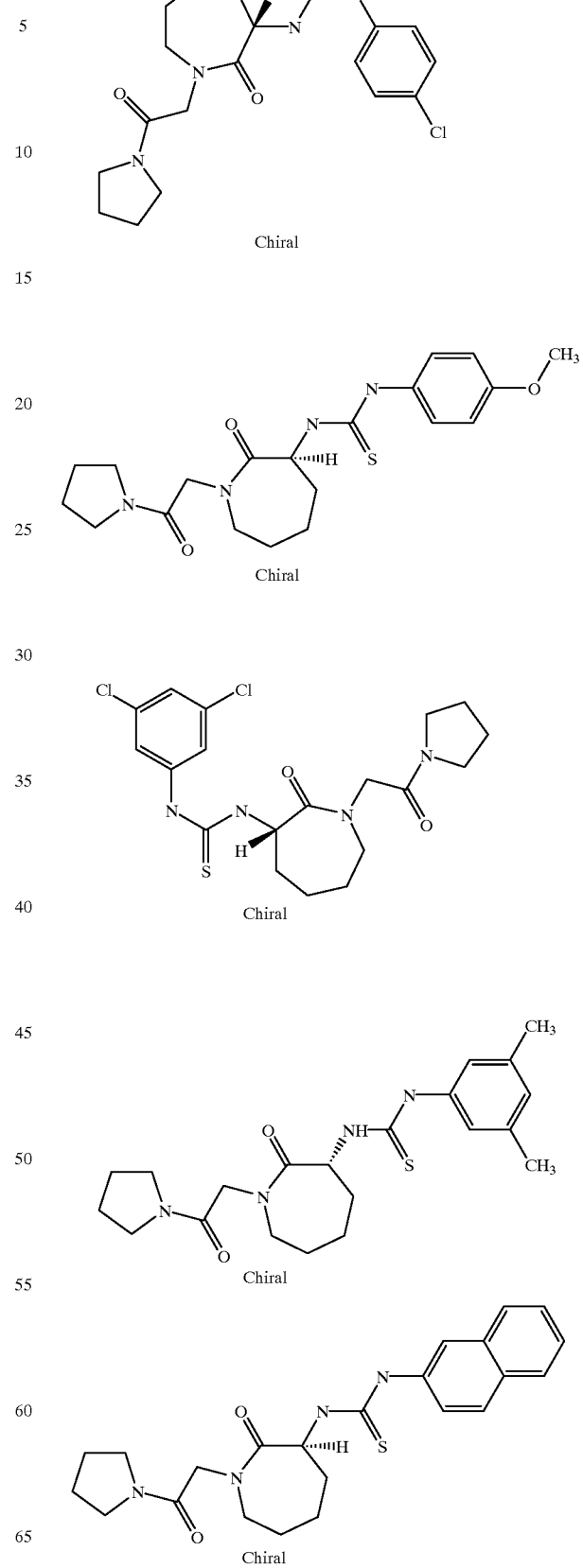

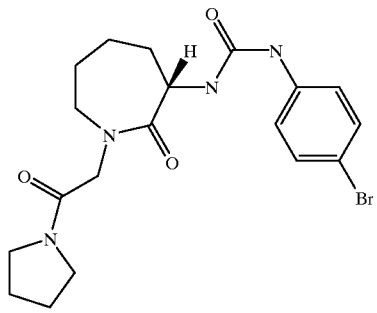
Chiral
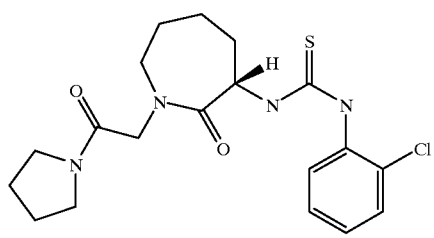
Chiral
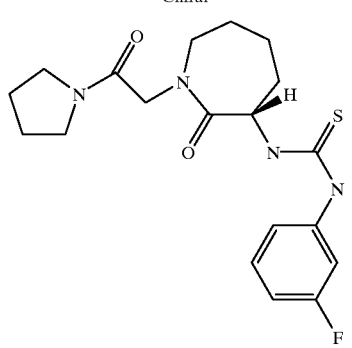
Chiral
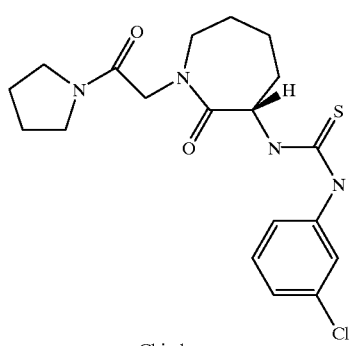
Chiral
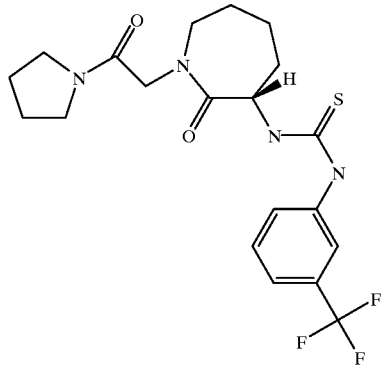
Chiral
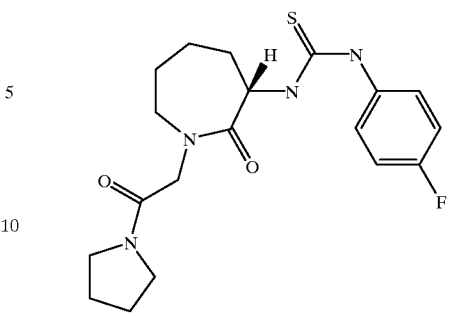
Chiral
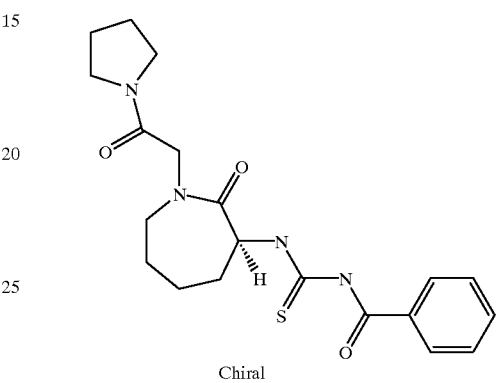
Chiral
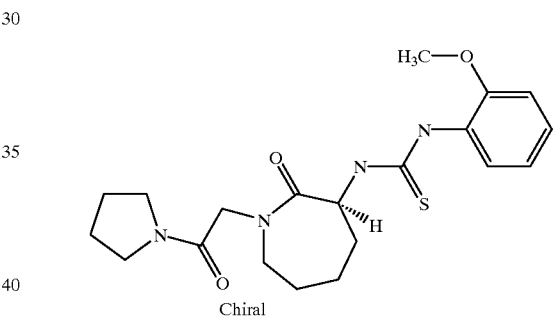
Chiral
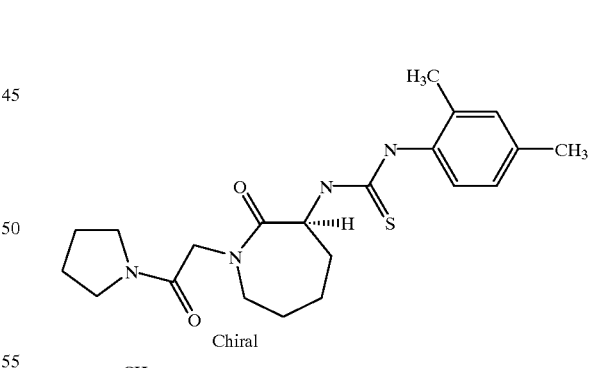
Chiral
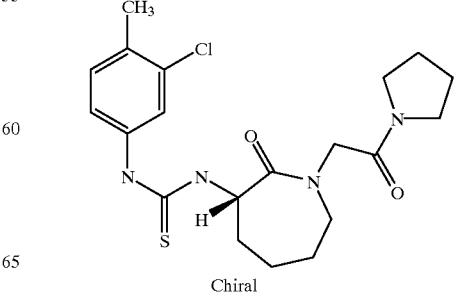
Chiral

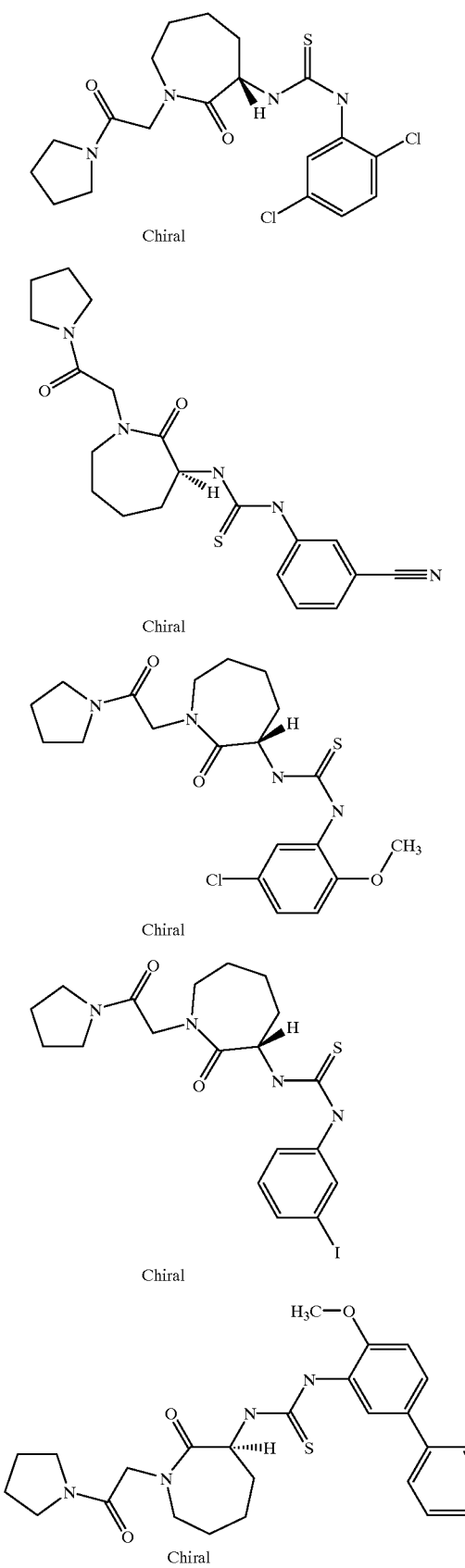
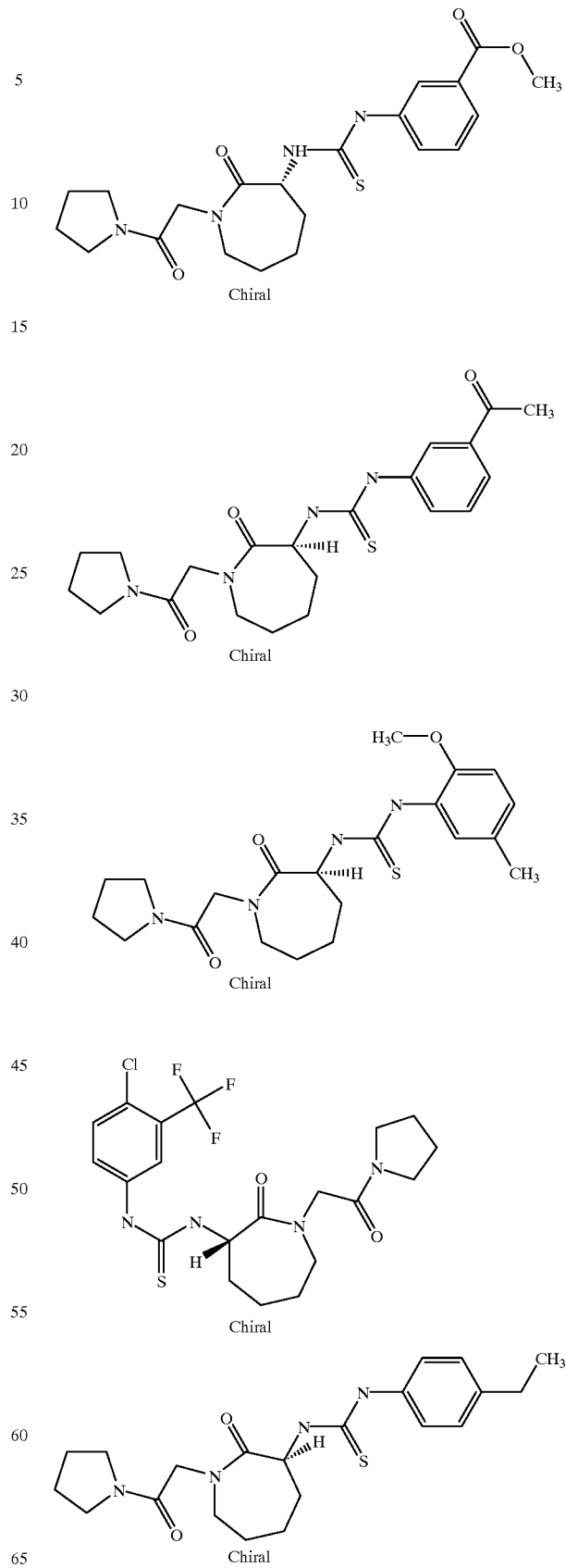

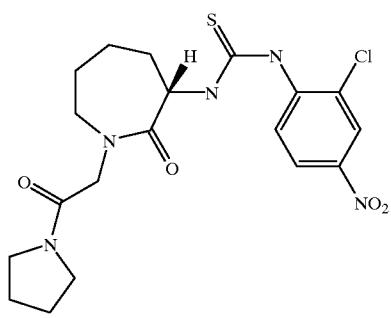
Chiral
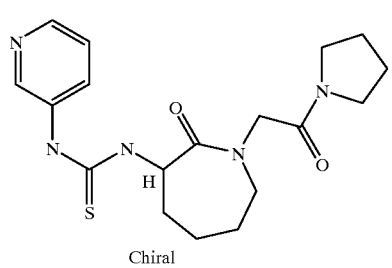
Chiral
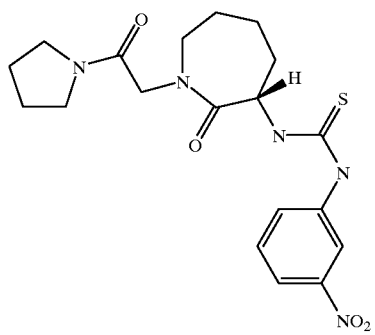
Chiral
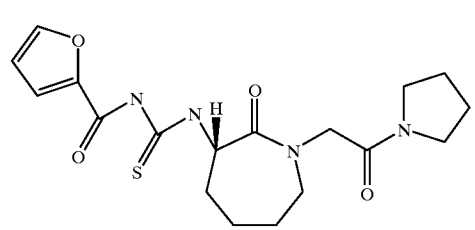
Chiral
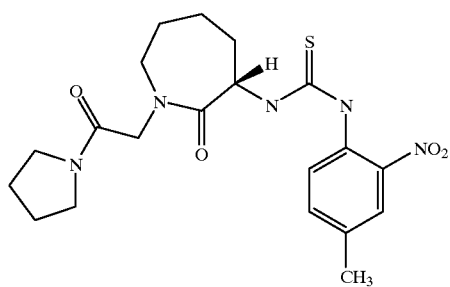
Chiral
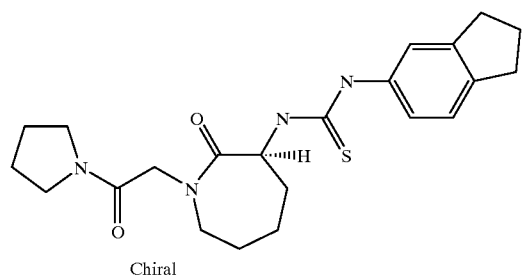
Chiral
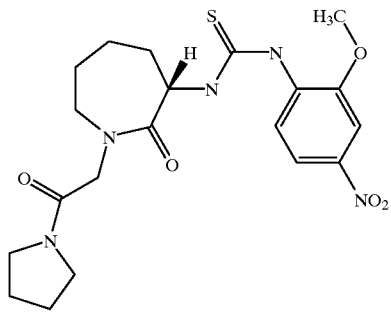
Chiral
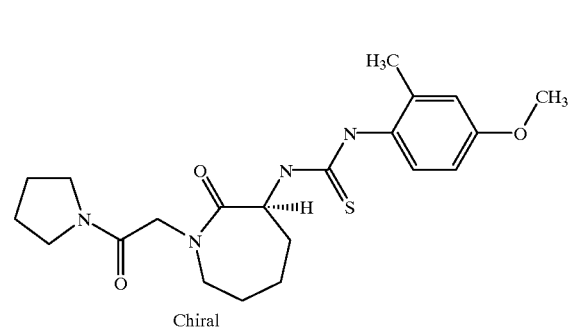
Chiral
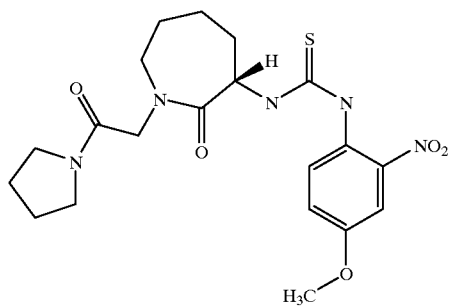
Chiral
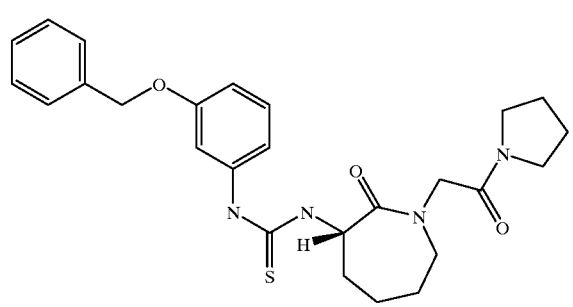
Chiral

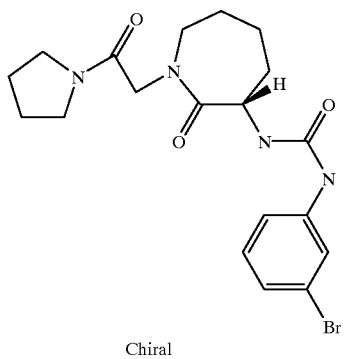
Chiral
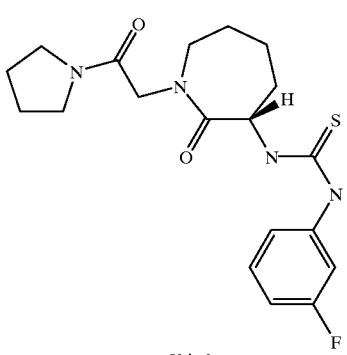
Chiral
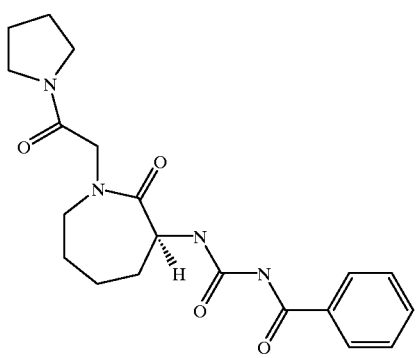
Chiral
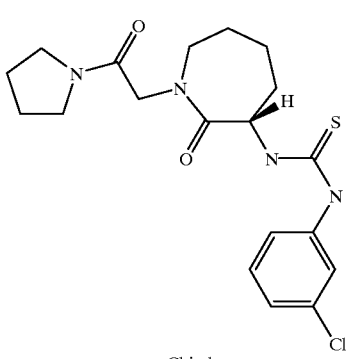
Chiral
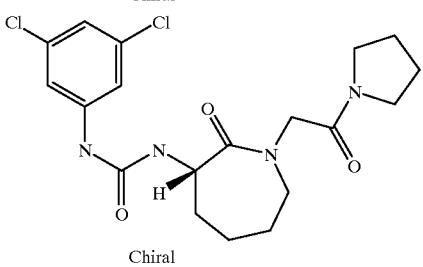
Chiral
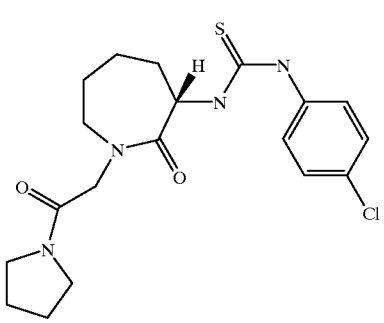
Chiral
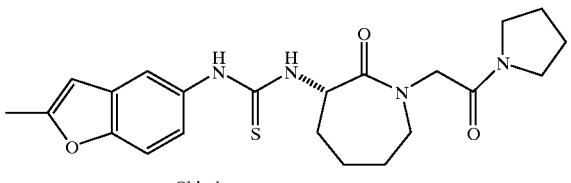
Chiral
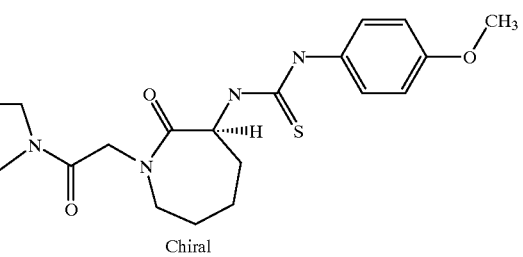
Chiral
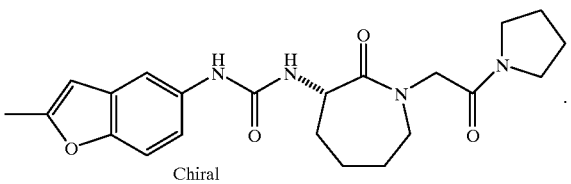
Chiral
11. The compound as defined in claim 1 having the structure.
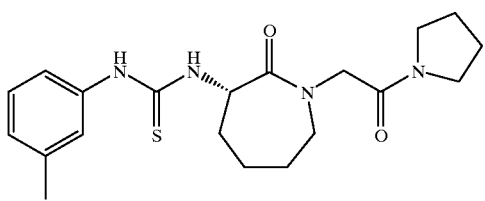
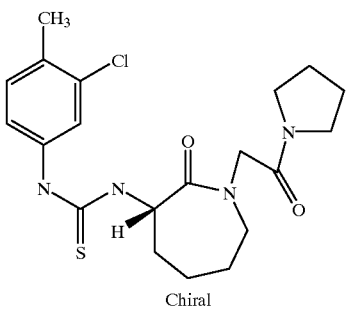
Chiral

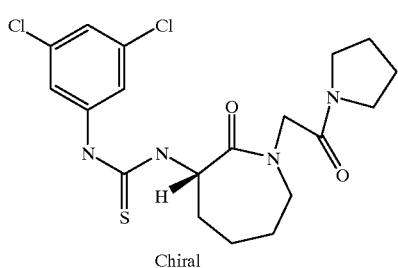

Chiral

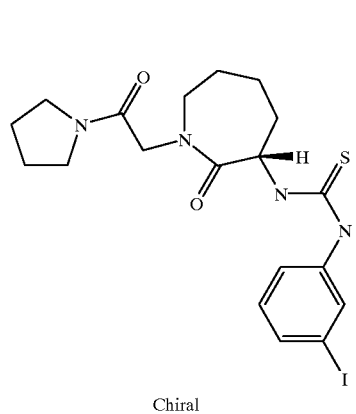

Chiral

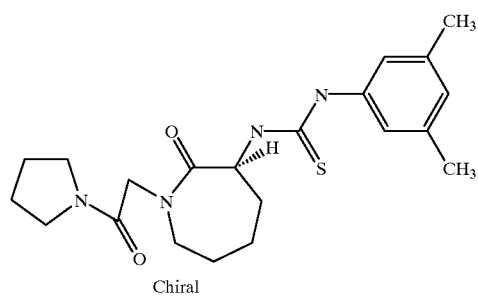

Chiral

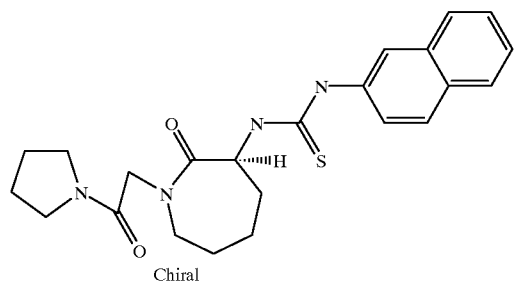

Chiral

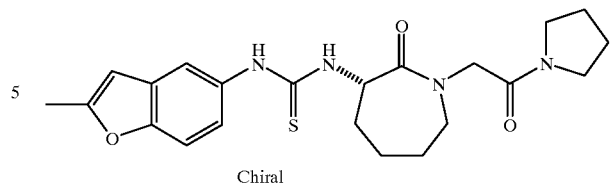

Chiral

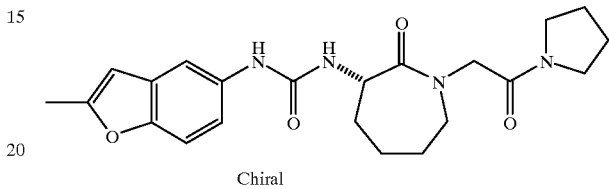

Chiral

12. The compound as defined in claim 1 wherein at least one of $R^1$ and $R^2$ is other than hydrogen.

13. The compound as defined in claim q wherein Y is O.

14. The compound as defined in claim 5 wherein Y is O.

15. The compound as defined in claim 5 wherein at one of $R^1$ and $R^2$ is hydrogen and Y is O.

16. The compound as defined in claim 5 wherein one of $R^1$ and $R^2$ is hydrogen and the other is aminoalkylaryl or aminocycloalkylalkyl.

17. The compound as defined in claim 16 wherein one of $R^1$ and $R^2$ is

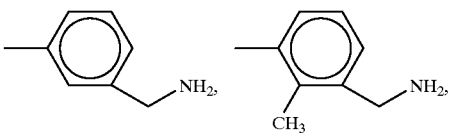

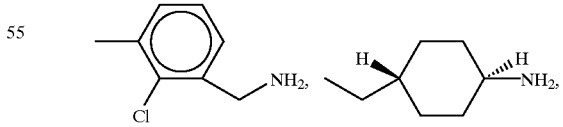

Y is O.

18. The compound as defined in claim 1 having the structure

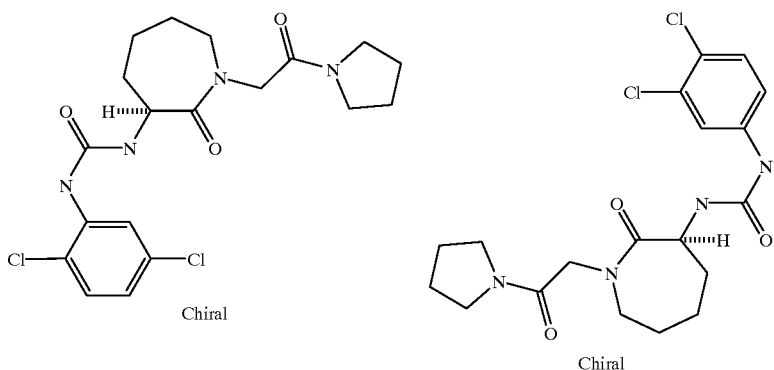
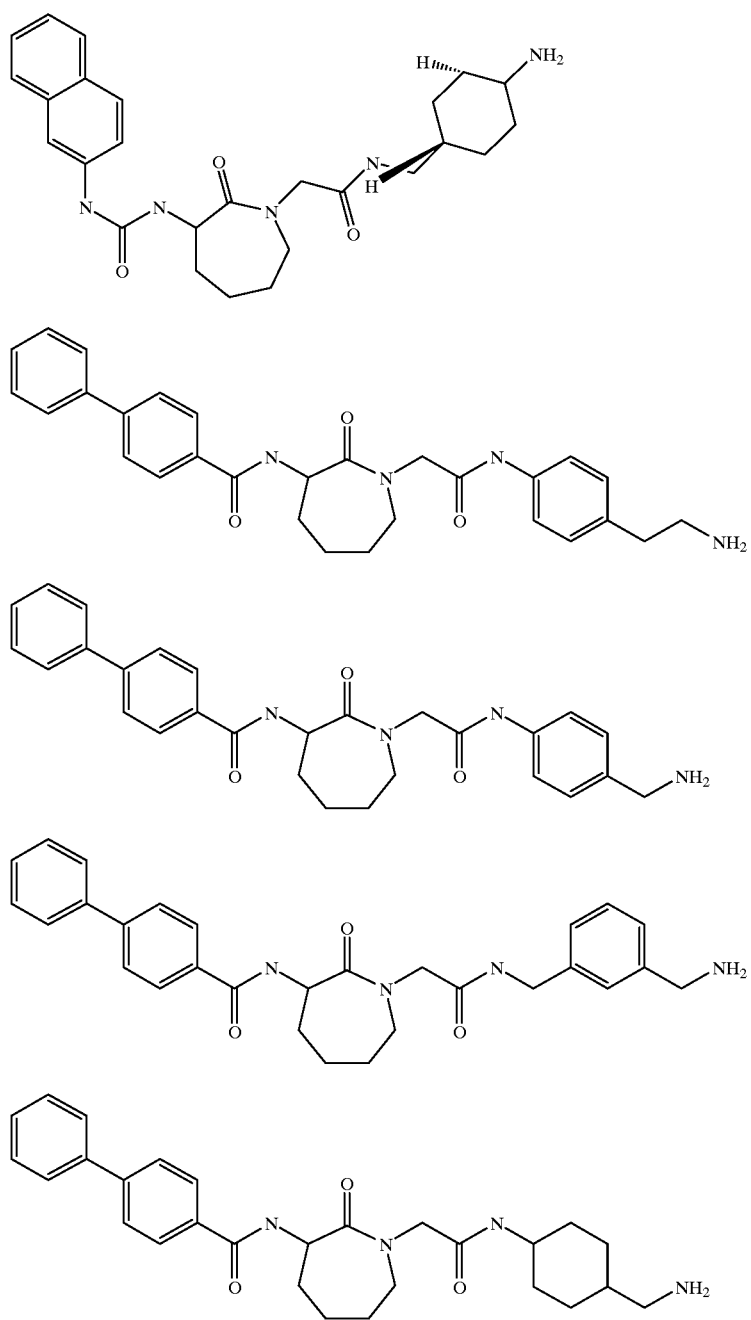

-continued
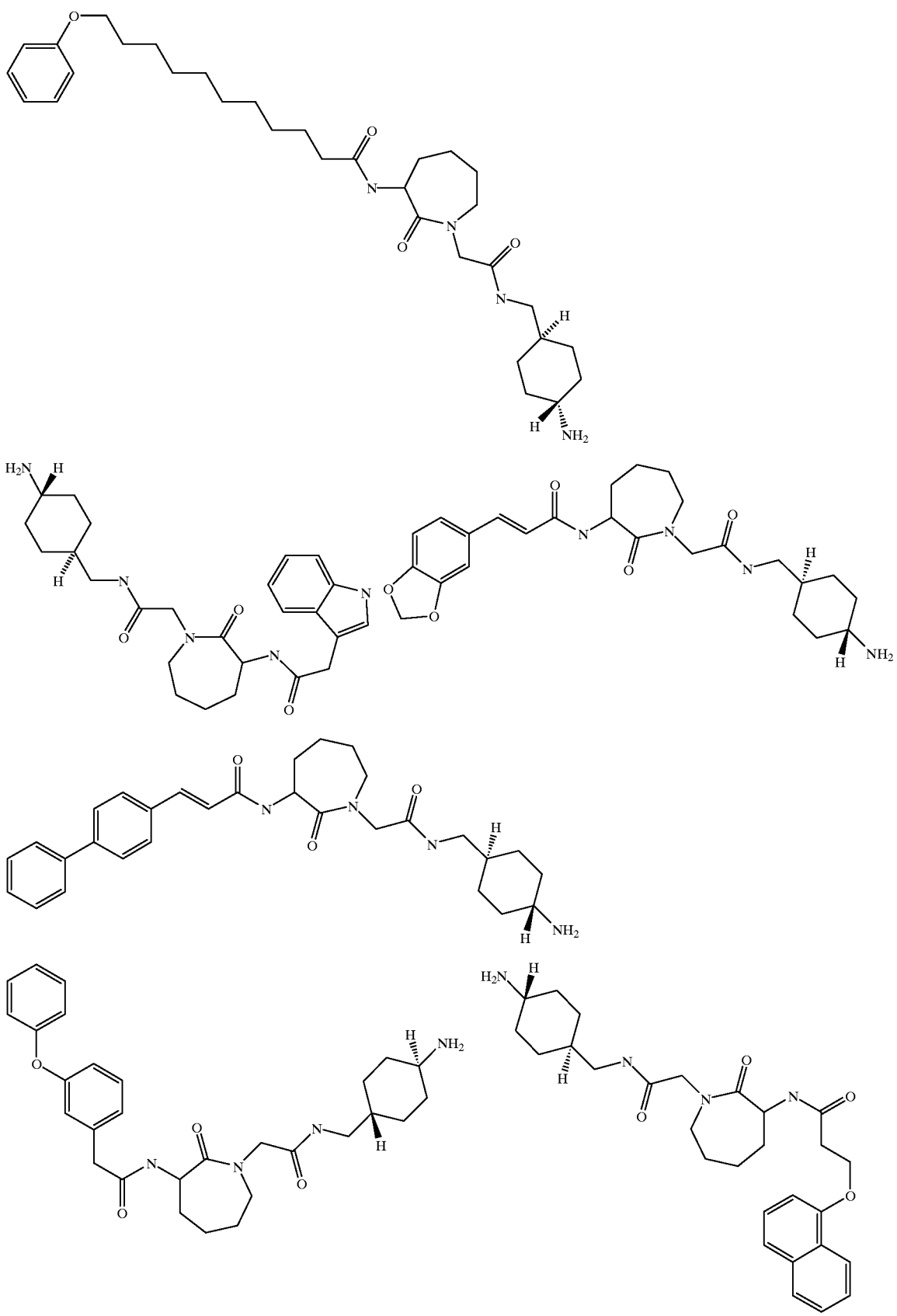

-continued
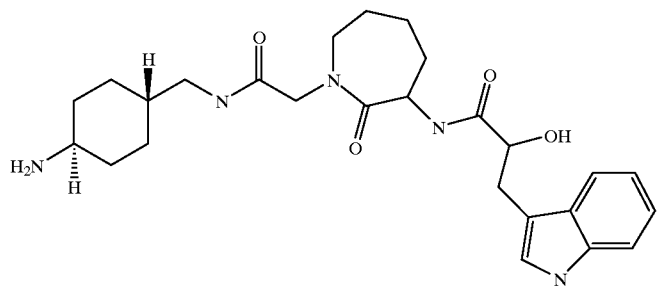
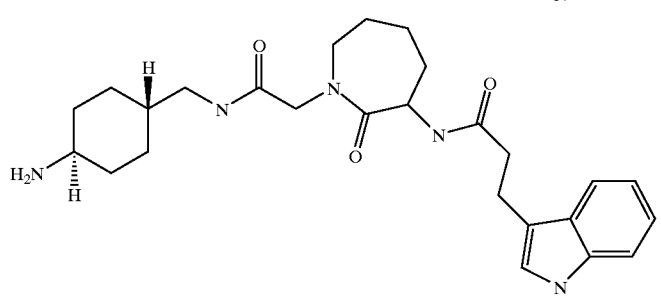
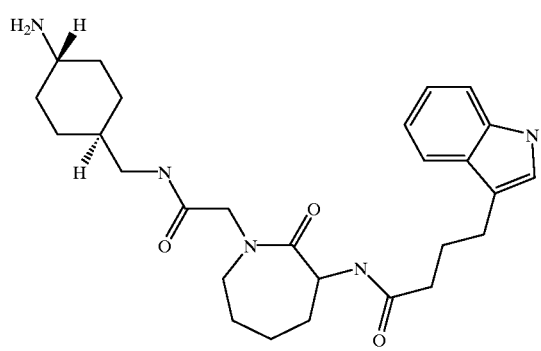
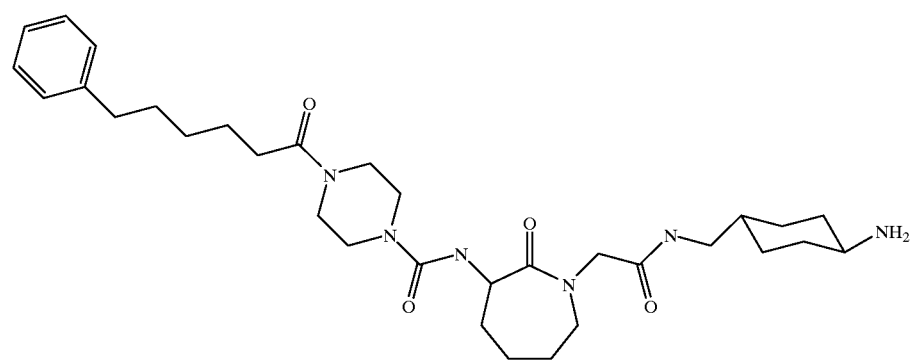
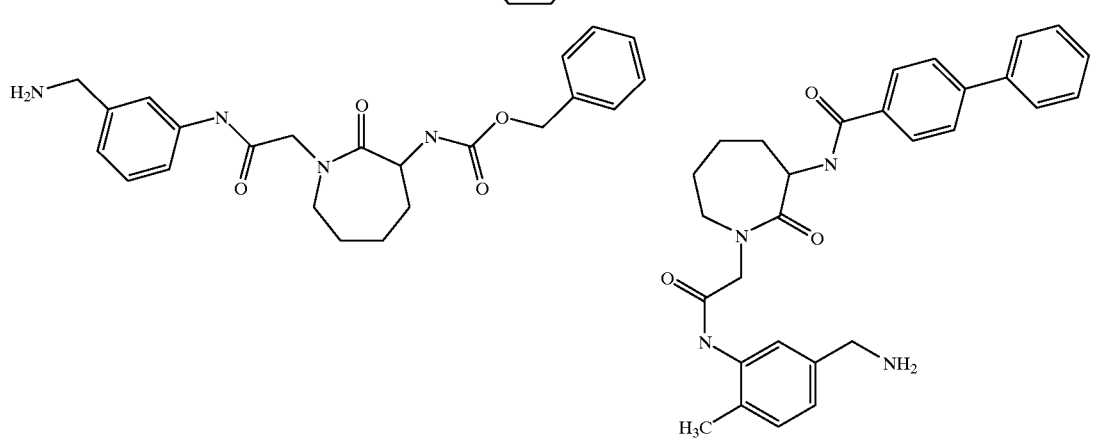

157 158
-continued
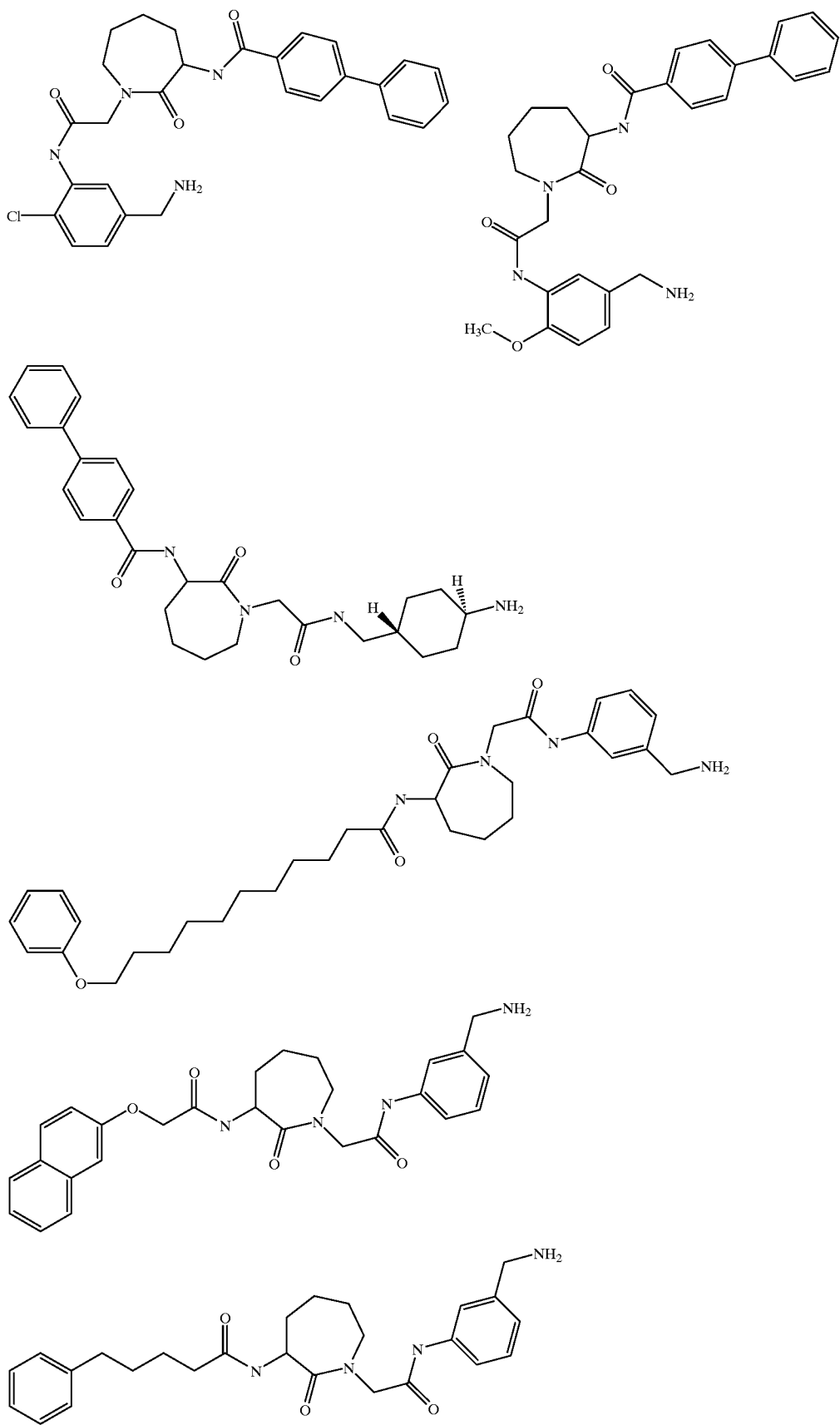

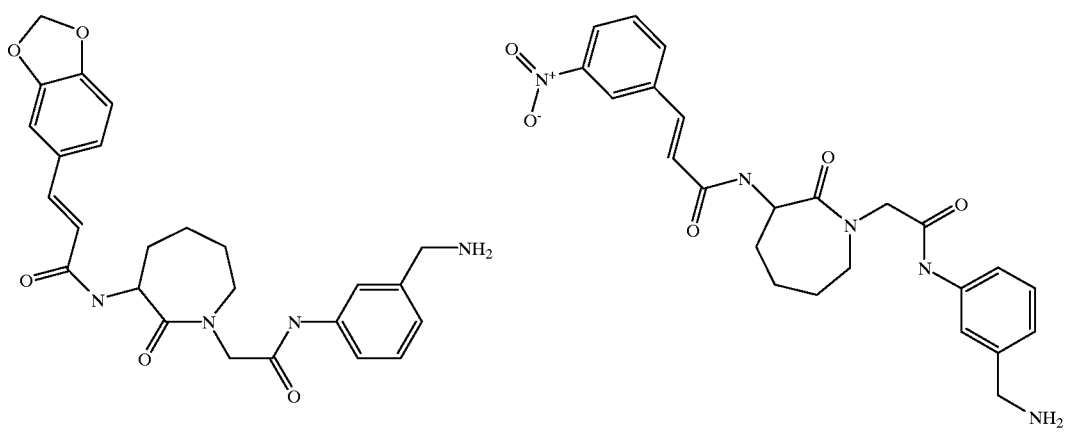
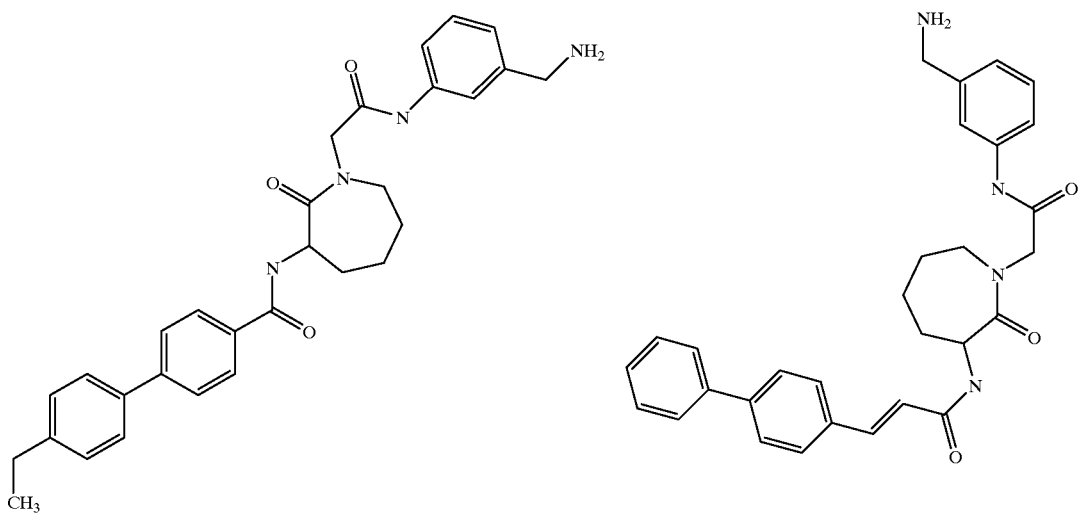
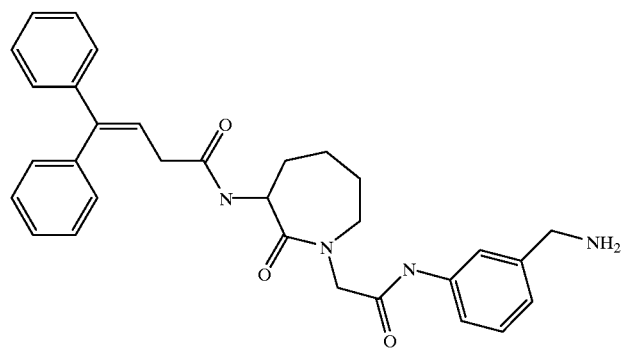

-continued
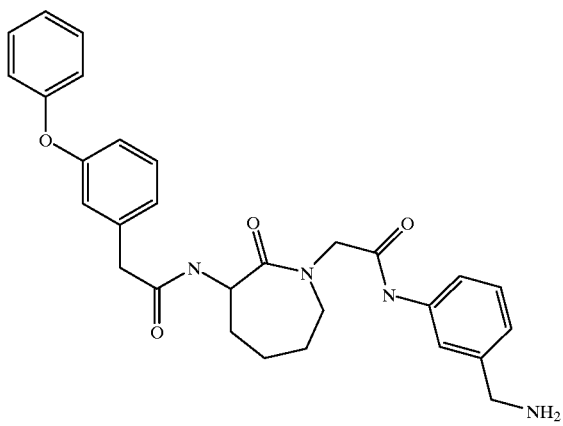
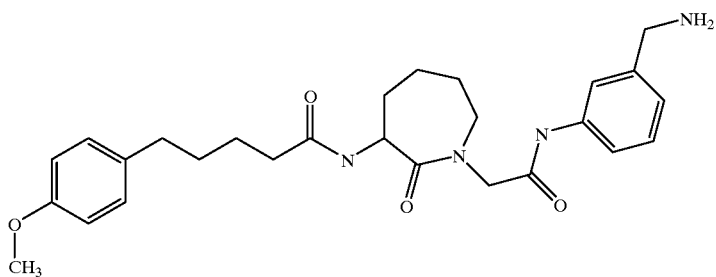
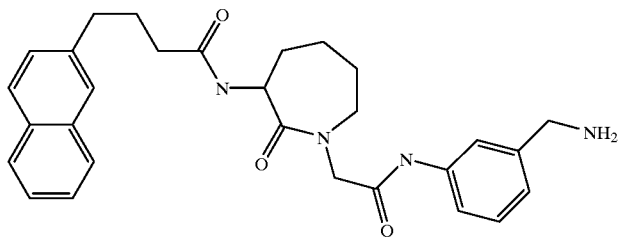
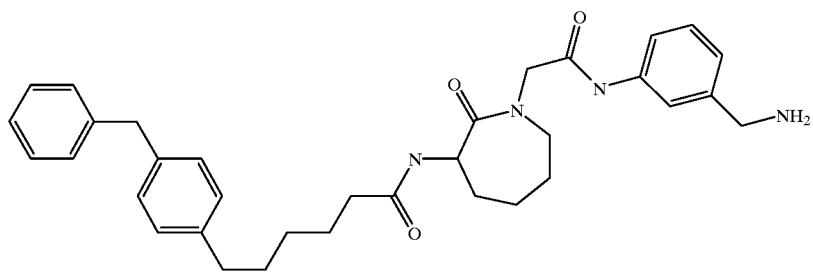
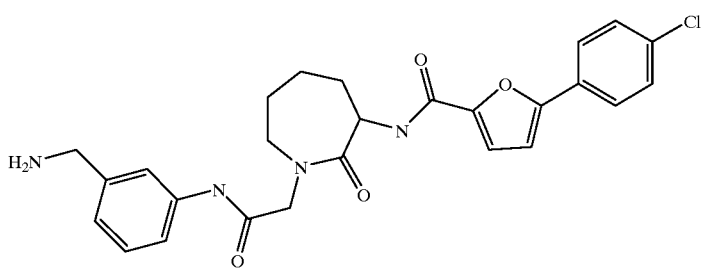

163 164
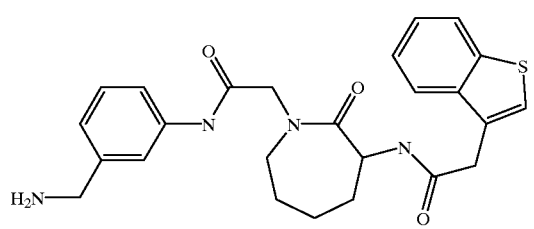
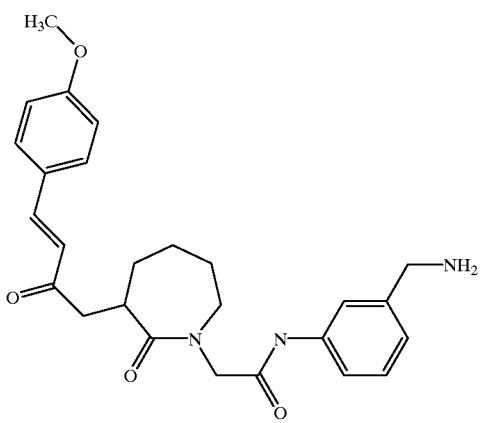
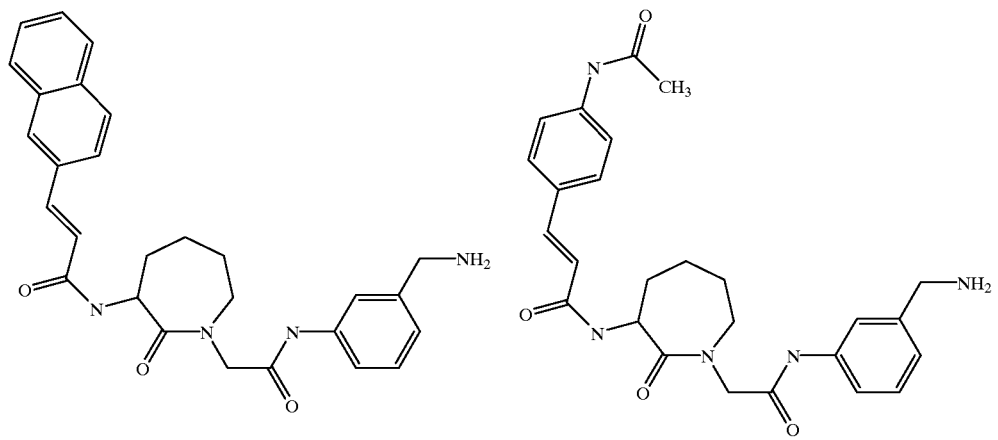
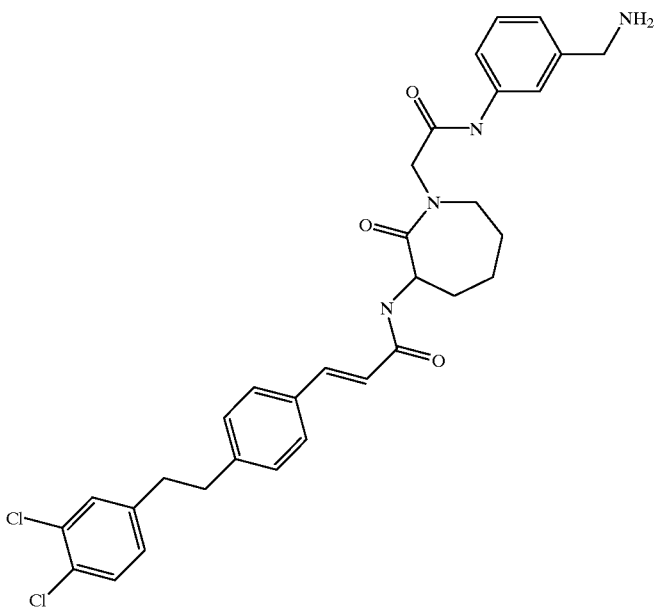

-continued
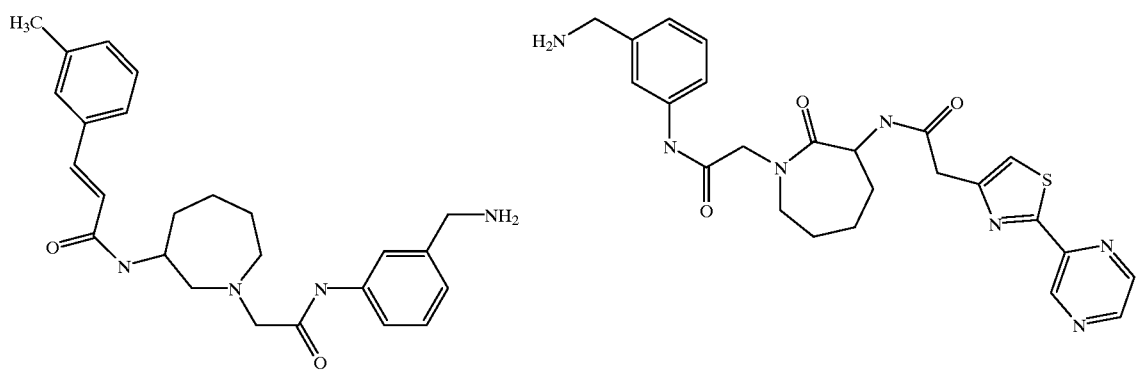
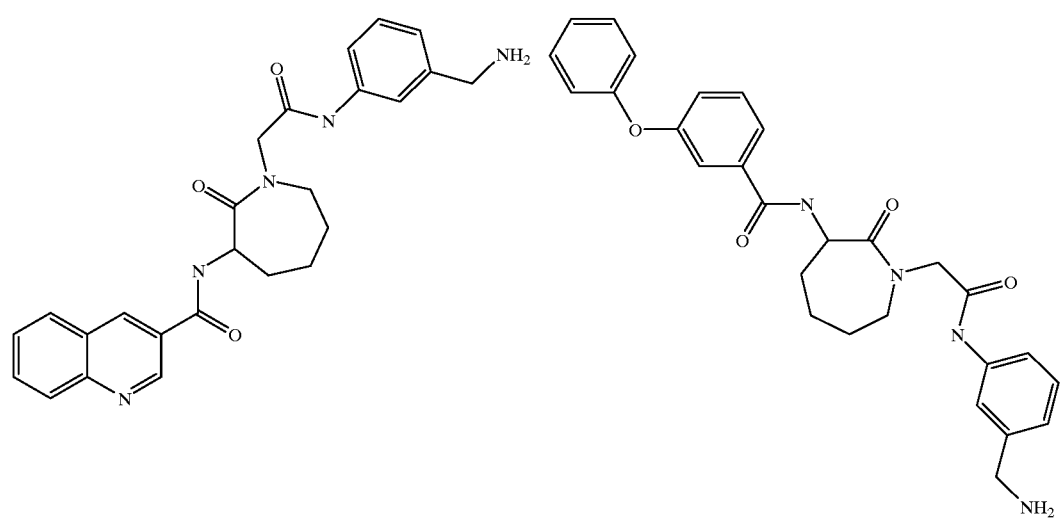
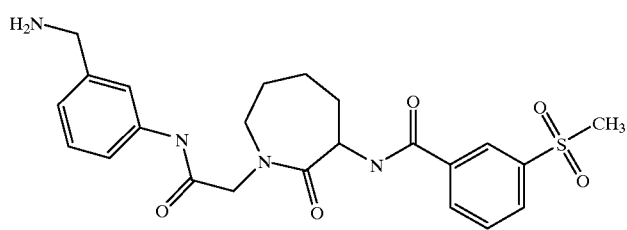
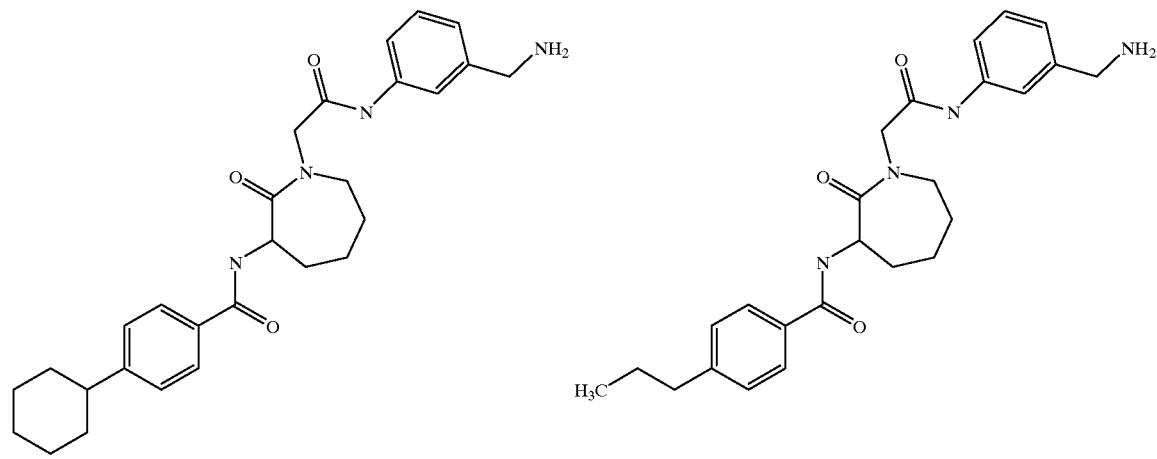

167                                    168
-continued
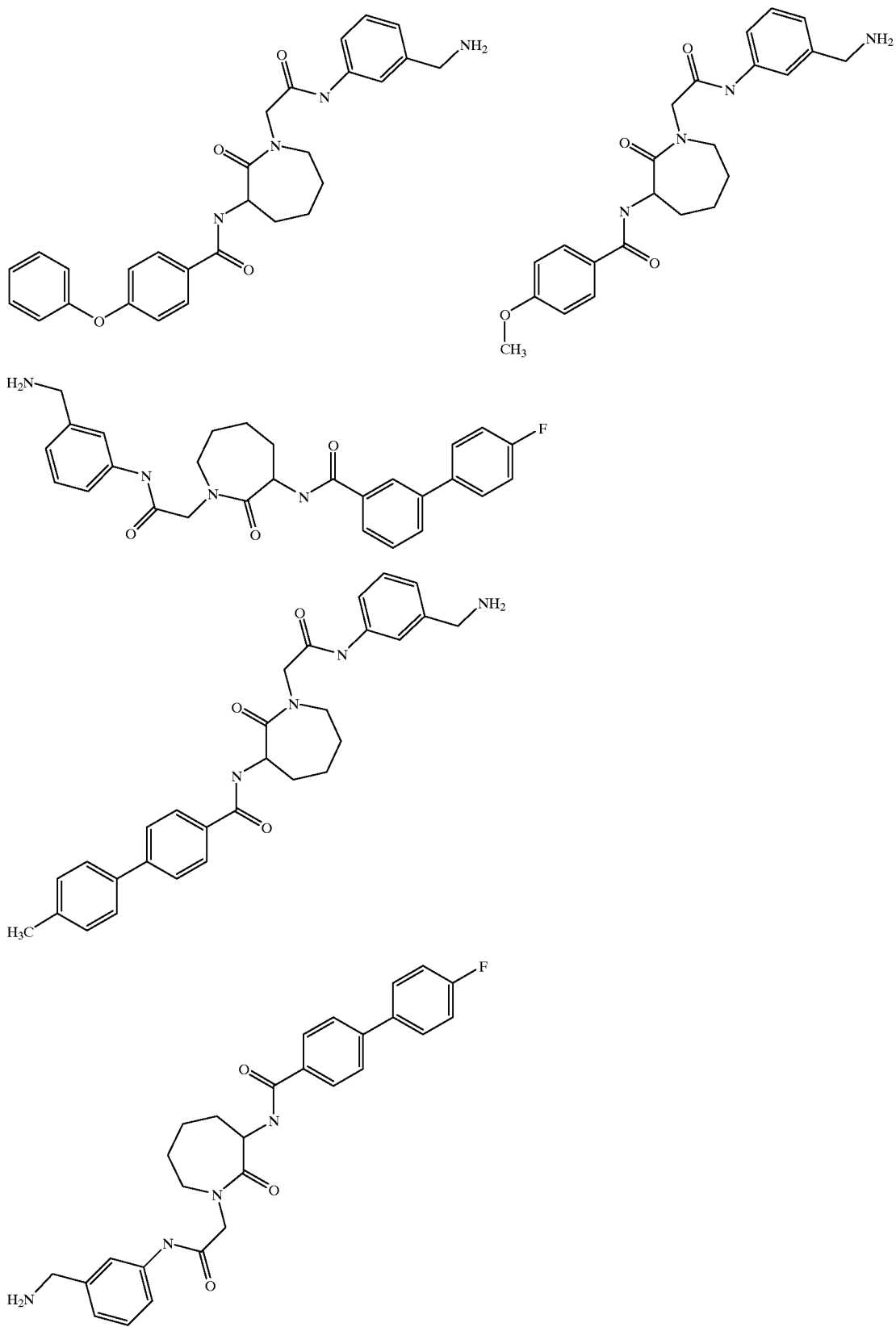

-continued
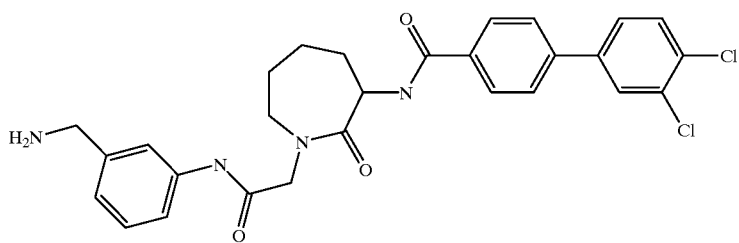
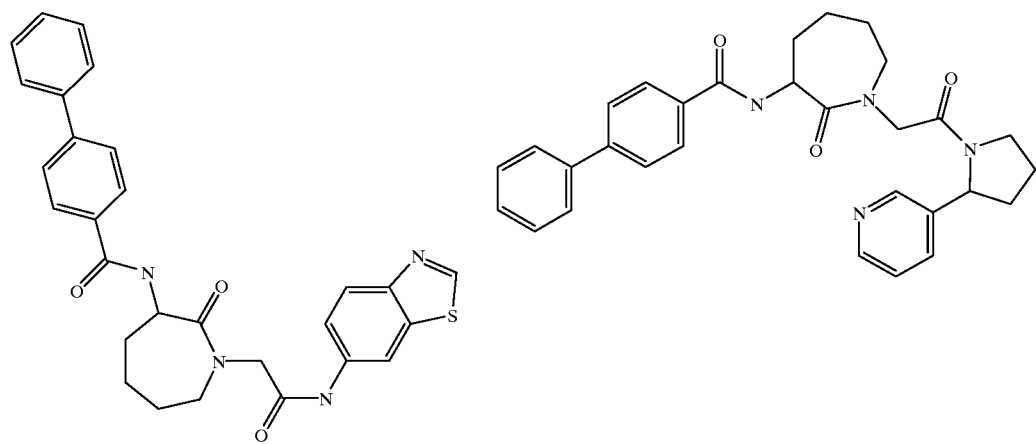
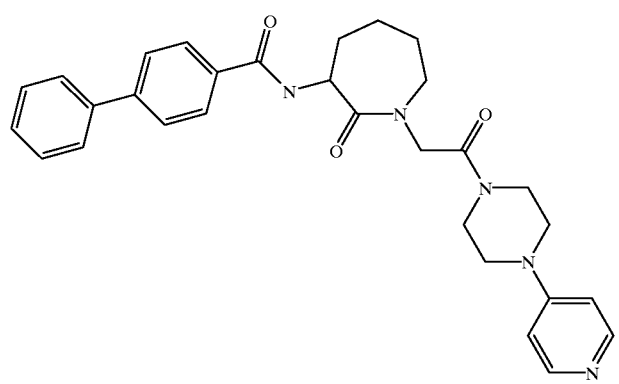
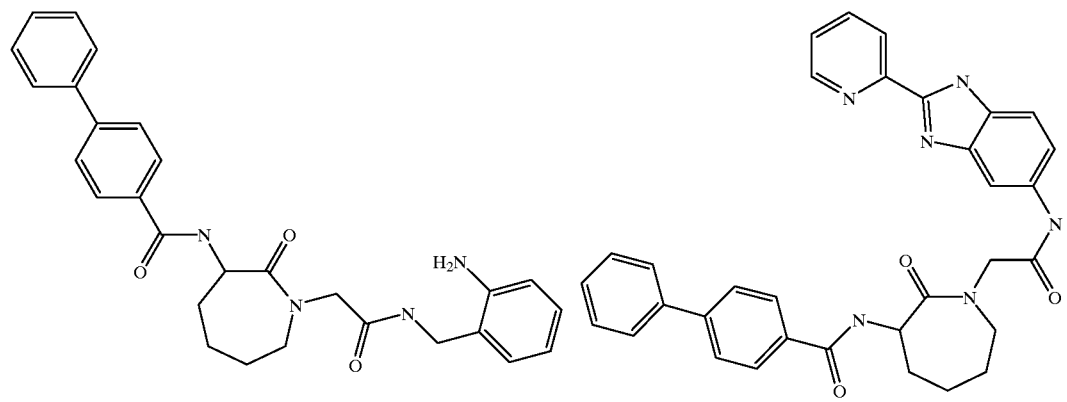

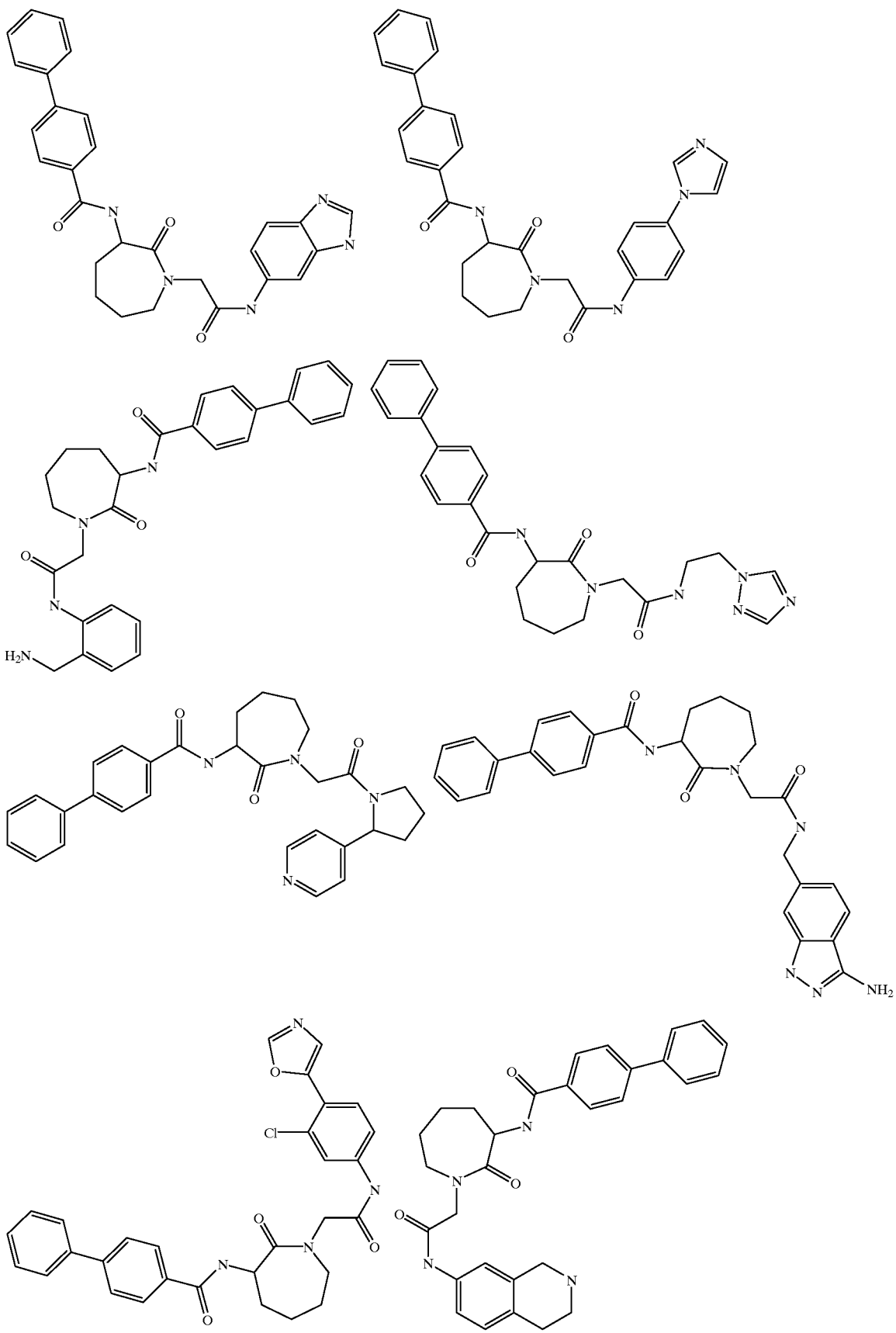

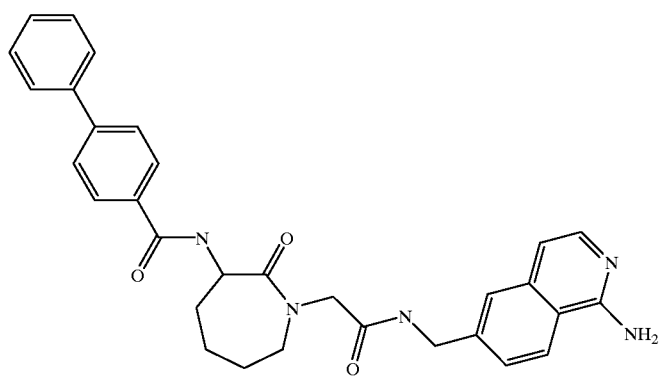
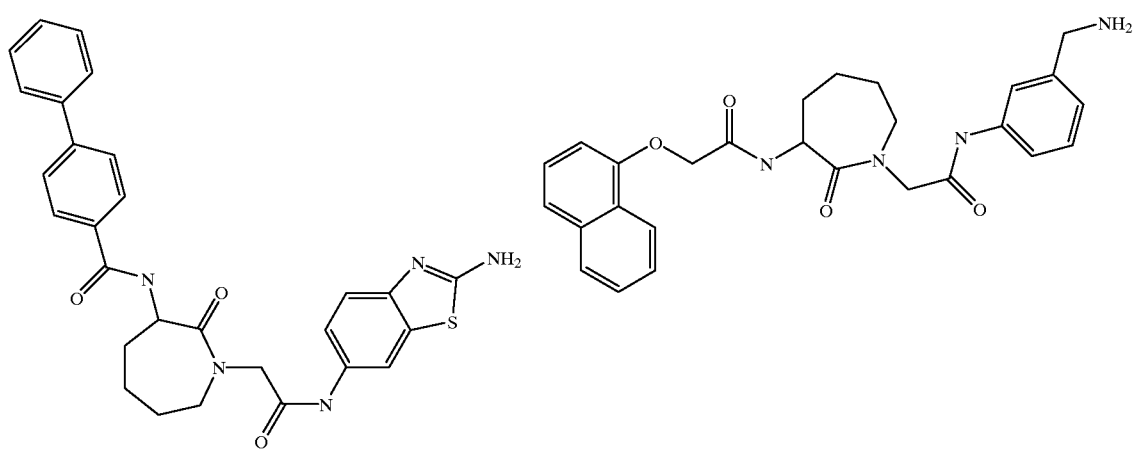
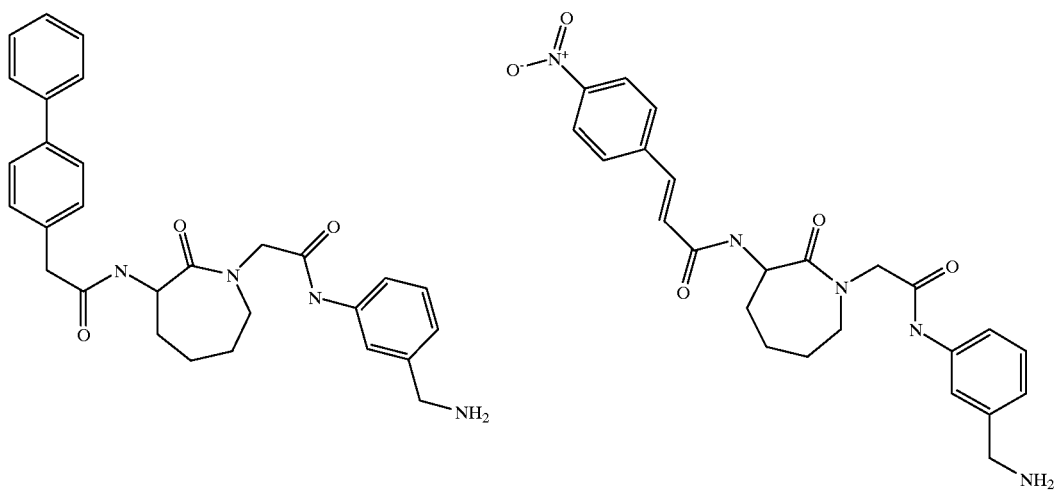

-continued
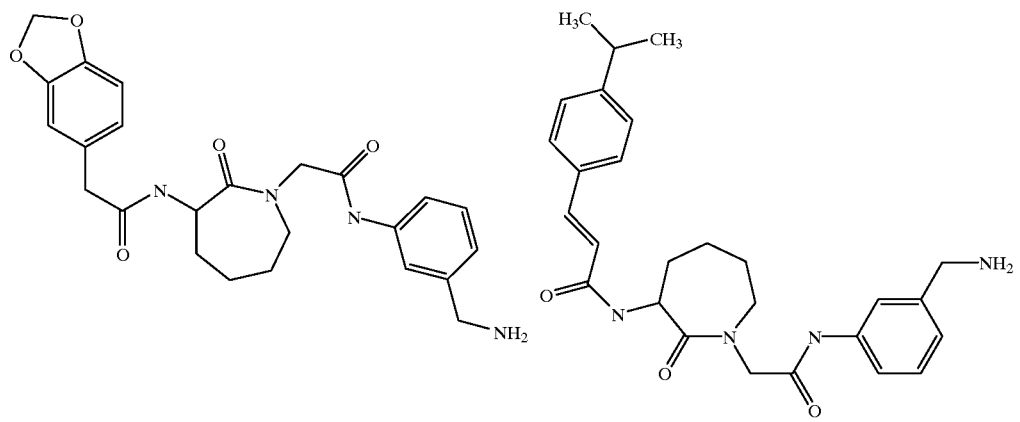
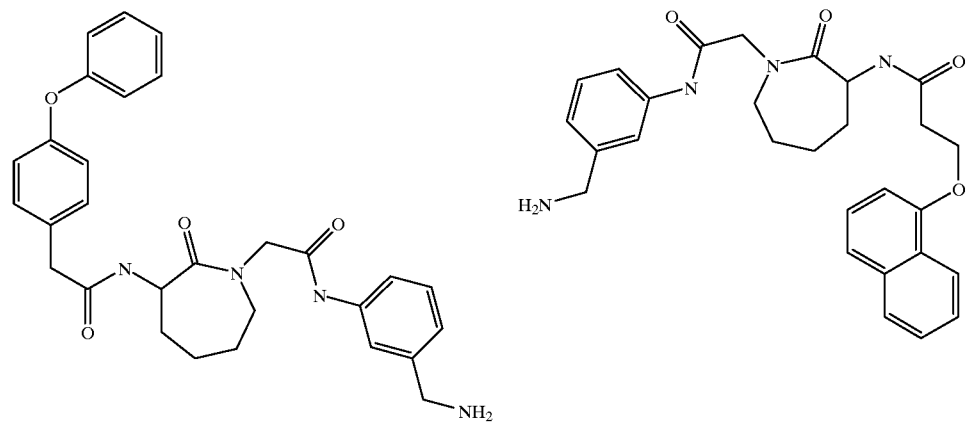
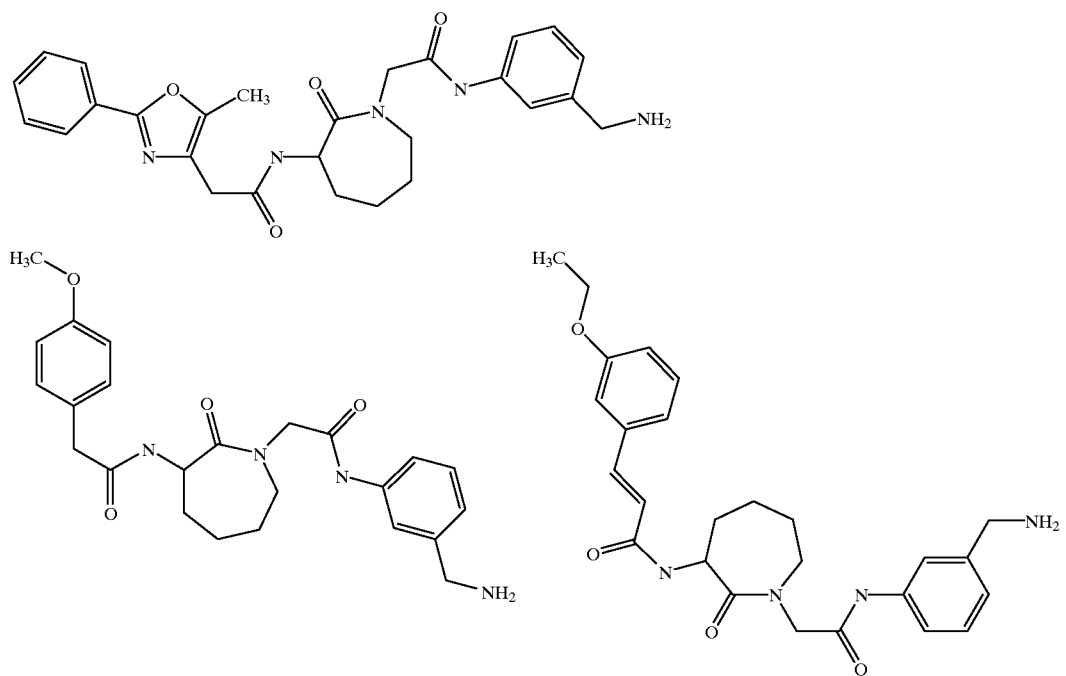

-continued
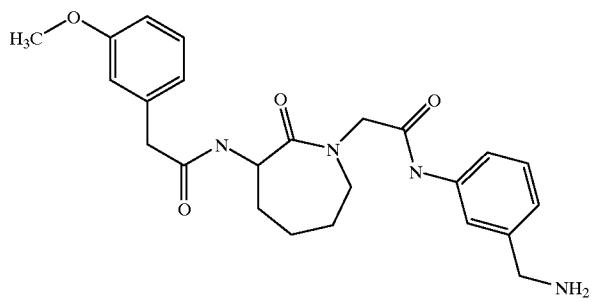
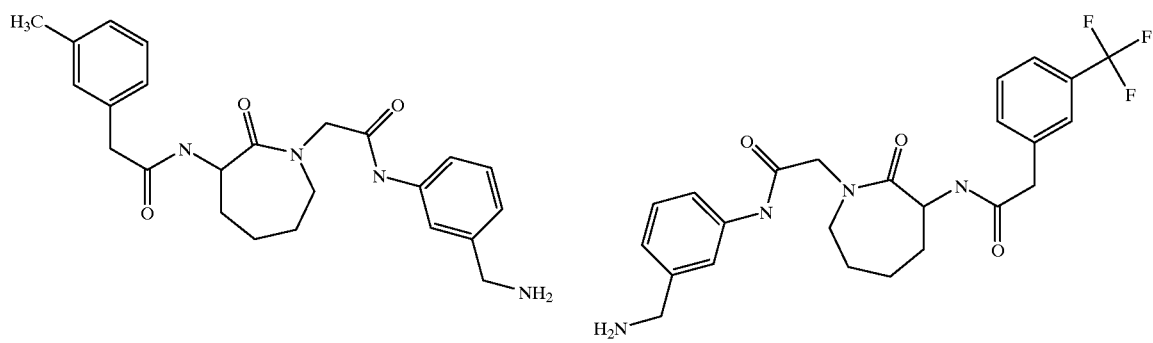
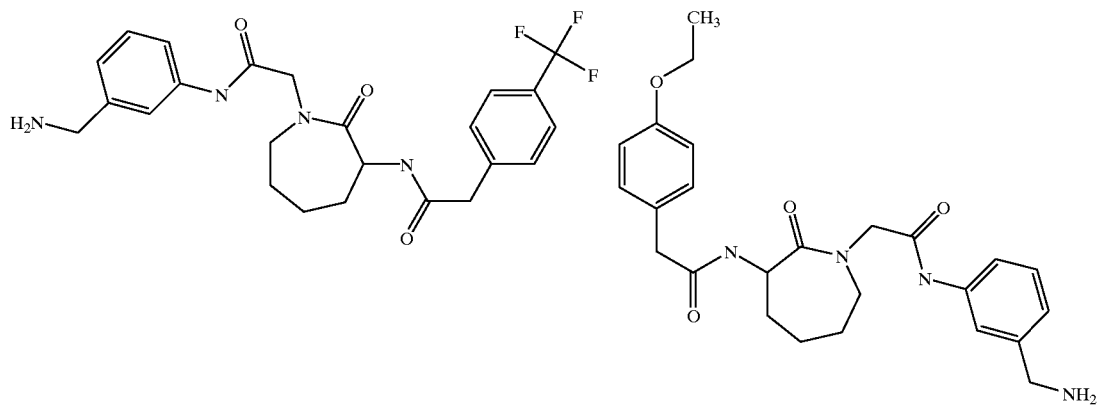
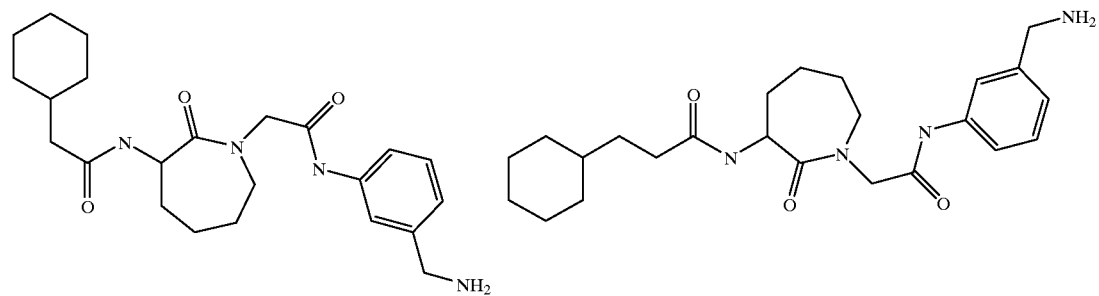

-continued
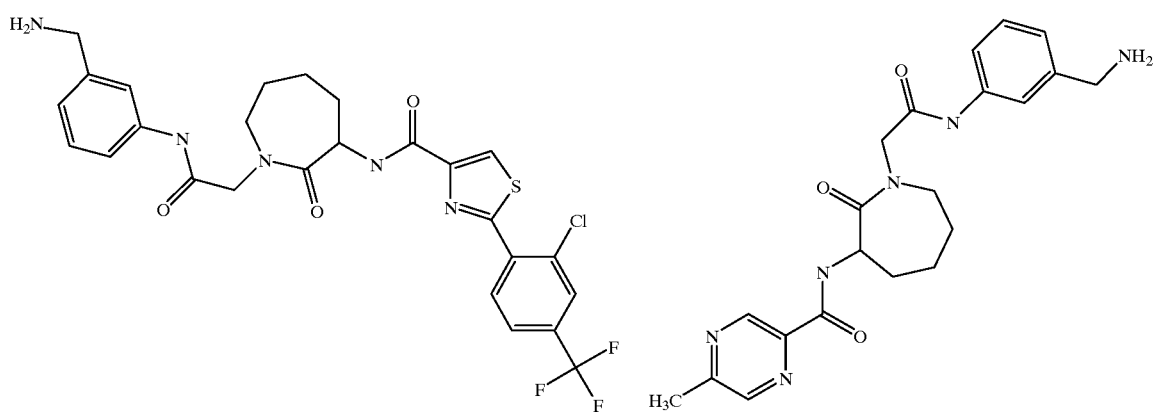
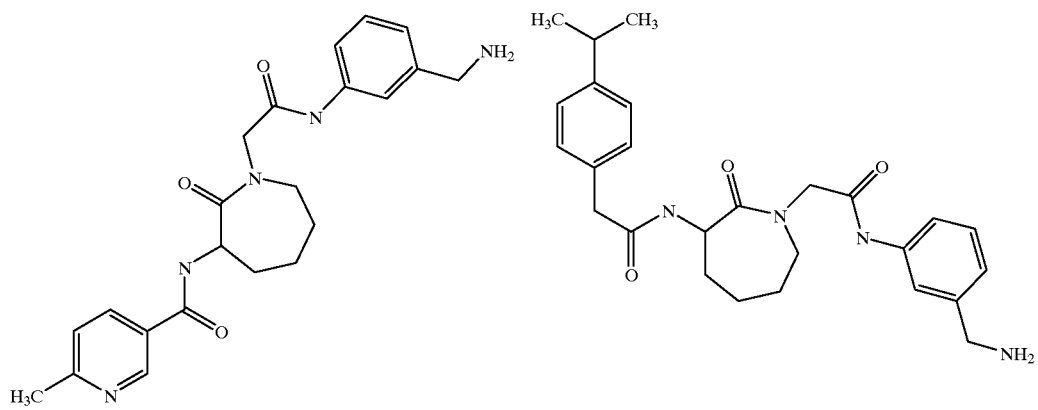
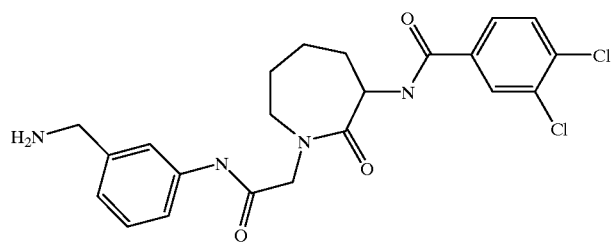
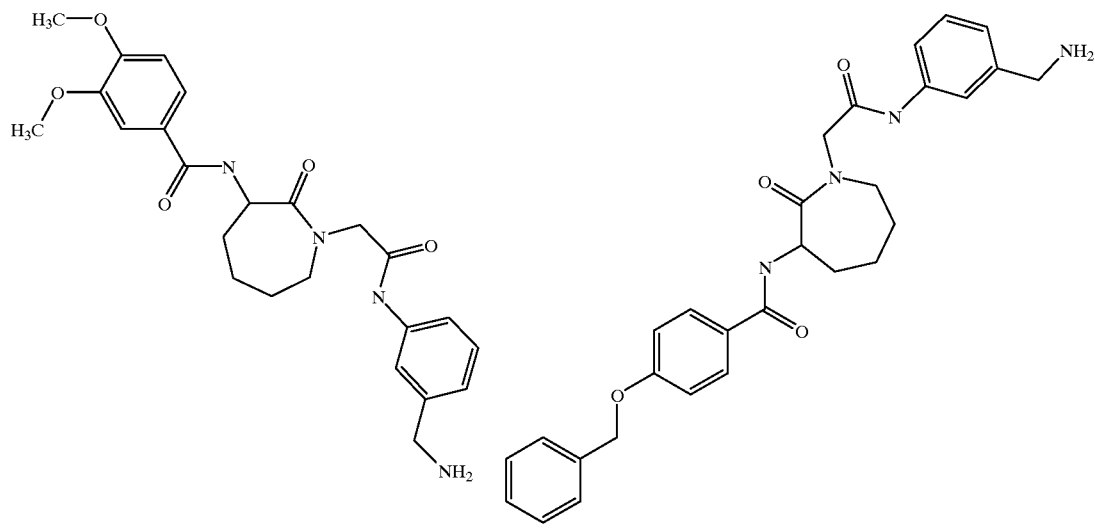

181 182
-continued
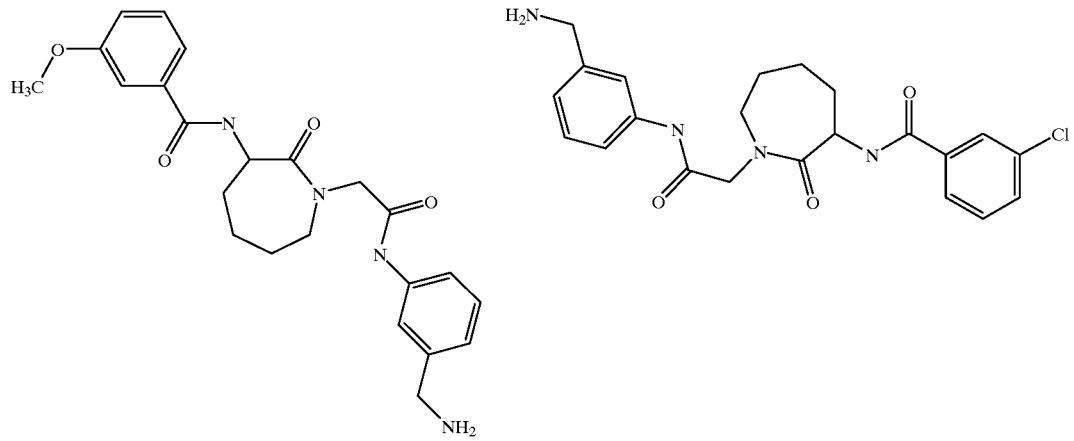
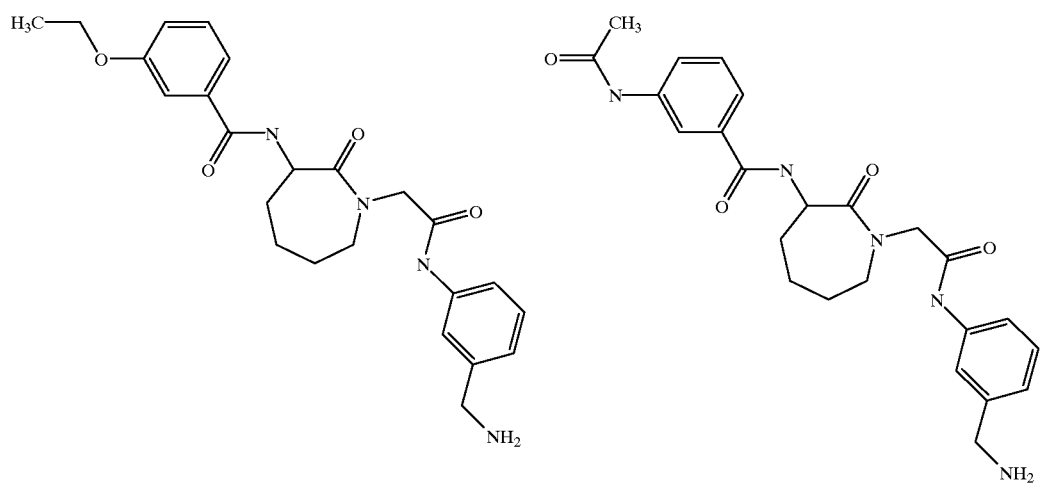
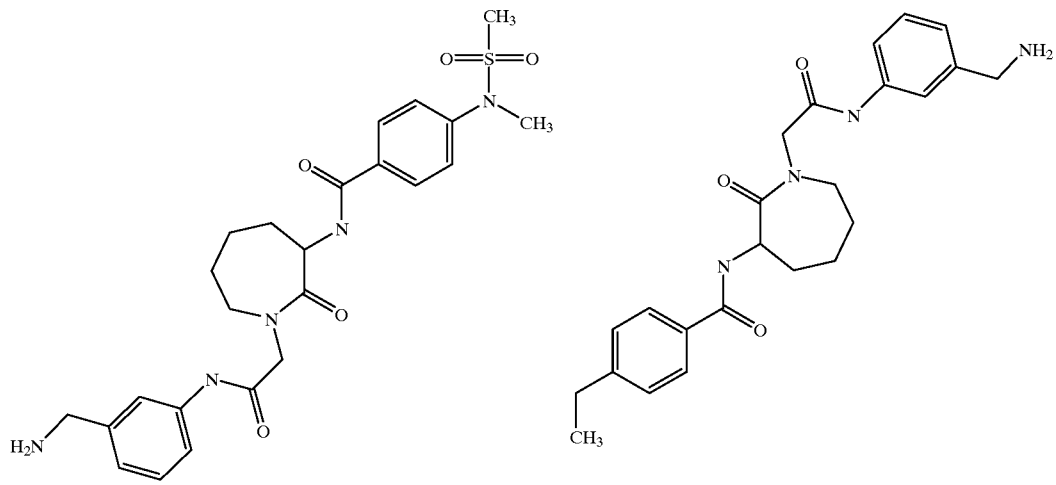

183
-continued
184
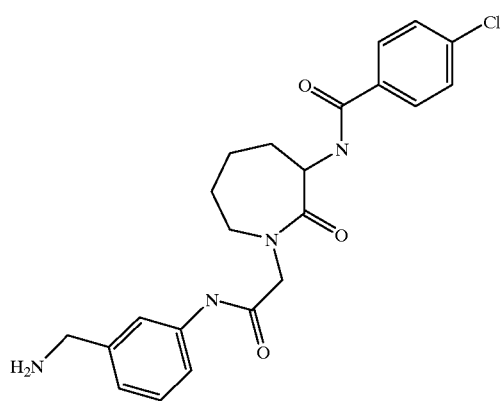
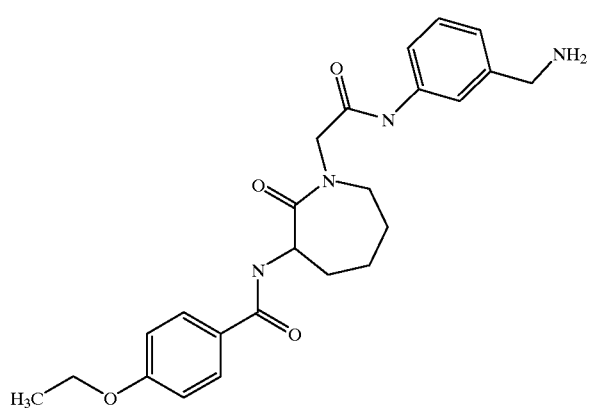
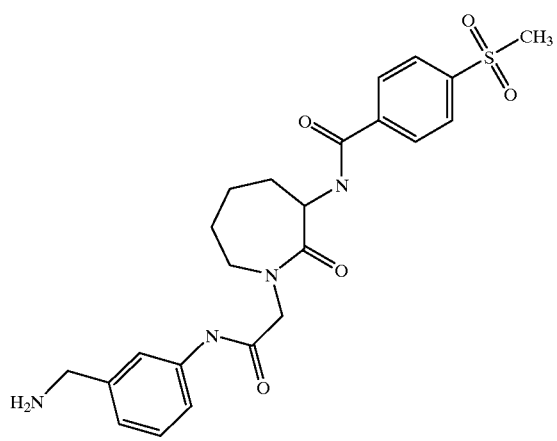
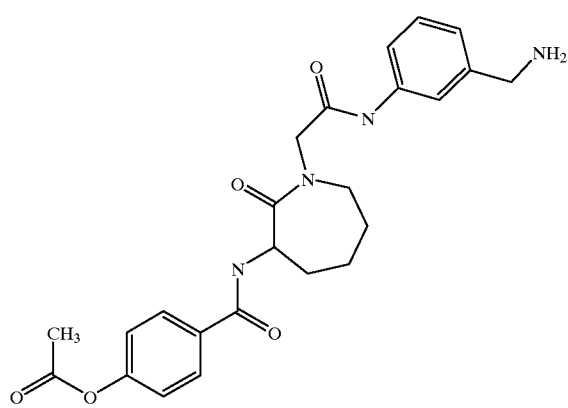
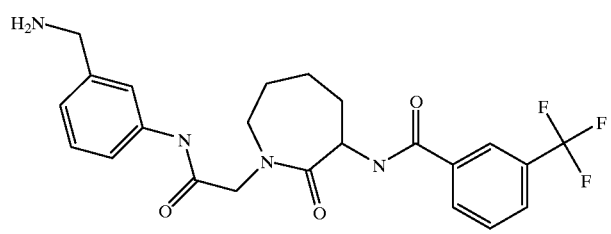
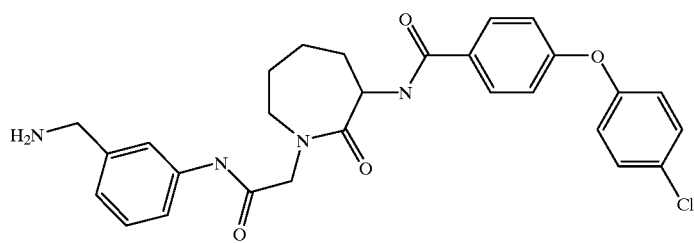

-continued
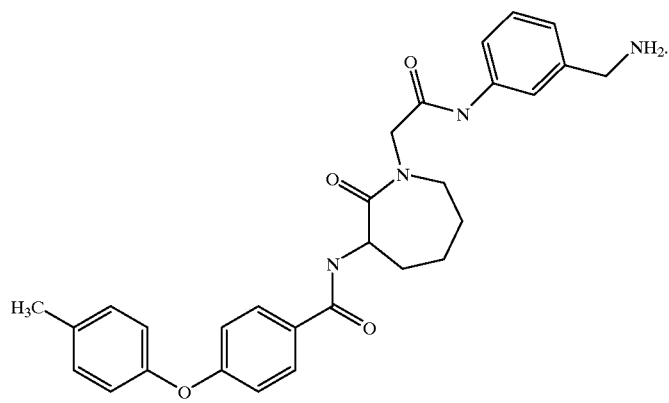
19. The compound as defined in claim 1 having the structure
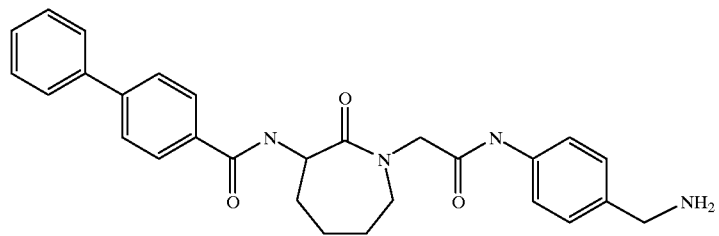
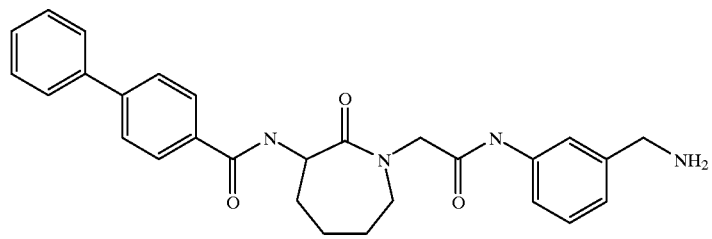
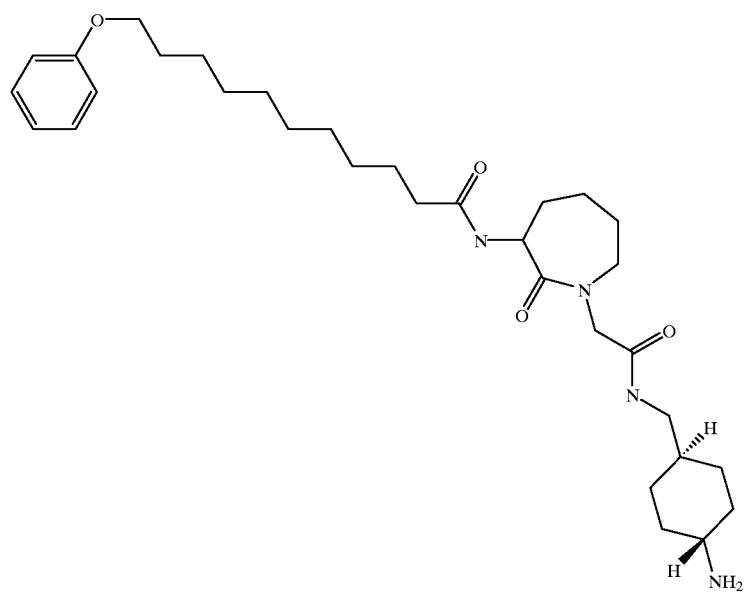

187
188
-continued
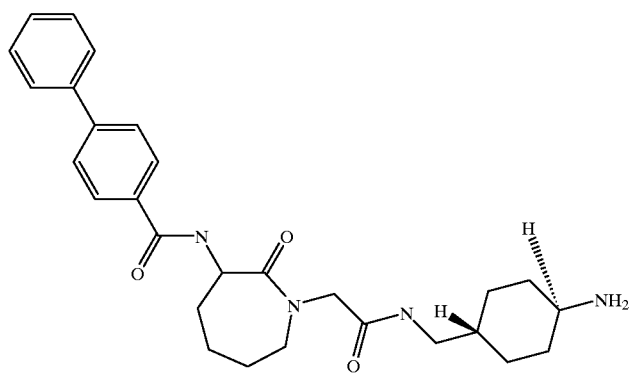
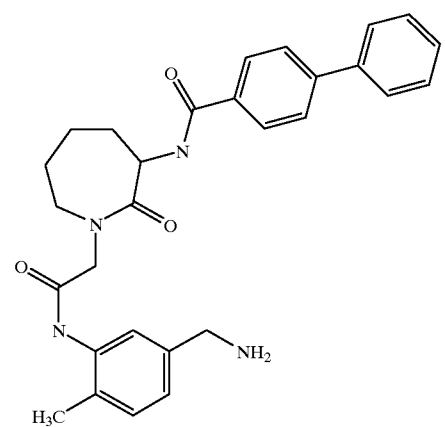
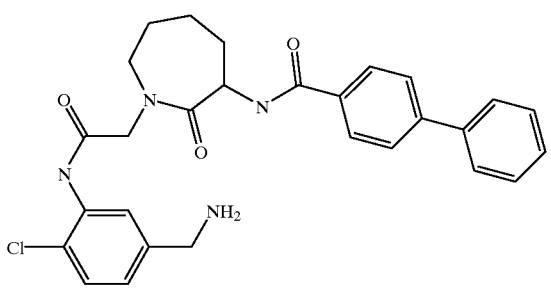
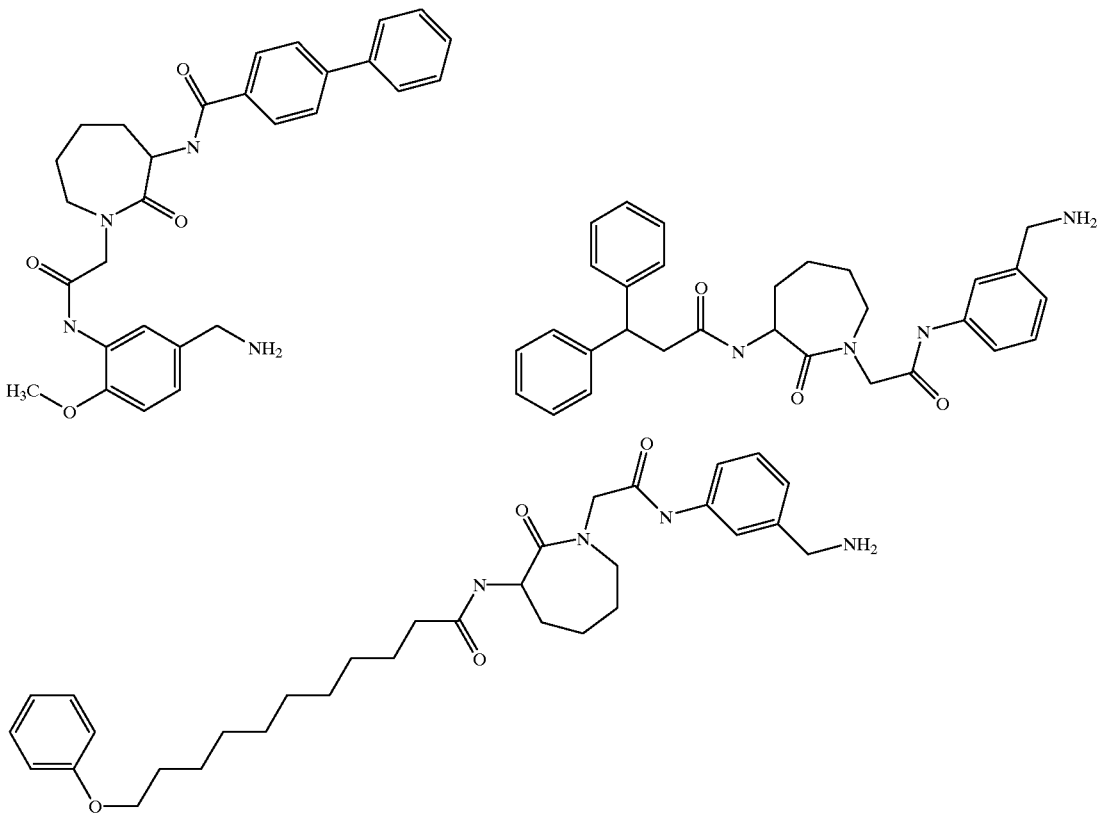

-continued
189
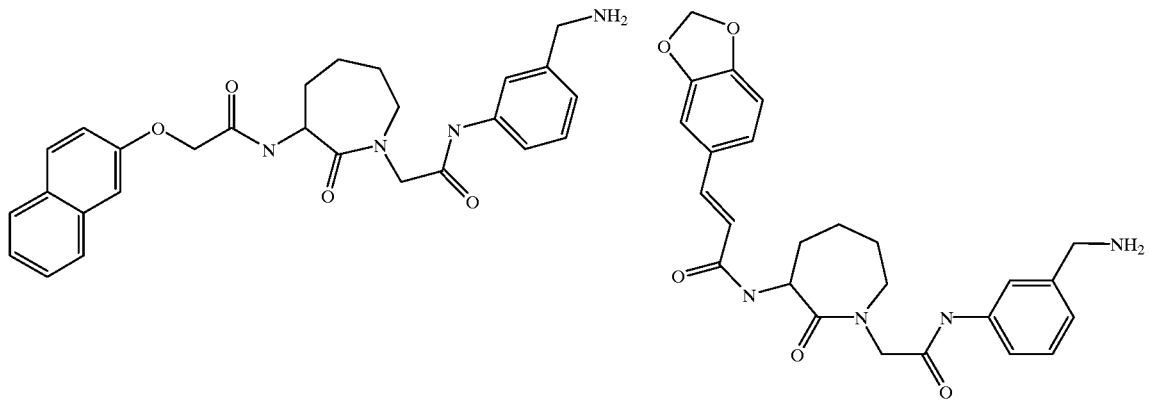
190
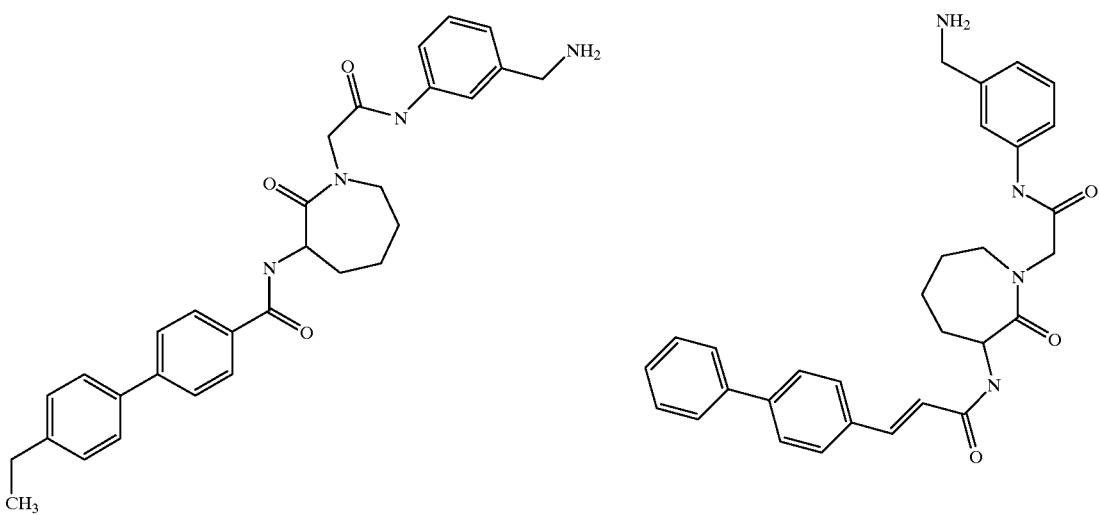
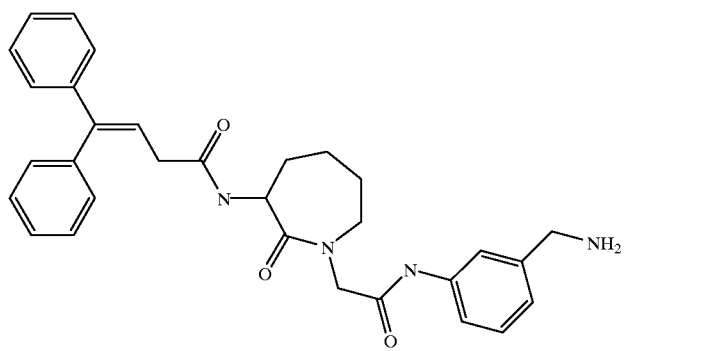
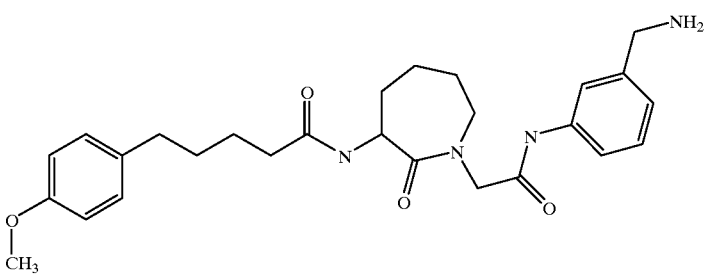

-continued
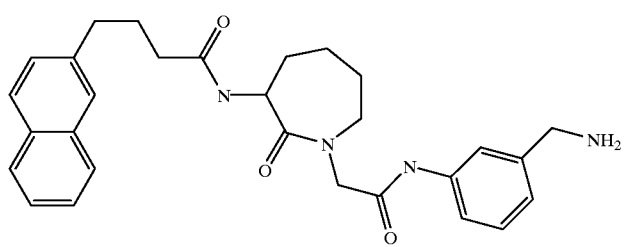
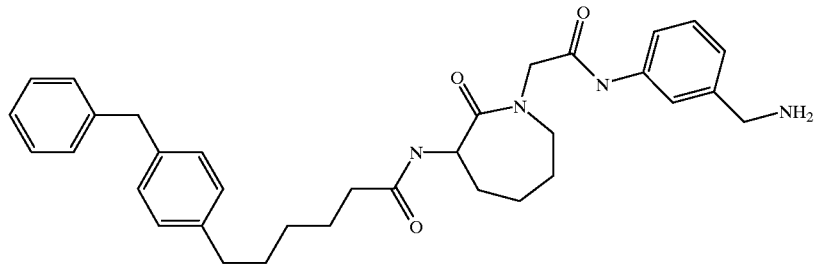
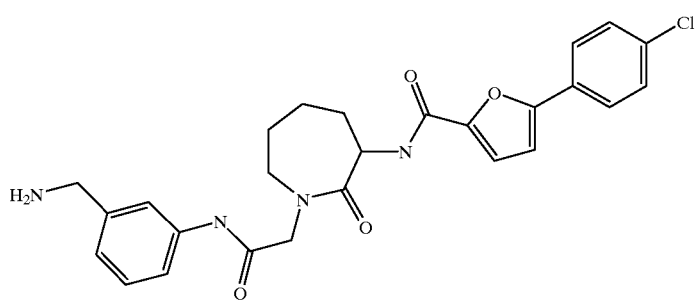
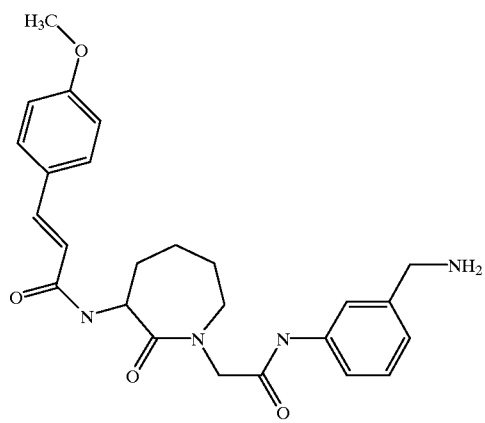
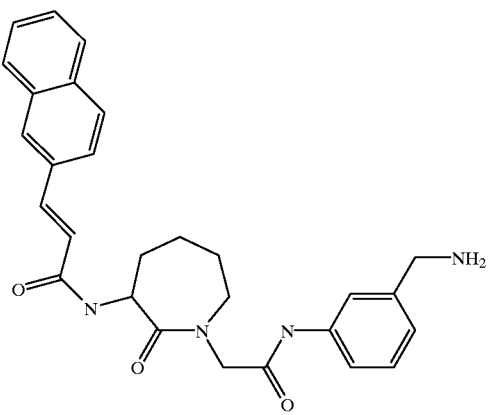
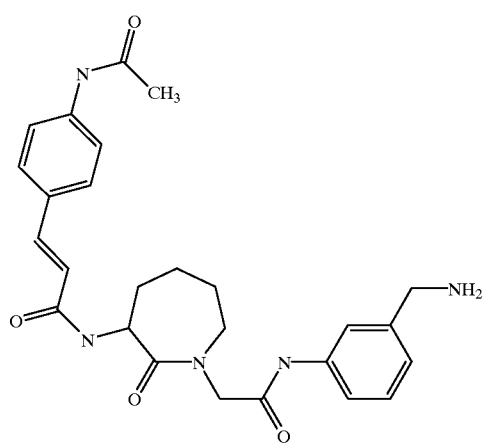

193
-continued
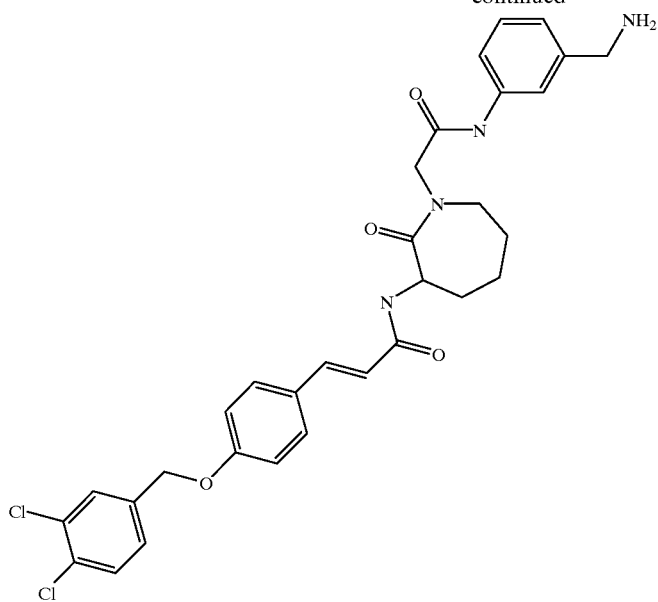
194
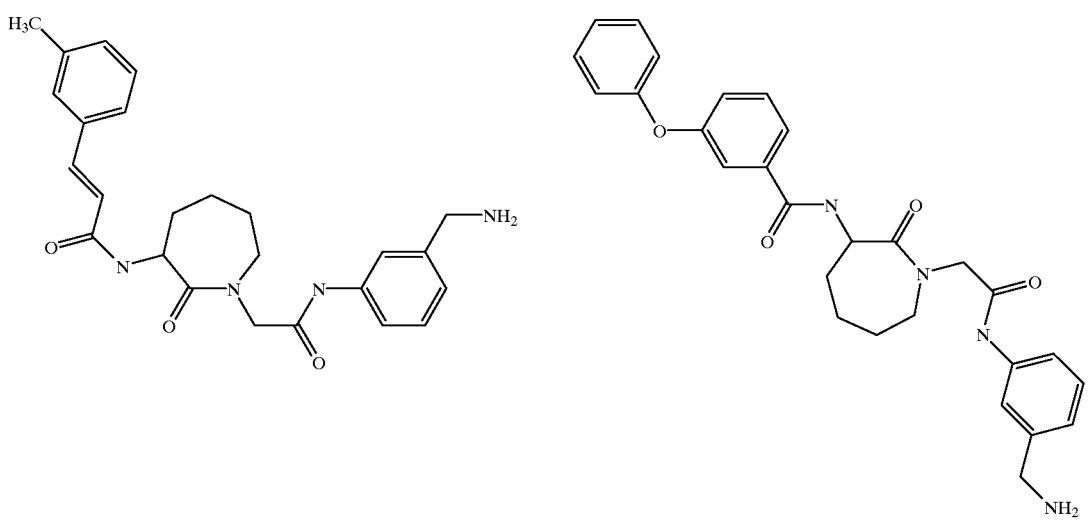
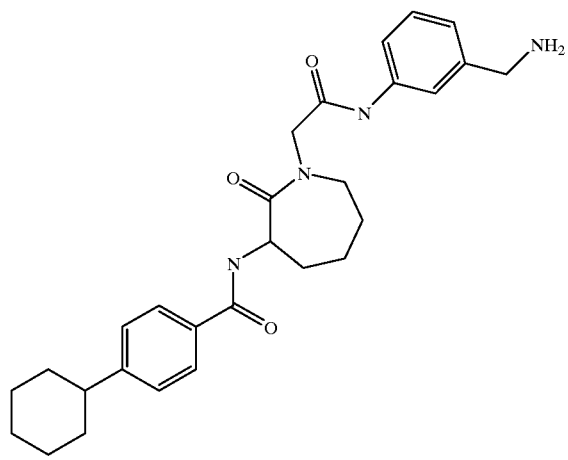

-continued
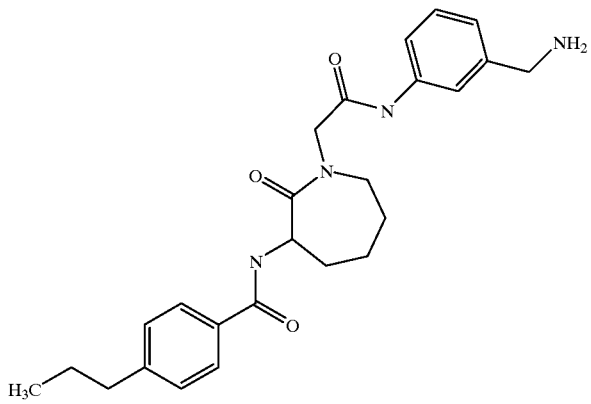
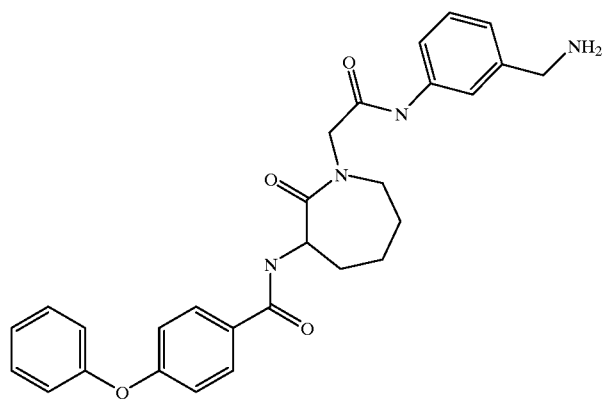
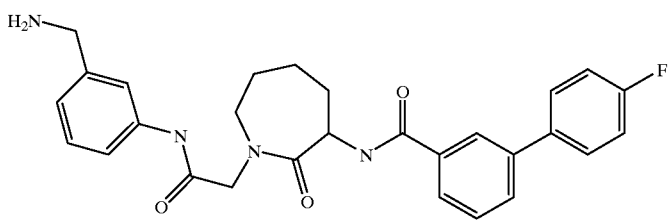
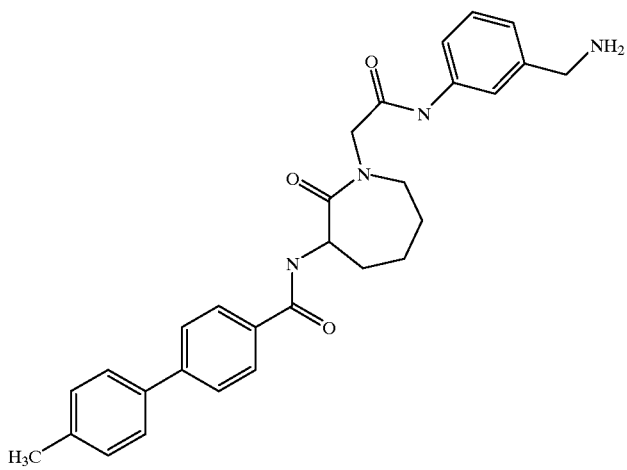

-continued
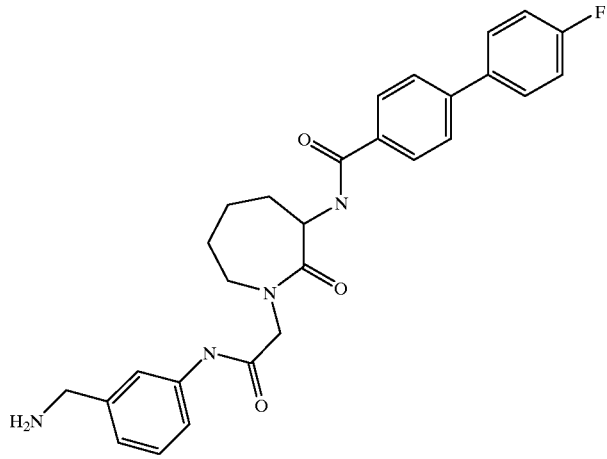
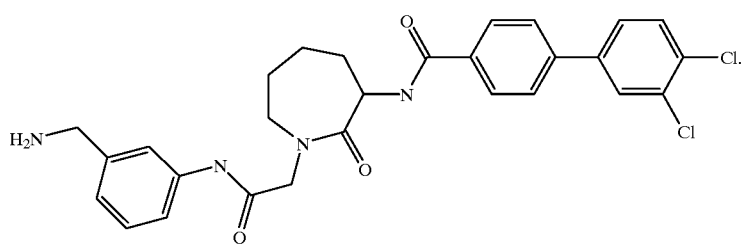
20. The compound as defined in claim 1 having the structure.
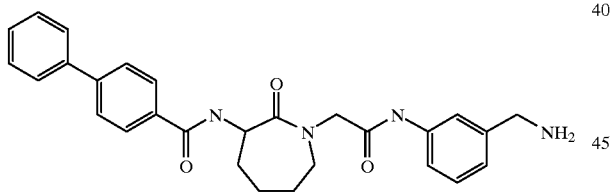
-continued
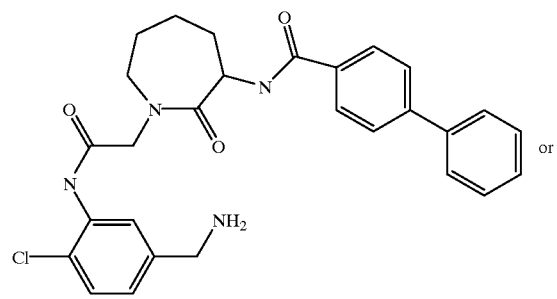
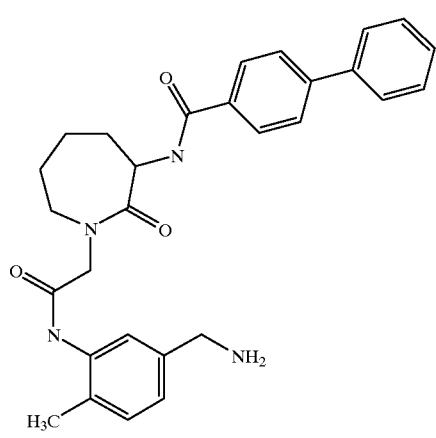
21. A compound having the structure
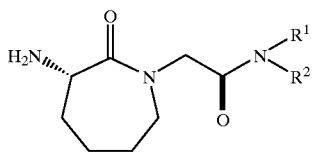

wherein $R^1$ and $R^2$ are the same or different and are independently selected from hydrogen, alkynyl, heteroaryl, aminoalkylaryl, aminocycloalkylalkyl, aminoalkyl, aminoalkylcycloalkyl, heteroarylalkyl, cycloalkenyl, cycloheteroalkyl, heteroaryloxy, cycloalkenylalkyl, polycycloalkenyl, polycycloalkenylalkyl, or $R^1$ and $R^2$ can be taken with the nitrogen to which they are attached to form a cycloheteroalkyl ring; all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, alkylamino, dialkylamino, thiol, alkylthio, arylthio, heteroarylthio, arylthioalkyl, aminoalkyl, alkyloxycarbonylaminoalkyl, arylalkyloxycarbonylaminoalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl; or a pharmaceutically acceptable salt thereof, with the proviso that at least one of $R^1$ and $R^2$ is other than hydrogen.

22. The compound as defined in claim 21 having the formula

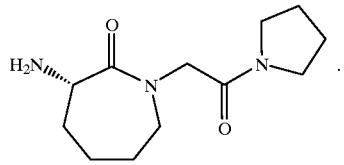

23. A pharmaceutical composition comprising a compound as defined in claim 1 and a pharmaceutically acceptable carrier therefor.

24. A method for treating cardiovascular diseases associated with thromboses, which comprises administering to a mammalian species in need of treatment a therapeutically effective amount of a compound as defined in claim 1.

25. A method for treating thromboses, coronary artery disease or cerebrovascular disease, associated with thrombosis which comprises administering to a mammalian species in need of treatment a therapeutically effective amount of a compound as defined in claim 1.

26. A method for treating inflammation, asthma, or allergic rhinitis which comprises administering to a mammalian species in need of treatment a therapeutically effective amount of a compound as defined in claim 1.

27. A method for treating asthma in a mammalian species comprising administering to a mammalian species in need of treatment a therapeutically effective amount of a compound as defined in claim 1.

28. The method as defined in claim 25 wherein the cardiovascular diseases are atherosclerotic plaques, venous or arterial thrombosis, coagulation syndromes, ischemia and angina (stable and unstable), deep vein thrombosis (DVT), disseminated intravascular coagulopathy, Kasabach-Merritt syndrome, pulmonary embolism, myocardial infarction, cerebral infarction, cerebral thrombosis, atrial fibrillation, cerebral embolism, thromboembolic complications of surgery, peripheral arterial occlusion, or restenosis following arterial injury induced by endogenous or exogenous events.

29. A method for treating inflammatory bowel disease, psoriasis, conjunctivitis, atopic dermatitis, rheumatoid arthritis, osteoarthritis, chronic inflammatory joint disease, diseases of joint cartilage destruction, allergic rhinitis myocardial infarction, stroke, angina, treating or preventing diabetic retinopathy, fibrosis, scleroderma, pulmonary fibrosis, liver cirrhosis, myocardial fibrosis, neurofibromas and hypetrophic scars, which comprises administering to a mammalian species in need of treatment a therapeutically effective amount of a compound as defined in claim 1.

* * * * *